US009533943B2

(12) United States Patent
Bowser et al.

(10) Patent No.: US 9,533,943 B2
(45) Date of Patent: Jan. 3, 2017

(54) SUBSTITUTED TETRACYCLINE COMPOUNDS

(71) Applicant: Paratek Pharmaceuticals, Inc., Boston, MA (US)

(72) Inventors: Todd Bowser, Charlton, MA (US); Mark Grier, Midvale, UT (US)

(73) Assignee: Paratek Pharmaceuticals, Inc., Boston, MA (US)

( * ) Notice: Subject to any disclaimer, the term of this patent is extended or adjusted under 35 U.S.C. 154(b) by 0 days.

(21) Appl. No.: 14/281,357

(22) Filed: May 19, 2014

(65) Prior Publication Data

US 2015/0045329 A1 Feb. 12, 2015

Related U.S. Application Data

(63) Continuation of application No. 10/877,928, filed on Jun. 25, 2004, now abandoned.

(60) Provisional application No. 60/530,123, filed on Dec. 16, 2003, provisional application No. 60/525,287, filed on Nov. 25, 2003, provisional application No. 60/486,017, filed on Jul. 9, 2003.

(51) Int. Cl.
| | |
|---|---|
| *A61K 31/65* | (2006.01) |
| *C07C 237/26* | (2006.01) |
| *C07C 237/48* | (2006.01) |
| *C07C 271/22* | (2006.01) |
| *C07C 271/54* | (2006.01) |
| *C07C 275/28* | (2006.01) |
| *C07C 275/30* | (2006.01) |

(52) U.S. Cl.
CPC ........... *C07C 237/48* (2013.01); *C07C 237/26* (2013.01); *C07C 271/22* (2013.01); *C07C 271/54* (2013.01); *C07C 275/28* (2013.01); *C07C 275/30* (2013.01); *A61K 31/65* (2013.01); *C07C 2101/02* (2013.01); *C07C 2101/14* (2013.01); *C07C 2101/16* (2013.01); *C07C 2103/46* (2013.01)

(58) Field of Classification Search
CPC .............................. C07C 237/26; A61K 31/65
USPC .......................................... 552/205; 514/152
See application file for complete search history.

(56) References Cited

U.S. PATENT DOCUMENTS

| | | |
|---|---|---|
| 2,980,584 A | 4/1961 | Hammer |
| 2,990,331 A | 6/1961 | Neumann, et al. |
| 3,007,965 A | 11/1961 | Growich |
| 3,043,875 A | 7/1962 | Beereboom |
| 3,062,717 A | 11/1962 | Hammer |
| 3,069,467 A | 12/1962 | Beereboom et al. |
| 3,165,531 A | 1/1965 | Blackwood et al. |
| 3,200,149 A | 8/1965 | Blackwood et al. |
| 3,219,671 A | 11/1965 | Hlavka |
| 3,226,436 A | 12/1965 | Petisi et al. |
| 3,277,172 A | 10/1966 | Aliciano et al. |
| RE26,253 E | 8/1967 | Patisi et al. |
| 3,338,963 A | 8/1967 | Petisi et al. |
| RE26,271 E | 9/1967 | Boothe et al. |
| 3,341,585 A | 9/1967 | Bitha et al. |
| 3,345,379 A | 10/1967 | Martell et al. |
| 3,345,410 A | 10/1967 | Winterbottom et al. |
| 3,350,557 A | 10/1967 | Szymanski |
| 3,360,561 A | 12/1967 | Zambrano |
| 3,373,196 A | 3/1968 | Bitha |
| 3,397,230 A | 8/1968 | Winterbottom et al. |
| 3,403,179 A | 9/1968 | Zambrano |
| 3,433,834 A | 3/1969 | Winterbottom et al. |
| 3,454,697 A | 7/1969 | Joyner, et al. |
| 3,483,251 A | 12/1969 | Zambrano |
| 3,518,306 A | 6/1970 | Martell, Jr. |
| 3,557,280 A | 1/1971 | Weber et al. |
| 3,579,579 A | 5/1971 | Hlavka et al. |
| 3,609,188 A | 9/1971 | Esse et al. |
| 3,674,859 A | 7/1972 | Beutel et al. |
| 3,795,707 A | 3/1974 | Luciano |
| 3,849,493 A | 11/1974 | Conover |
| 3,862,225 A | 1/1975 | Conover et al. |
| 3,901,942 A | 8/1975 | Bernardi et al. |
| 3,957,980 A | 5/1976 | Noseworthy |
| 3,993,694 A | 11/1976 | Martin et al. |
| 4,018,889 A | 4/1977 | Armstrong |
| 4,024,272 A | 5/1977 | Rogalski et al. |
| 4,126,680 A | 11/1978 | Armstrong |
| 4,806,372 A | 2/1989 | Strumskis |
| 5,021,407 A | 6/1991 | Levy |
| 5,248,797 A | 9/1993 | Sum |
| 5,258,372 A | 11/1993 | Levy |

(Continued)

FOREIGN PATENT DOCUMENTS

| | | |
|---|---|---|
| EP | 535346 A1 | 4/1993 |
| EP | 536515 A1 | 4/1993 |

(Continued)

OTHER PUBLICATIONS

Barden T. et al., "Glycylcyclines'. 3. 9-Aminodoxycylinercarboxamides," J. Med. Chem., vol. 37, pp. 3205-3211, 1994.

(Continued)

*Primary Examiner* — Barbara P Badio

(74) *Attorney, Agent, or Firm* — McCarter & English, LLP; Elizabeth A. Hanley

(57) ABSTRACT

The present invention pertains, at least in part, to novel substituted etracycline compounds. These tetracycline compounds can be used to treat numerous tetracycline compound-responsive states, such as bacterial infections and neoplasms, as well as other known applications for tetracycline compounds such as blocking tetracycline efflux and modulation of gene expression.

2 Claims, No Drawings

(56) References Cited

U.S. PATENT DOCUMENTS

| | | |
|---|---|---|
| 5,281,628 A | 1/1994 | Hlavka et al. |
| 5,284,963 A | 2/1994 | Sum et al. |
| 5,326,759 A | 7/1994 | Hlavka et al. |
| 5,328,902 A | 7/1994 | Sum et al. |
| 5,371,076 A | 12/1994 | Lee et al. |
| 5,380,888 A | 1/1995 | Sum et al. |
| 5,386,041 A | 1/1995 | Sum et al. |
| 5,401,729 A | 3/1995 | Sum et al. |
| 5,401,863 A | 3/1995 | Hlavka et al. |
| 5,420,272 A | 5/1995 | Sum et al. |
| 5,430,162 A | 7/1995 | Sum et al. |
| 5,442,059 A | 8/1995 | Sum et al. |
| 5,457,096 A | 10/1995 | Sum et al. |
| 5,466,684 A | 11/1995 | Sum et al. |
| 5,494,903 A | 2/1996 | Hlavka et al. |
| 5,495,018 A | 2/1996 | Sum et al. |
| 5,495,030 A | 2/1996 | Sum et al. |
| 5,495,031 A | 2/1996 | Sum et al. |
| 5,512,553 A | 4/1996 | Sum et al. |
| 5,529,990 A | 6/1996 | Hlavka et al. |
| 5,530,117 A | 6/1996 | Hlavka et al. |
| 5,567,692 A | 10/1996 | Sum et al. |
| 5,567,693 A | 10/1996 | Backer et al. |
| 5,589,470 A | 12/1996 | Levy |
| 5,639,742 A | 6/1997 | Lee et al. |
| 5,675,030 A | 10/1997 | Krishnan et al. |
| 5,811,412 A | 9/1998 | Levy |
| 5,834,450 A | 11/1998 | Su |
| 5,843,925 A | 12/1998 | Backer et al. |
| 5,856,315 A | 1/1999 | Backer et al. |
| 5,886,175 A | 3/1999 | Sum et al. |
| 6,256,365 B1 | 7/2001 | Lai |
| 6,500,812 B2 | 12/2002 | Nelson et al. |
| 6,506,740 B1 | 1/2003 | Ashley et al. |
| 6,617,318 B1 | 9/2003 | Nelson et al. |
| 6,624,168 B2 | 9/2003 | Nelson et al. |
| 6,642,270 B2 | 11/2003 | Nelson et al. |
| 6,683,068 B2 | 1/2004 | Nelson et al. |
| 6,756,365 B2 | 6/2004 | Levy |
| 6,818,634 B2 | 11/2004 | Nelson et al. |
| 6,818,635 B2 | 11/2004 | Nelson et al. |
| 6,833,365 B2 | 12/2004 | Levy et al. |
| 6,841,546 B2 | 1/2005 | Draper et al. |
| 6,846,939 B2 | 1/2005 | Nelson et al. |
| 6,849,615 B2 | 2/2005 | Nelson et al. |
| 6,894,036 B2 | 5/2005 | Ashley et al. |
| 6,946,453 B2 | 9/2005 | Ashley et al. |
| 7,001,918 B2 | 2/2006 | Huss et al. |
| 7,045,507 B2 | 5/2006 | Draper et al. |
| 7,056,902 B2 | 6/2006 | Nelson et al. |
| 7,067,681 B2 | 6/2006 | Nelson et al. |
| 7,094,806 B2 | 8/2006 | Nelson et al. |
| 7,202,235 B2 | 4/2007 | Levy et al. |
| 7,208,482 B2 | 4/2007 | Garcia-Luzon et al. |
| 7,323,492 B2 | 1/2008 | Huss et al. |
| 7,326,696 B2 | 2/2008 | Nelson et al. |
| 7,361,674 B2 | 4/2008 | Nelson et al. |
| 7,414,041 B2 | 8/2008 | Levy |
| 7,521,437 B2 | 4/2009 | Nelson et al. |
| 7,553,828 B2 | 6/2009 | Nelson et al. |
| 2002/0111335 A1 | 8/2002 | Nelson et al. |
| 2002/0128237 A1 | 9/2002 | Nelson et al. |
| 2002/0128238 A1 | 9/2002 | Nelson et al. |
| 2002/0160987 A1 | 10/2002 | Ashley et al. |
| 2002/0193354 A1 | 12/2002 | Nelson et al. |
| 2003/0055025 A1 | 3/2003 | Nelson et al. |
| 2003/0069721 A1 | 4/2003 | Podlogar |
| 2003/0125348 A1 | 7/2003 | Nelson et al. |
| 2003/0195174 A1 | 10/2003 | Ashley et al. |
| 2004/0002481 A1 | 1/2004 | Ashley et al. |
| 2004/0063674 A1 | 4/2004 | Levy et al. |
| 2004/0067912 A1 | 4/2004 | Hlavka et al. |
| 2004/0092490 A1 | 5/2004 | Draper et al. |
| 2004/0138183 A1 | 7/2004 | Nelson et al. |
| 2004/0176334 A1 | 9/2004 | Nelson et al. |
| 2004/0214800 A1 | 10/2004 | Levy et al. |
| 2004/0214801 A1 | 10/2004 | Nelson et al. |
| 2004/0242548 A1 | 12/2004 | Draper et al. |
| 2004/0266740 A1 | 12/2004 | Huss et al. |
| 2005/0020545 A1 | 1/2005 | Draper et al. |
| 2005/0026875 A1 | 2/2005 | Nelson et al. |
| 2005/0026876 A1 | 2/2005 | Nelson et al. |
| 2005/0038002 A1 | 2/2005 | Nelson et al. |
| 2005/0070510 A1 | 3/2005 | Draper et al. |
| 2005/0119235 A1 | 6/2005 | Nelson et al. |
| 2005/0137174 A1 | 6/2005 | Ohemeng et al. |
| 2005/0143352 A1 | 6/2005 | Nelson et al. |
| 2005/0143353 A1 | 6/2005 | Nelson et al. |
| 2005/0187198 A1 | 8/2005 | Nelson et al. |
| 2005/0215532 A1 | 9/2005 | Levy et al. |
| 2005/0245491 A9 | 11/2005 | Hlavka et al. |
| 2005/0250744 A1 | 11/2005 | Levy et al. |
| 2005/0267079 A1 | 12/2005 | Hlavka et al. |
| 2005/0282787 A1 | 12/2005 | Myers et al. |
| 2005/0288262 A1 | 12/2005 | Bandarage et al. |
| 2006/0003971 A1 | 1/2006 | Nelson |
| 2006/0084634 A1 | 4/2006 | Huss et al. |
| 2006/0089336 A1 | 4/2006 | Nelson et al. |
| 2006/0148765 A1 | 7/2006 | Nelson et al. |
| 2006/0166944 A1 | 7/2006 | Berniac et al. |
| 2006/0166945 A1 | 7/2006 | Abato et al. |
| 2006/0166946 A1 | 7/2006 | Nelson et al. |
| 2006/0194773 A1 | 8/2006 | Levy et al. |
| 2006/0205698 A1 | 9/2006 | Nelson et al. |
| 2006/0229282 A1 | 10/2006 | Nelson et al. |
| 2006/0234988 A1 | 10/2006 | Nelson et al. |
| 2006/0281717 A1 | 12/2006 | Berniac et al. |
| 2006/0287283 A1 | 12/2006 | Amoo et al. |
| 2007/0072834 A1 | 3/2007 | Nelson et al. |
| 2007/0093455 A1 | 4/2007 | Abato et al. |
| 2007/0155708 A1 | 7/2007 | Nelson et al. |
| 2007/0167415 A1 | 7/2007 | Levy et al. |
| 2007/0270389 A1 | 11/2007 | Garcia-Luzon et al. |
| 2008/0015169 A1 | 1/2008 | Nelson et al. |
| 2008/0070873 A1 | 3/2008 | Alekshun et al. |
| 2008/0118979 A1 | 5/2008 | Draper et al. |
| 2008/0167273 A1 | 7/2008 | Nelson et al. |
| 2008/0287401 A1 | 11/2008 | Johnston et al. |
| 2008/0300424 A1 | 12/2008 | Nelson et al. |
| 2008/0306032 A1 | 12/2008 | Nelson et al. |
| 2008/0312193 A1 | 12/2008 | Assefa et al. |
| 2009/0054379 A1 | 2/2009 | Huss et al. |
| 2009/0118269 A1 | 5/2009 | Berniac et al. |
| 2009/0124583 A1 | 5/2009 | Nelson et al. |
| 2009/0131696 A1 | 5/2009 | Levy |
| 2009/0156842 A1 | 6/2009 | Seyedi et al. |

FOREIGN PATENT DOCUMENTS

| | | |
|---|---|---|
| EP | 582788 A1 | 2/1994 |
| EP | 582789 A1 | 2/1994 |
| EP | 582790 A1 | 2/1994 |
| EP | 582810 A1 | 2/1994 |
| EP | 582829 A1 | 2/1994 |
| EP | 618190 A1 | 10/1994 |
| GB | 921252 A | 3/1963 |
| GB | 955766 A | 4/1964 |
| GB | 1469384 A | 4/1977 |
| JP | H11209337 A | 8/1999 |
| JP | 2002-105038 A | 4/2002 |
| WO | WO-9522529 A1 | 8/1995 |
| WO | WO-9634852 A1 | 11/1996 |
| WO | WO-00/28983 A1 | 5/2000 |
| WO | WO-0162242 A1 | 8/2001 |
| WO | WO-01/87823 A1 | 11/2001 |
| WO | WO-02/072031 A2 | 9/2002 |
| WO | WO-02072022 A2 | 9/2002 |
| WO | WO-02072532 A1 | 9/2002 |
| WO | WO-02/085303 A2 | 10/2002 |
| WO | WO-03/005971 A2 | 1/2003 |
| WO | WO-03/075857 A2 | 9/2003 |

(56) References Cited

FOREIGN PATENT DOCUMENTS

| WO | WO-2004/038000 A2 | 5/2004 |
|---|---|---|
| WO | WO-2004/038001 A2 | 5/2004 |
| WO | WO-2005082860 A1 | 9/2005 |

OTHER PUBLICATIONS

Bartzatt R. et al., "Synthesis and Analysis of a Methyl Ether Derivative of Tetracycline Which Inhibits Growth of *Escherichia Coli*," Physiol. Chem. Phys. & Med. NMR., vol. 34, pp. 71-81, 2002.

Bartzatt R. et al., "Synthesis and analysis of ethylated tetracycline, an antibiotic derivative that inhibits the growth of tetracycline-resistant XL I-Blue bacteria," Biotechnol. Appl/ Biochem., vol. 33, pp. 65-69, 2001.

Berens C. et al., "Subtype Selective Tetracycline Agonists and their Application for a Two-Stage Regulatory System," ChemBioChem, vol. 7, pp. 1320-1324, 2006.

Boothe, J. H. et al., "6-Deoxytetracyclines. I. Chemical Modification by Electrophilic Substitution," J. Am. Chem. Soc. vol. 82, pp. 1253-1254, 1960.

European Search Report for Application No. 04756012.3, dated Mar. 2, 2007, 6 pages.

Internaitonal Search Report for Application No. PCT/US2004/020249, 5 pages.

Koza D. J. et al., "Palladium Catalyzed C—N Bond Formation in the Synthesis of 7-Amino-Substituted Tetracyclines," J. Org. Chem., vol. 67, pp. 5025-5027, 2002.

Koza D. J. et al., "Synthesis and Biological Evaluation of 9-Substituted Tetracycline Derivatives," Bioorganic & Medical Chemistry Letters, vol. 12, pp. 2163-2165, 2002.

Koza, Darell J., "Synthesis of 7-Substituted Tetracycline Derivatives," Organic Letters, vol. 2, No. 6, pp. 815-817, 2000.

Koza, Darell J., "The synthesis of 8-substituted tetracycline derivatives, the first 8-position carbon-carbon bond," Tetrahedron Letters, vol. 41, pp. 5017-5020, 2000.

Martell M. J. et al., "The 6-Deoxytetracyclines. IX. Imidomethylation," J. Med. Chem., vol. 10, No. 3, pp. 359-363, 1967.

Martell M. J. et al., "The 6-Deoxytetracyclines. VII. Alkylated Aminotetracyclines Posessing Unique Antibacterial Activity," J. Med. Chem., vol. 10, pp. 44-46, 1967.

Nelson M. L. et al., "Versatile and Facile Synthesis of Diverse Semisynthetic Tetracycline Derivatives via Pd-Catalyzed Reactions," J. Org. Chem., vol. 68, pp. 5838-5851, 2003.

Paemen L. et al., "The Gelatinase Inhibitory Activity of Tetracyclines and Chemically Modified Tetracycline Analogues as Measured by a Novel Microtiter Assay for Inhibitors," Biochemical Pharmacology, vol. 52, pp. 105-111, 1996.

Petersen P. J. et al., "In Vitro and In Vitro Antibacterial Activities of a Novel Glycylcycline, the 9-t-Butylglycylamido Derivative of Minocycline (GAR-936)," Antimicrobial Agents and Chemotherapy, pp. 734-744, 1999.

Spencer J. L. et al., "6-Deoxytetracyclines. $V^{1a}$ 7,9-Disubstituted Products," J. Med. Chem., vol. 122, pp. 405-407, 1963.

Sum P-E. et al., "Glycylclines. 1. A New Generation of Potent Antibacterial Agents through Modification of 9-Aminotetracyclines," J. Med. Chem., vol. 37, 184-188, 1994.

Sum P-E. et al., "Synthesis and antibacterial activity of 9-substituted minocycline derivatives," Bioorganic & Medical Chemistry Letters, vol. 16, pp. 400-403, 2006.

Sum P-E. et al., "Synthesis and Structure-Activity Relationship of Novel Glycylcline Derivatives Leading to the Discovery of GAR-936," Bioorganic & Medical Chemistry Letters, vol. 9, pp. 1459-1462, 1999.

Sum, P-E. et al., "Recent Developments in Tetracycline Antibiotics," Curr. Pharm. Des., vol. 2, pp. 119-132, 1998.

Tally F. T. et al., "Journal of Antimicrobial Chemotherapy," vol. 35, pp. 449-452, 1995.

SUBSTITUTED TETRACYCLINE COMPOUNDS

RELATED APPLICATIONS

This application is a continuation of U.S. patent application Ser. No. 10/877,928, filed on Jun. 25, 2004, which claims the benefit of U.S. Provisional Patent Application No. 60/486,017, filed on Jul. 9, 2003; U.S. Provisional Patent Application 60/525,287, filed Nov. 25, 2003; and U.S. Provisional Patent Application 60/530,123, filed Dec. 16, 2003. The entire contents of each of these aforementioned applications are hereby incorporated herein by reference.

BACKGROUND OF THE INVENTION

The development of the tetracycline antibiotics was the direct result of a systematic screening of soil specimens collected from many parts of the world for evidence of microorganisms capable of producing bacteriocidal and/or bacteriostatic compositions. The first of these novel compounds was introduced in 1948 under the name chlortetracycline. Two years later, oxytetracycline became available. The elucidation of the chemical structure of these compounds confirmed their similarity and furnished the analytical basis for the production of a third member of this group in 1952, tetracycline. A new family of tetracycline compounds, without the ring-attached methyl group present in earlier tetracyclines, was prepared in 1957 and became publicly available in 1967; and minocycline was in use by 1972.

Recently, research efforts have focused on developing new tetracycline antibiotic compositions effective under varying therapeutic conditions and routes of administration. New tetracycline analogues have also been investigated which may prove to be equal to or more effective than the originally introduced tetracycline compounds. Examples include U.S. Pat. Nos. 2,980,584; 2,990,331; 3,062,717; 3,165,531; 3,454,697; 3,557,280; 3,674,859; 3,957,980; 4,018,889; 4,024,272; and 4,126,680. These patents are representative of the range of pharmaceutically active tetracycline and tetracycline analogue compositions.

Historically, soon after their initial development and introduction, the tetracyclines were found to be highly effective pharmacologically against rickettsiae; a number of gram-positive and gram-negative bacteria; and the agents responsible for lymphogranuloma venereum, inclusion conjunctivitis, and psittacosis. Hence, tetracyclines became known as "broad spectrum" antibiotics. With the subsequent establishment of their in vitro antimicrobial activity, effectiveness in experimental infections, and pharmacological properties, the tetracyclines as a class rapidly became widely used for therapeutic purposes. However, this widespread use of tetracyclines for both major and minor illnesses and diseases led directly to the emergence of resistance to these antibiotics even among highly susceptible bacterial species both commensal and pathogenic (e.g., pneumococci and Salmonella). The rise of tetracycline-resistant organisms has resulted in a general decline in use of tetracyclines and tetracycline analogue compositions as antibiotics of choice.

SUMMARY OF THE INVENTION

In one embodiment, the invention pertains to a 7,9-substituted tetracycline compound of Formula I:

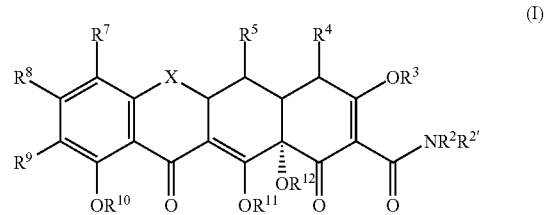

wherein:

$X$ is $CHC(R^{13}Y'Y)$, $CR^{6'}R^6$, $S$, $NR^6$, or $O$;

$R^2$, $R^{2'}$, $R^{4'}$, and $R^{4''}$ are each independently hydrogen, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;

$R^4$ is $NR^{4'}R^{4''}$, alkyl, alkenyl, alkynyl, hydroxyl, halogen, or hydrogen;

$R^{2'}$, $R^3$, $R^{10}$, $R^{11}$ and $R^{12}$ are each hydrogen or a pro-drug moiety;

$R^5$ is hydroxyl, hydrogen, thiol, alkanoyl, aroyl, alkaroyl, aryl, heteroaromatic, alkyl, alkenyl, alkynyl, alkoxy, alkylthio, alkylsulfinyl, alkylsulfonyl, alkylamino, arylalkyl, alkyl carbonyloxy, or aryl carbonyloxy;

$R^6$ and $R^{6'}$ are each independently hydrogen, methylene, absent, hydroxyl, halogen, thiol, alkyl, alkenyl, alkynyl, aryl, alkoxy, alkylthio, alkylsulfinyl, alkylsulfonyl, alkylamino, or an arylalkyl;

$R^7$ ethyl, perhalogenated alkenyl, substituted pyridinyl, pyrazinyl, furanyl, or pyrazolyl;

$R^8$ is hydrogen, hydroxyl, halogen, thiol, alkyl, alkenyl, alkynyl, aryl, alkoxy, alkylthio, alkylsulfinyl, alkylsulfonyl, alkylamino, or an arylalkyl;

$R^9$ —$CH_2NR^{9a}R^{9b}$;

$R^{9a}$ and $R^{9b}$ are each independently hydrogen, alkyl, alkenyl or linked to form a heterocycle;

$R^{13}$ is hydrogen, hydroxy, alkyl, alkenyl, alkynyl, alkoxy, alkylthio, alkylsulfinyl, alkylsulfonyl, alkylamino, or an arylalkyl; and $Y'$ and $Y$ are each independently hydrogen, halogen, hydroxyl, cyano, sulfhydryl, amino, alkyl, alkenyl, alkynyl, alkoxy, alkylthio, alkylsulfinyl, alkylsulfonyl, alkylamino, or an arylalkyl, and pharmaceutically acceptable salts thereof.

In another embodiment, the invention pertains to a 9-substituted tetracycline compound of formula II:

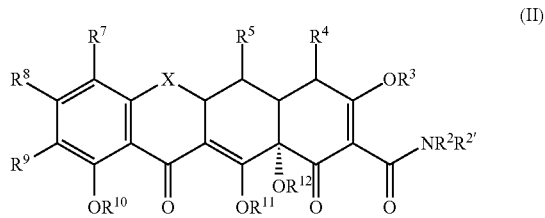

wherein:

X is CHC(R$^{13}$Y'Y), CR$^{6'}$R$^6$, S, NR$^6$, or O;

R$^2$, R$^{4'}$, R$^{4''}$, R$^{7'}$ and R$^{7''}$ are each hydrogen, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;

R$^4$ is NR$^4$R$^{4''}$, alkyl, alkenyl, alkynyl, aryl, hydroxyl, halogen, or hydrogen;

R$^{2'}$, R$^3$, R$^{10}$, R$^{11}$ and R$^{12}$ are each hydrogen or a pro-drug moiety;

R$^5$ is hydroxyl, hydrogen, thiol, alkanoyl, aroyl, alkaroyl, aryl, heteroaromatic, alkyl, alkenyl, alkynyl, alkoxy, alkylthio, alkylsulfinyl, alkylsulfonyl, alkylamino, arylalkyl, alkyl carbonyloxy, or aryl carbonyloxy;

R$^6$ and R$^{6'}$ are independently hydrogen, methylene, absent, hydroxyl, halogen, thiol, alkyl, alkenyl, alkynyl, aryl, alkoxy, alkylthio, alkylsulfinyl, alkylsulfonyl, alkylamino, or an arylalkyl;

R$^7$ is NR$^7$R$^{7''}$, alkyl, alkenyl, alkynyl, aryl, hydroxyl, halogen, or hydrogen; R$^8$ is hydrogen, hydroxyl, halogen, thiol, alkyl, alkenyl, alkynyl, aryl, alkoxy, alkylthio, alkylsulfinyl, alkylsulfonyl, alkylamino, or an arylalkyl;

R$^9$ is —CH$_2$NR$^{9a}$R$^{9b}$, or linked with R$^{10}$ to form a furanyl ring;

R$^{9a}$ is hydrogen, alkyl, alkenyl, alkynyl, alkoxy, alkylthio, alkylsulfinyl, alkylsulfonyl, alkylamino, arylalkyl, aryl, heterocyclic, or heteroaromatic;

R$^{9b}$ is hydrogen or alkyl;

R$^8$ is hydrogen, hydroxyl, halogen, thiol, alkyl, alkenyl, alkynyl, aryl, alkoxy, alkylthio, alkylsulfinyl, alkylsulfonyl, alkylamino, or an arylalkyl;

R$^{13}$ is hydrogen, hydroxy, alkyl, alkenyl, alkynyl, alkoxy, alkylthio, alkylsulfinyl, alkylsulfonyl, alkylamino, or an arylalkyl;

Y' and Y are each independently hydrogen, halogen, hydroxyl, cyano, sulfhydryl, amino, alkyl, alkenyl, alkynyl, alkoxy, alkylthio, alkylsulfinyl, alkylsulfonyl, alkylamino, or an arylalkyl, and pharmaceutically acceptable salts, esters and prodrugs thereof.

In another embodiment, the invention pertains to 7-substituted tetracycline compounds of formula III:

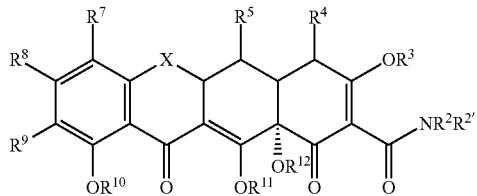

(III)

wherein:

X is CHC(R$^{13}$Y'Y), CR$^{6'}$R$^6$, C=CR$^{6'}$R$^6$, S, NR$^6$, or O;

R$^2$, R$^{2'}$, R$^{4'}$, and R$^{4''}$ are each independently hydrogen, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;

R$^4$ is NR$^4$R$^{4''}$, alkyl, alkenyl, alkynyl, aryl, hydroxyl, halogen, or hydrogen;

R$^{2'}$, R$^3$, R$^{10}$, R$^{11}$ and R$^{12}$ are each hydrogen or a pro-drug moiety;

R$^5$ is hydroxyl, hydrogen, thiol, alkanoyl, aroyl, alkaroyl, aryl, heteroaromatic, alkyl, alkenyl, alkynyl, alkoxy, alkylthio, alkylsulfinyl, alkylsulfonyl, alkylamino, arylalkyl, alkyl carbonyloxy, or aryl carbonyloxy;

R$^6$ and R$^{6'}$ are each independently hydrogen, methylene, absent, hydroxyl, halogen, thiol, alkyl, alkenyl, alkynyl, aryl, alkoxy, alkylthio, alkylsulfinyl, alkylsulfonyl, alkylamino, or an arylalkyl;

R$^7$ is substituted or unsubstituted pyrazolyl, furanyl, thiophenyl, or thiazolyl;

R$^8$ is hydrogen, hydroxyl, halogen, thiol, alkyl, alkenyl, alkynyl, aryl, alkoxy, alkylthio, alkylsulfinyl, alkylsulfonyl, alkylamino, or an arylalkyl;

R$^9$ is hydrogen;

R$^{13}$ is hydrogen, hydroxy, alkyl, alkenyl, alkynyl, alkoxy, alkylthio, alkylsulfinyl, alkylsulfonyl, alkylamino, or an arylalkyl; and Y' and Y are each independently hydrogen, halogen, hydroxyl, cyano, sulfhydryl, amino, alkyl, alkenyl, alkynyl, alkoxy, alkylthio, alkylsulfinyl, alkylsulfonyl, alkylamino, or an arylalkyl, and pharmaceutically acceptable salts thereof.

In another embodiment, the invention pertains to 8-substituted tetracycline compound of formula IV:

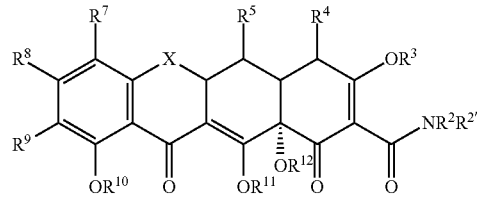

(IV)

wherein:

X is CHC(R$^{13}$Y'Y), CR$^{6'}$R$^6$, S, NR$^6$, or O;

R$^2$, R$^{4'}$, R$^{4''}$, R$^{7'}$ and R$^{7''}$ are each hydrogen, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;

R$^4$ is NR$^4$R$^{4''}$, alkyl, alkenyl, alkynyl, aryl, hydroxyl, halogen, or hydrogen;

R$^{2'}$, R$^3$, R$^{10}$, R$^{11}$ and R$^{12}$ are each hydrogen or a pro-drug moiety;

R$^5$ is hydroxyl, hydrogen, thiol, alkanoyl, aroyl, alkaroyl, aryl, heteroaromatic, alkyl, alkenyl, alkynyl, alkoxy, alkylthio, alkylsulfinyl, alkylsulfonyl, alkylamino, arylalkyl, alkyl carbonyloxy, or aryl carbonyloxy;

R$^6$ and R$^{6'}$ are independently hydrogen, methylene, absent, hydroxyl, halogen, thiol, alkyl, alkenyl, alkynyl, aryl, alkoxy, alkylthio, alkylsulfinyl, alkylsulfonyl, alkylamino, or an arylalkyl;

R$^7$ is hydrogen, hydroxyl, halogen, thiol, nitro, alkyl, alkenyl, alkynyl, aryl, alkoxy, alkylthio, alkylsulfinyl, alkylsulfonyl, arylalkyl, amino, arylalkenyl, arylalkynyl, acyl, aminoalkyl, heterocyclic, thionitroso, or —(CH$_2$)$_{0-3}$(NR$^{7c}$)$_{0-1}$C(=W')WR$^{7a}$;

R$^8$ is an aminomethyl substituted phenyl or substituted pyridinyl;

R$^9$ is hydrogen, hydroxyl, halogen, thiol, nitro, alkyl, alkenyl, alkynyl, aryl, alkoxy, alkylthio, alkylsulfinyl, alkylsulfonyl, arylalkyl, amino, arylalkenyl, arylalkynyl, acyl, aminoalkyl, heterocyclic, thionitroso, or —(CH$_2$)$_{0-3}$NR$^{9c}$C(=Z')ZR$^{9a}$;

R$^{7a}$, R$^{7b}$, R$^{7c}$, R$^{7d}$, R$^{7e}$, R$^{7f}$, R$^{9a}$, R$^{9b}$, R$^{9c}$, R$^{9d}$, R$^{9e}$, and R$^{8f}$ are each independently absent, hydrogen, acyl, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;

W is $CR^{7d}R^{7e}$, S, O or $NR^{7b}$;
W' is O, $NR^{7f}$, or S;
Z is $CR^{9d}R^{9e}$, S, O or $NR^{9b}$;
Z' is O, $NR^{9f}$, or S;
$R^{13}$ is hydrogen, hydroxy, alkyl, alkenyl, alkynyl, alkoxy, alkylthio, alkylsulfinyl, alkylsulfonyl, alkylamino, or an arylalkyl;
Y' and Y are each independently hydrogen, halogen, hydroxyl, cyano, sulfhydryl, amino, alkyl, alkenyl, alkynyl, alkoxy, alkylthio, alkylsulfinyl, alkylsulfonyl, alkylamino, or an arylalkyl, and pharmaceutically acceptable salts, esters and prodrugs thereof.

In one embodiment, a 13-substituted tetracycline compound is of formula V:

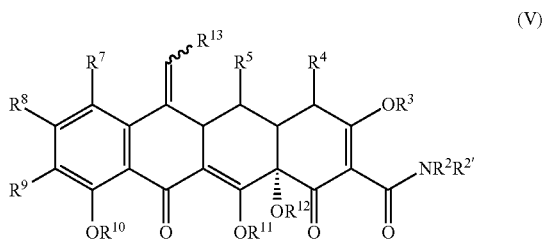

(V)

wherein:
$R^2$, $R^{4'}$, $R^{4''}$, $R^{7'}$ and $R^{7''}$ are each hydrogen, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;
$R^4$ is $NR^{4'}R^{4''}$, alkyl, alkenyl, alkynyl, aryl, hydroxyl, halogen, or hydrogen;
$R^{2'}$, $R^3$, $R^{10}$, $R^{11}$ and $R^{12}$ are each hydrogen or a pro-drug moiety;
$R^5$ is hydroxyl, hydrogen, thiol, alkanoyl, aroyl, alkaroyl, aryl, heteroaromatic, alkyl, alkenyl, alkynyl, alkoxy, alkylthio, alkylsulfinyl, alkylsulfonyl, alkylamino, arylalkyl, alkyl carbonyloxy, or aryl carbonyloxy;
$R^7$ is hydrogen, hydroxyl, halogen, thiol, nitro, alkyl, alkenyl, alkynyl, aryl, alkoxy, alkylthio, alkylsulfinyl, alkylsulfonyl, arylalkyl, amino, arylalkenyl, arylalkynyl, acyl, aminoalkyl, heterocyclic, thionitroso, or —$(CH_2)_{0-3}(NR^{7c})_{0-1}C(=W')WR^{7a}$;
$R^8$ is substituted phenyl or substituted pyridinyl;
$R^9$ is hydrogen, hydroxyl, halogen, thiol, nitro, alkyl, alkenyl, alkynyl, aryl, alkoxy, alkylthio, alkylsulfinyl, alkylsulfonyl, arylalkyl, amino, arylalkenyl, arylalkynyl, acyl, aminoalkyl, heterocyclic, thionitroso, or —$(CH_2)_{0-3}NR^{9c}C(=Z')ZR^{9a}$;
$R^{7a}$, $R^{7b}$, $R^{7c}$, $R^{7d}$, $R^{7e}$, $R^{7f}$, $R^{9a}$, $R^{9b}$, $R^{9c}$, $R^{9d}$, $R^{9e}$, and $R^{8f}$ are each independently absent, hydrogen, acyl, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;
W is $CR^{7d}R^{7e}$, S, O or $NR^{7b}$;
W' is O, $NR^{7f}$, or S;
$R^{13}$ is 4-alkyl substituted phenyl, and pharmaceutically acceptable salts, esters and prodrugs thereof.

In another further embodiment, the invention pertains, at least in part, to methods for treating subjects for tetracycline responsive states by administering to them an effective amount of a tetracycline compound of the invention, e.g., a compound of formula I, II, III, IV, V, or a tetracycline compound otherwise described herein.

DETAILED DESCRIPTION OF THE INVENTION

The present invention pertains, at least in part, to novel substituted tetracycline compounds. These tetracycline compounds can be used to treat numerous tetracycline compound-responsive states, such as bacterial infections and neoplasms, as well as other known applications for minocycline and tetracycline compounds in general, such as blocking tetracycline efflux and modulation of gene expression.

The term "tetracycline compound" includes many compounds with a similar ring structure to tetracycline. Examples of tetracycline compounds include: chlortetracycline, oxytetracycline, demeclocycline, methacycline, sancycline, chelocardin, rolitetracycline, lymecycline, apicycline; clomocycline, guamecycline, meglucycline, mepylcycline, penimepicycline, pipacycline, etamocycline, penimocycline, etc. Other derivatives and analogues comprising a similar four ring structure are also included (See Rogalski, "Chemical Modifications of Tetracyclines," the entire contents of which are hereby incorporated herein by reference). Table 1 depicts tetracycline and several known other tetracycline derivatives.

TABLE 1

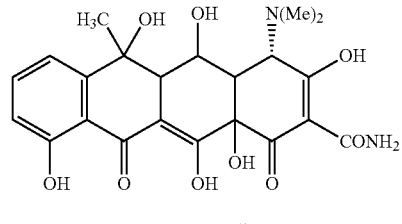

Oxytetracycline

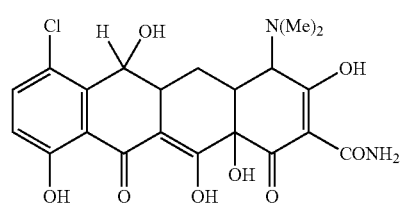

Demeclocycline

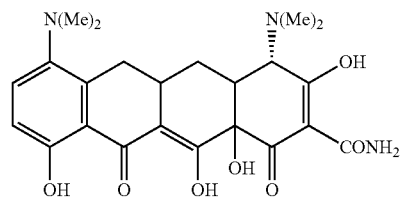

Minocycline

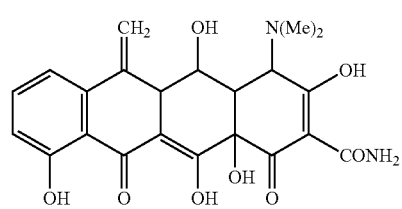

Methacycline

TABLE 1-continued

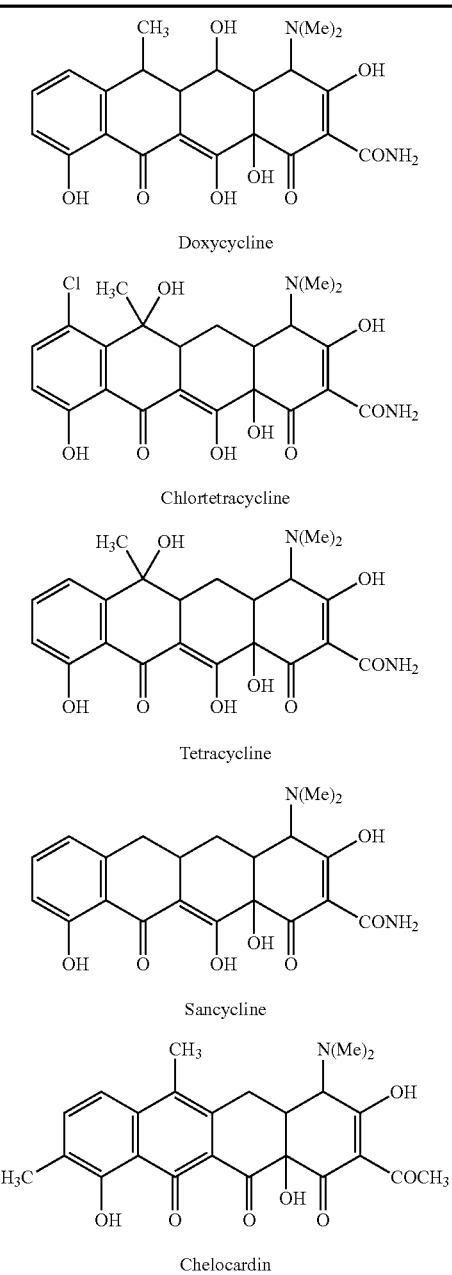

Doxycycline

Chlortetracycline

Tetracycline

Sancycline

Chelocardin

Other tetracycline compounds which may be modified using the methods of the invention include, but are not limited to, 6-demethyl-6-deoxy-4-dedimethylaminotetracycline; tetracyclino-pyrazole; 7-chloro-4-dedimethylamino-tetracycline; 4-hydroxy-4-dedimethylaminotetracycline; 12α deoxy-4-dedimethylaminotetracycline; 5-hydroxy-6α-deoxy-4-dedimethylaminotetracycline; 4-dedimethylamino-12α-deoxyanhydrotetracycline; 7-dimethylamino-6-demethyl-6-deoxy-4-dedimethylaminotetracycline; tetracyclinonitrile; 4-oxo-4-dedimethylaminotetracycline 4,6-hemiketal; 4-oxo-11a C1-4-dedimethylaminotetracycline-4,6-hemiketal; 5a,6-anhydro-4-hydrazon-4-dedimethylamino tetracycline; 4-hydroxyimino-4-dedimethylamino tetracyclines; 4-hydroxyimino-4-dedimethylamino 5a,6-anhydrotetracyclines; 4-amino-4-dedimethylamino-5a, 6 anhydrotetracycline; 4-methylamino-4-dedimethylamino tetracycline; 4-hydrazono-11a-chloro-6-deoxy-6-demethyl-6-methylene-4-dedimethylamino tetracycline; tetracycline quaternary ammonium compounds; anhydrotetracycline betaines; 4-hydroxy-6-methyl pretetramides; 4-keto tetracyclines; 5-keto tetracyclines; 5a, 11a dehydro tetracyclines; 11a C1-6, 12 hemiketal tetracyclines; 11a C1-6-methylene tetracyclines; 6, 13 diol tetracyclines; 6-benzylthiomethylene tetracyclines; 7,11a-dichloro-6-fluoro-methyl-6-deoxy tetracyclines; 6-fluoro (α)-6-demethyl-6-deoxy tetracyclines; 6-fluoro (β)-6-demethyl-6-deoxy tetracyclines; 6-α acetoxy-6-demethyl tetracyclines; 6-β acetoxy-6-demethyl tetracyclines; 7,13-epithiotetracyclines; oxytetracyclines; pyrazolotetracyclines; 11a halogens of tetracyclines; 12a formyl and other esters of tetracyclines; 5,12a esters of tetracyclines; 10,12a-diesters of tetracyclines; isotetracycline; 12-a-deoxyanhydro tetracyclines; 6-demethyl-12a-deoxy-7-chloroanhydrotetracyclines; B-nortetracyclines; 7-methoxy-6-demethyl-6-deoxytetracyclines; 6-demethyl-6-deoxy-5a-epitetracyclines; 8-hydroxy-6-demethyl-6-deoxy tetracyclines; monardene; chromocycline; 5a methyl-6-demethyl-6-deoxy tetracyclines; 6-oxa tetracyclines, and 6 thia tetracyclines.

1. 7,9-Substituted Tetracycline Compounds

The invention also pertains, at least in part to 7,9-substituted tetracycline compounds.

The term "7,9-substituted tetracycline compounds" includes tetracycline compounds with substitution at the 7 and 9-positions. In one embodiment, the substitution at the 7- and 9-positions enhances the ability of the tetracycline compound to perform its intended function, e.g., treat tetracycline responsive states. In an embodiment, the 7,9-substituted tetracycline compound is 7,9-substituted tetracycline (e.g., wherein $R^4$ is $NR^{4'}R^{4''}$; $R^{4'}$ and $R^{4''}$ are methyl, $R^5$ is hydrogen and X is $CR^6R^{6'}$, wherein $R^6$ is methyl and $R^{6'}$ is hydroxy); 7,9-substituted doxycycline (e.g., wherein $R^4$ is $NR^{4'}R^{4''}$; $R^{4'}$ and $R^{4''}$ are methyl, $R^5$ is hydroxyl and X is $CR^6R^{6'}$, wherein $R^6$ is methyl and $R^{6'}$ is hydrogen); or 7,9-substituted sancycline (wherein $R^4$ is $NR^{4'}R^{4''}$; $R^{4'}$ and $R^{4''}$ are methyl; $R^5$ is hydrogen and X is $CR^6R^{6'}$ wherein $R^6$ and $R^{6'}$ are hydrogen atoms. In an embodiment, the substitution at the 7 position of the 7,9-substituted tetracycline compound is not chlorine or trimethylamino. In one embodiment, $R^4$ is hydrogen.

In one embodiment, the invention pertains to 7,9-substituted tetracycline compounds of Formula I:

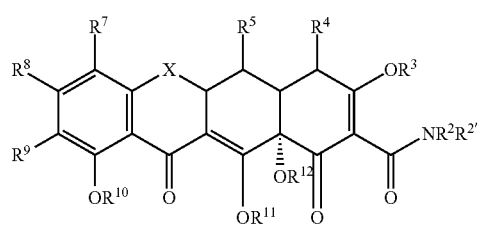

(I)

wherein:

X is $CHC(R^{13}Y'Y)$, $CR^6R^6$, S, $NR^6$, or O;

$R^2$, $R^{2'}$, $R^{4'}$, and $R^{4''}$ are each independently hydrogen, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;

$R^4$ is $NR^{4'}R^{4''}$, alkyl, alkenyl, alkynyl, hydroxyl, halogen, or hydrogen;

$R^{2'}$, $R^3$, $R^{10}$, $R^{11}$ and $R^{12}$ are each hydrogen or a pro-drug moiety;

$R^5$ is hydroxyl, hydrogen, thiol, alkanoyl, aroyl, alkaroyl, aryl, heteroaromatic, alkyl, alkenyl, alkynyl, alkoxy, alkylthio, alkylsulfinyl, alkylsulfonyl, alkylamino, arylalkyl, alkyl carbonyloxy, or aryl carbonyloxy;

$R^6$ and $R^{6'}$ are each independently hydrogen, methylene, absent, hydroxyl, halogen, thiol, alkyl, alkenyl, alkynyl, aryl, alkoxy, alkylthio, alkylsulfinyl, alkylsulfonyl, alkylamino, or an arylalkyl;

$R^7$ is ethyl, perhalogenated alkenyl, substituted pyridinyl, pyrazinyl, furanyl, or pyrazolyl;

$R^8$ is hydrogen, hydroxyl, halogen, thiol, alkyl, alkenyl, alkynyl, aryl, alkoxy, alkylthio, alkylsulfinyl, alkylsulfonyl, alkylamino, or an arylalkyl;

$R^9$ is $-CH_2NR^{9a}R^{9b}$;

$R^{9a}$ and $R^{9b}$ are each independently hydrogen, alkyl, alkenyl or linked to form a heterocycle;

$R^{13}$ is hydrogen, hydroxy, alkyl, alkenyl, alkynyl, alkoxy, alkylthio, alkylsulfinyl, alkylsulfonyl, alkylamino, or an arylalkyl; and Y' and Y are each independently hydrogen, halogen, hydroxyl, cyano, sulfhydryl, amino, alkyl, alkenyl, alkynyl, alkoxy, alkylthio, alkylsulfinyl, alkylsulfonyl, alkylamino, or an arylalkyl, and pharmaceutically acceptable salts thereof, provided that $R^7$ and $R^9$ are not both unsubstituted phenyl.

In a further embodiment, X is $CR^6R^{6'}$; $R^2$, $R^{2'}$, $R^6$, $R^{6'}$, $R^8$, $R^{11}$, $R^{11}$, and $R^{12}$ are each hydrogen; $R^4$ is $NR^{4'}R^{4''}$; $R^{4'}$ and $R^{4''}$ are lower alkyl; and $R^5$ is hydroxy or hydrogen. In another further embodiment, $R^{4'}$ and $R^{4''}$ are each methyl and $R^5$ is hydrogen.

In an embodiment, $R^7$ is ethyl and $R^{9a}$ is alkyl and $R^{9b}$ is alkenyl. In another embodiment, $R^7$ is substituted pyrazinyl Examples of possible substituents include halogens, such as fluorine. In another embodiment, $R^{9a}$ is alkyl and $R^{9b}$ is alkenyl. In another further embodiment, $R^{9a}$ and $R^{9b}$ are linked to form a heterocycle. In a further embodiment, the linked heterocycle is substituted piperidinyl. In a further embodiment, the piperdinyl is substituted with one or more fluorines or halogenated alkyl groups, e.g., at the 2, 3, 4, or 5 position. In another embodiment, the $R^9$ moiety is (4'trifluoromethyl-piperdin-1-yl) methyl, (4',4'-difluoro-piperdin-1-yl) methyl, or (4'-fluoropiperdin-1-yl) methyl.

In another embodiment, $R^{9a}$ is hydrogen and $R^{9b}$ is alkyl. Other examples of compounds include those wherein $R^7$ is furanyl, and $R^{9a}$ is hydrogen or alkyl and $R^{9b}$ is alkenyl, e.g., 1,2,2-trifluoroethenyl.

In another embodiment, $R^{9a}$ is hydrogen or alkyl and $R^{9b}$ is alkenyl. In another embodiment, $R^7$ is pyrazolyl and $R^{9a}$ is hydrogen or alkyl and $R^{9b}$ is alkenyl or alkyl.

In a further embodiment, the invention pertains to tetracycline compounds selected from the group consisting of:

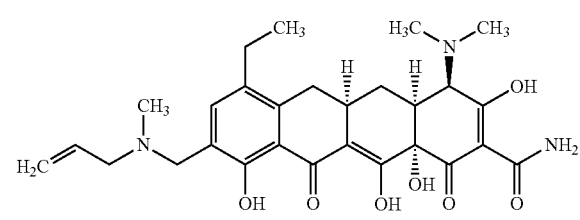

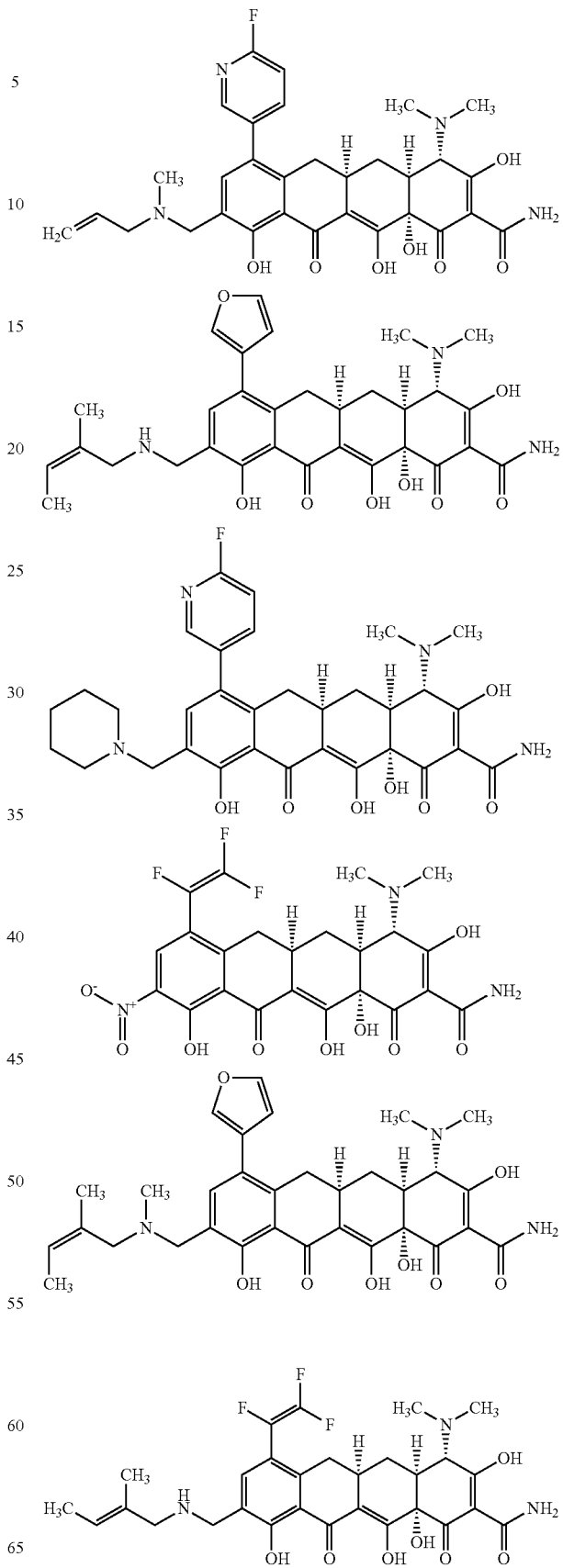

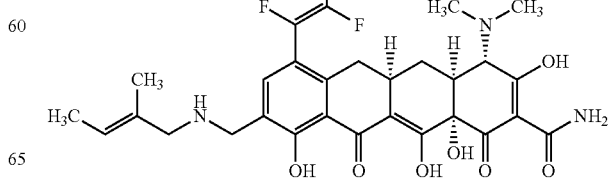

-continued
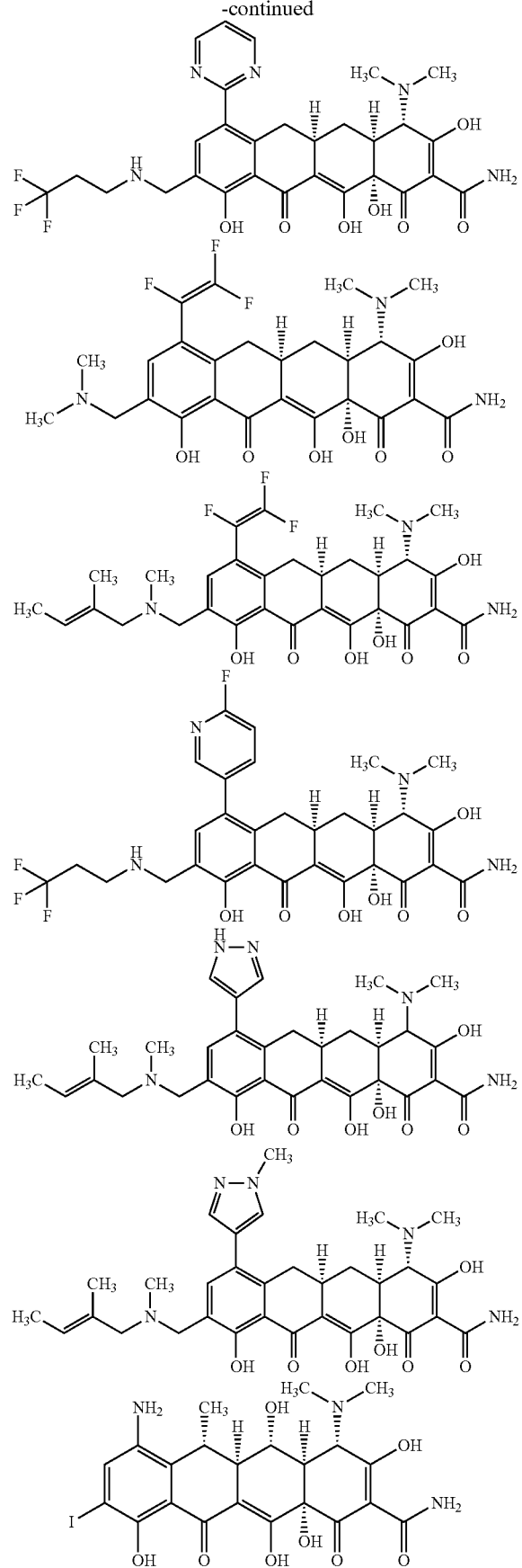
-continued
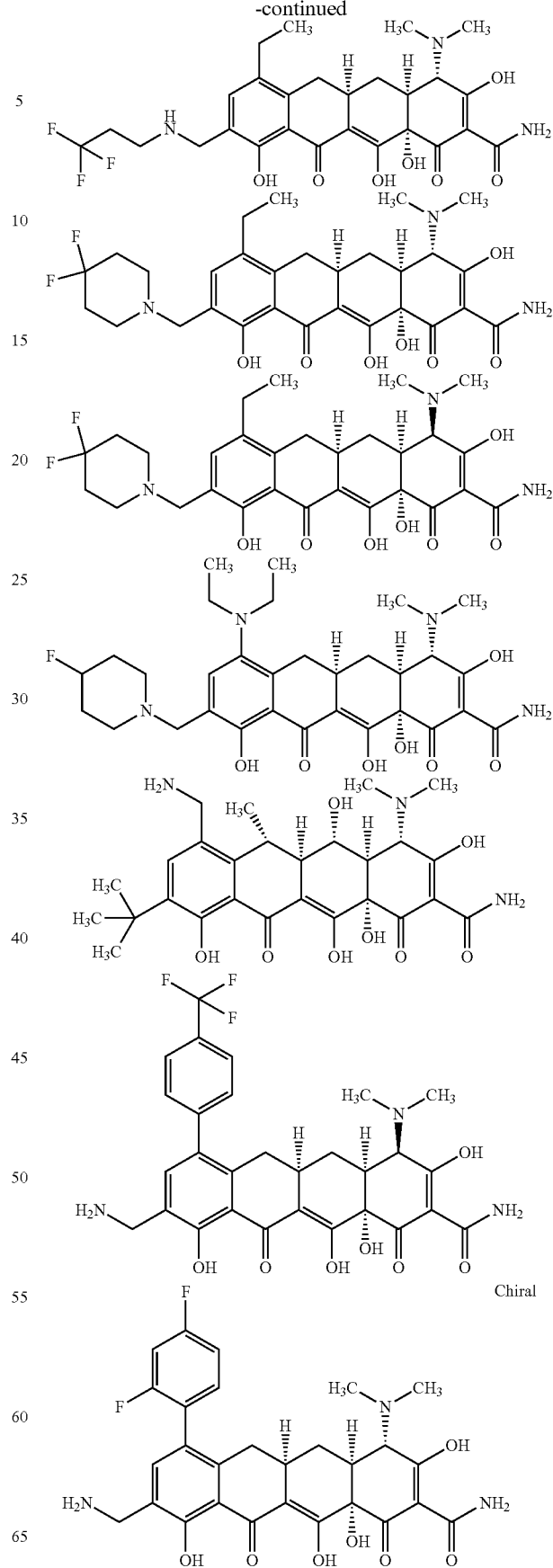

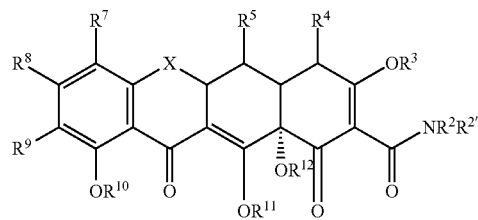

and pharmaceutically acceptable salts, esters, and prodrugs thereof.

2. 9-Substituted Tetracycline Compounds

In another embodiment, the invention pertains to 9-substituted tetracycline compounds.

The term "9-substituted tetracycline compounds" includes tetracycline compounds with substitution at the 9 position. In one embodiment, the substitution at the 9-position enhances the ability of the tetracycline compound to perform its intended function, e.g., treat tetracycline responsive states. In an embodiment, the 9-substituted tetracycline compound is 9-substituted tetracycline (e.g., wherein $R^4$ is $NR^{4'}R^{4''}$, $R^{4'}$ and $R^{4''}$ are methyl, $R^5$ is hydrogen and X is $CR^6R^{6'}$, wherein $R^6$ is methyl and $R^{6'}$ is ihydroxy, and $R^7$ is hydrogen); 9-substituted doxycycline (e.g., wherein $R^4$ is $NR^{4'}R^{4''}$, $R^{4'}R^{4'}$ and $R^{4''}$ are methyl, $R^5$ is hydroxyl and X is $CR^6R^{6'}$, wherein $R^6$ is methyl and $R^{6'}$ is hydrogen, and $R^7$ is hydrogen); 9-substituted minocycline (wherein $R^4$ is $NR^{4'}R^{4''}$, $R^{4'}$ and $R^{4''}$ are methyl; $R^5$ is hydrogen and X is $CR^6R^{6'}$ wherein $R^6$ and $R^{6'}$ are hydrogen atoms, and $R^7$ is dimethylamino); 9-substituted 4-dedimethylamino tetracycline compound, wherein X is $CR^6R^{6'}$, $R^4$, $R^5$, $R^6$, $R^{6'}$, and $R^7$ are hydrogen; and 9-substituted sancycline (wherein $R^4$ is $NR^{4'}R^{4''}$, $R^{4'}$ and $R^{4''}$ are methyl; $R^5$ and $R^7$ are hydrogen and X is $CR^6R^{6'}$ wherein $R^6$ and $R^{6'}$ are hydrogen atoms).

In another embodiment, the invention pertains to tetracycline compounds of formula II:

(II)

wherein:

X is $CHC(R^{13}Y'Y)$, $CR^6R^{6'}$, S, $NR^6$, or O;

$R^2$, $R^{4'}$, $R^{4''}$, $R^{7'}$ and $R^{7''}$ are each hydrogen, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;

$R^4$ is $NR^{4'}R^{4''}$, alkyl, alkenyl, alkynyl, aryl, hydroxyl, halogen, or hydrogen;

$R^{2'}$, $R^3$, $R^{10}$, $R^{11}$ and $R^{12}$ are each hydrogen or a pro-drug moiety;

$R^5$ is hydroxyl, hydrogen, thiol, alkanoyl, aroyl, alkaroyl, aryl, heteroaromatic, alkyl, alkenyl, alkynyl, alkoxy, alkylthio, alkylsulfinyl, alkylsulfonyl, alkylamino, arylalkyl, alkyl carbonyloxy, or aryl carbonyloxy;

$R^6$ and $R^{6'}$ are independently hydrogen, methylene, absent, hydroxyl, halogen, thiol, alkyl, alkenyl, alkynyl, aryl, alkoxy, alkylthio, alkylsulfinyl, alkylsulfonyl, alkylamino, or an arylalkyl;

$R^7$ is $NR^{7'}R^{7''}$, alkyl, alkenyl, alkynyl, aryl, hydroxyl, halogen, or hydrogen;

$R^8$ is hydrogen, hydroxyl, halogen, thiol, alkyl, alkenyl, alkynyl, aryl, alkoxy, alkylthio, alkylsulfinyl, alkylsulfonyl, alkylamino, or an arylalkyl;

$R^9$ is —$CH_2NR^{9a}R^{9b}$, or linked with $R^{10}$ to form a furanyl ring;

$R^{9a}$ is hydrogen, alkyl, alkenyl, alkynyl, alkoxy, alkylthio, alkylsulfinyl, alkylsulfonyl, alkylamino, arylalkyl, aryl, heterocyclic, or heteroaromatic;

$R^{9b}$ is alkoxycarbonyl, arylaminocarbonyl, or aryloxycarbonyl;

$R^8$ is hydrogen, hydroxyl, halogen, thiol, alkyl, alkenyl, alkynyl, aryl, alkoxy, alkylthio, alkylsulfinyl, alkylsulfonyl, alkylamino, or an arylalkyl;

$R^{13}$ is hydrogen, hydroxy, alkyl, alkenyl, alkynyl, alkoxy, alkylthio, alkylsulfinyl, alkylsulfonyl, alkylamino, or an arylalkyl;

Y' and Y are each independently hydrogen, halogen, hydroxyl, cyano, sulfhydryl, amino, alkyl, alkenyl, alkynyl, alkoxy, alkylthio, alkylsulfinyl, alkylsulfonyl, alkylamino, or an arylalkyl, and pharmaceutically acceptable salts, esters and prodrugs thereof.

In a further embodiment, $R^4$ is $NR^{4'}R^{4''}$; X is —$CR^6R^{6'}$; $R^7$ is $NR^{7'}R^{7''}$, $R^2$, $R^{2'}$, $R^5$, $R^6$, $R^{6'}$, $R^8$, $R^9$, $R^{10}$, $R^{11}$, and $R^{12}$ are each hydrogen; and, $R^{4'}$, $R^{4''}$, $R^{7'}$, and $R^{7''}$ are each lower alkyl. In another embodiment, $R^{9a}$ is alkyl, alkenyl, or arylalkyl. Examples of $R^{9b}$ include alkoxycarbonyl, alkaminocarbonyl, aryloxycarbonyl, and arylaminocarbonyl. In another embodiment, $R^{9a}$ and $R^{9b}$ are linked to form a heterocycle, e.g., a substituted or unsubstituted piperdinyl ring. In a further embodiment, the piperdinyl is substituted with one or more fluorines or halogenated alkyl groups, e.g., at the 2, 3, 4, or 5 position. In another embodiment, the $R^9$ moiety is (4'trifluoromethyl-piperdin-1-yl) methyl, (4',4'-difluoro-piperdin-1-yl) methyl, or (4'-fluoropiperdin-1-yl) methyl.

In another embodiment, $R^4$ is $NR^{4'}R^{4''}$, $R^{4'}$ and $R^{4''}$ are methyl, $R^5$ is hydroxyl and X is $CR^6R^{6'}$, wherein $R^6$ is methyl and $R^{6'}$ is hydrogen, and $R^7$ is hydrogen In another embodiment, $R^{9a}$ is alkyl, alkenyl, or arylalkyl. In a further embodiment, the piperdinyl is substituted with one or more fluorines or halogenated alkyl groups, e.g., at the 2, 3, 4, or 5 position. In another embodiment, the $R^9$ moiety is (4'trifluoromethyl-piperdin-1-yl) methyl, (4',4'-difluoro-piperdin-1-yl) methyl, or (4'-fluoropiperdin-1-yl) methyl.

In another further embodiment, $R^{9a}$ is substituted alkyl. Examples include alkoxy substituted alkyl (e.g., —$(CH_2)_2$—O—$CH_3$), alkenyl substituted alkyl (e.g., —$CH_2$—CH=C($CH_3)_2$, —$CH_2$—C($CH_3$)=$CHCH_3$, —$CH_2$—CH=CH-phenyl, etc.), heterocyclic substituted alkyl (e.g., —$CH_2$-furanyl, —$CH_2$—CH=CH-furanyl, —$CH_2$-pyridinyl, optionally substituted), cyano substituted alkyl (e.g., $(CH_2)_2$—CN, etc.), alkynyl substituted alkyl (e.g., —$(CH_2)_2$—C≡CH, etc.), halogen substituted alkyl (e.g., $(CH_2)_2$—$CF_3$, $(CH_2)_3$—$CF_3$, —$CH_2$—$CF_3$, —$CH_2$—$CH_2F$, etc.), amido substituted alkyl (e.g., —$CH_2$—C(=O)—N($CH_3)_2$, —$CH_2$—C(=O)—$NH_2$, etc.), carbonyl substituted alkyl (e.g., $CH_2$—C(=O)—$CH_3$, —$CH_2$—C (=O)—C(CH₃)₃, etc.), hydroxy substituted alkyl (e.g., (CH₂—CH(OH)—CH₃, —CH₂—C(OH)(CH₃)₂, etc.), —CH₂—C(=N—O—CH₃)—CH₃, cycloalkyl (e.g., adamantyl, etc.).

In another embodiment, $R^{9a}$ is substituted or unsubstituted benzyl. In a further embodiment, $R^{9a}$ is substituted with one or more fluorines (e.g., at the 2, 3, 4, 5, or 6 positions).

In a further embodiment, $R^{9b}$ is hydrogen, substituted or unsubstituted alkyl (e.g., methyl, ethyl, —CH₂—CH=CH-furanyl, —CH₂—CH=C(CH₃)₂, —(CH₂)₃—CF₃, —(CH₂)₂—CH₂F, —CH₂—CH₂F, —(CH₂)₂—CF₃, —CH₂—CF₃, etc.).

In another further embodiment, $R^{9a}$ and $R^{9b}$ may be linked to form a pyrrolidinyl, piperazinyl, piperidinyl, pyrazinyl, azapanyl, thiomorpholinyl, morpholinyl, tetrahydroquinolinyl, or a decahydroquinolinyl ring. The ring maybe substituted with one or more fluorines at the 2, 3, 4, or 5 position. The ring may also be substituted with one or more fluorinated alkyl groups (e.g., CH₂F, —CHF₂, CF₃, etc.), cyano groups, hydroxy groups, alkyl groups (e.g., methyl, ethyl, spiro-cyclohexyl, t-butyl, etc.), heterocyclic (e.g., optionally substituted morpholinyl), thiol groups, alkoxy groups, alkyloxycarbonyl groups, carbonyl groups (optionally bonded directly to an atom in the ring), and exocyclic and endocyclic double bonds. In one embodiment, the ring is substituted with a =CF₂ group. The ring may also be linked to a —O—(CH₂)₂—O— group which maybe attached to the pyrollidinyl or piperidinyl ring through one carbons or through two adjacent carbons.

When $R^9$ is linked to $R^{10}$ to form a furanyl ring, the ring can be further substituted, e.g., with phenyl or other substituents which allow the compound of the invention to perform its intended function.

In a further embodiment, the tetracycline compound is selected from the group consisting of:

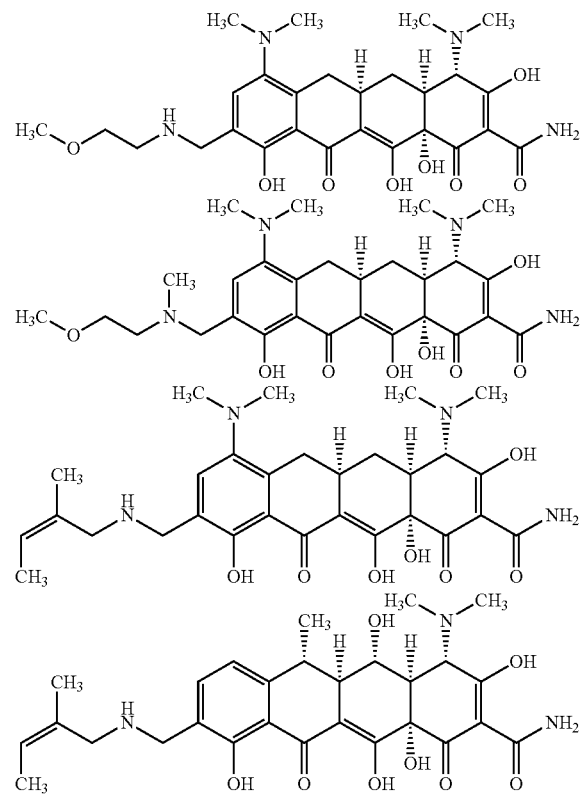

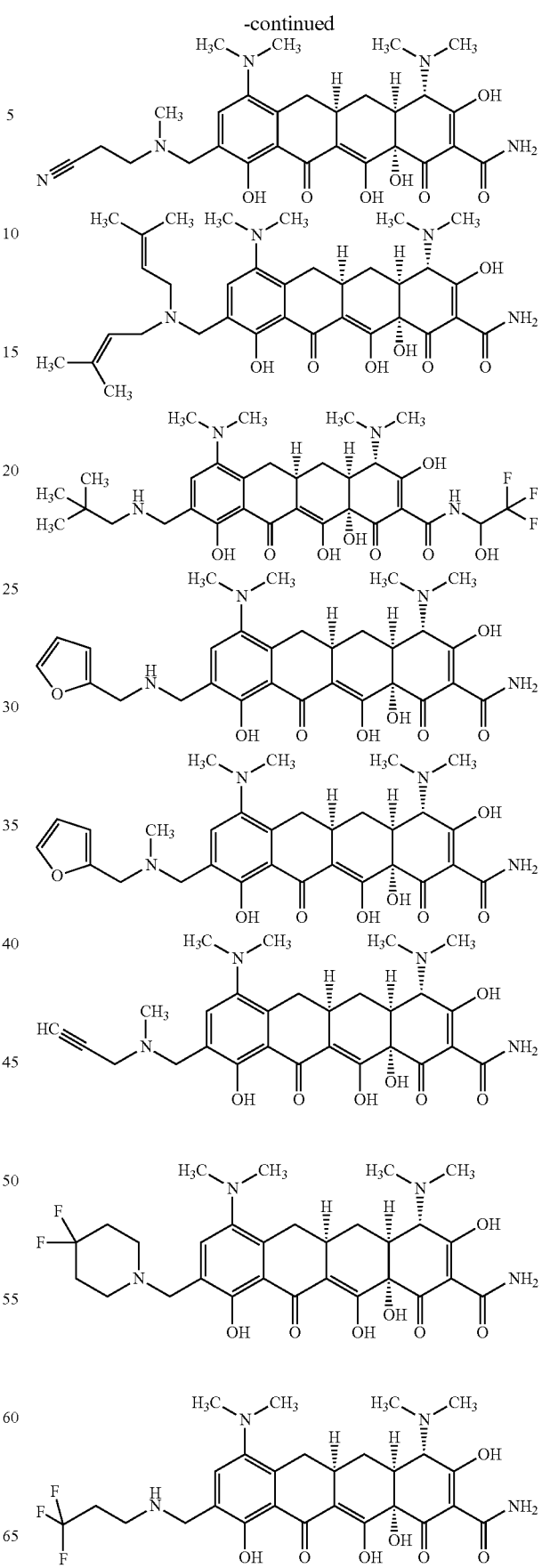

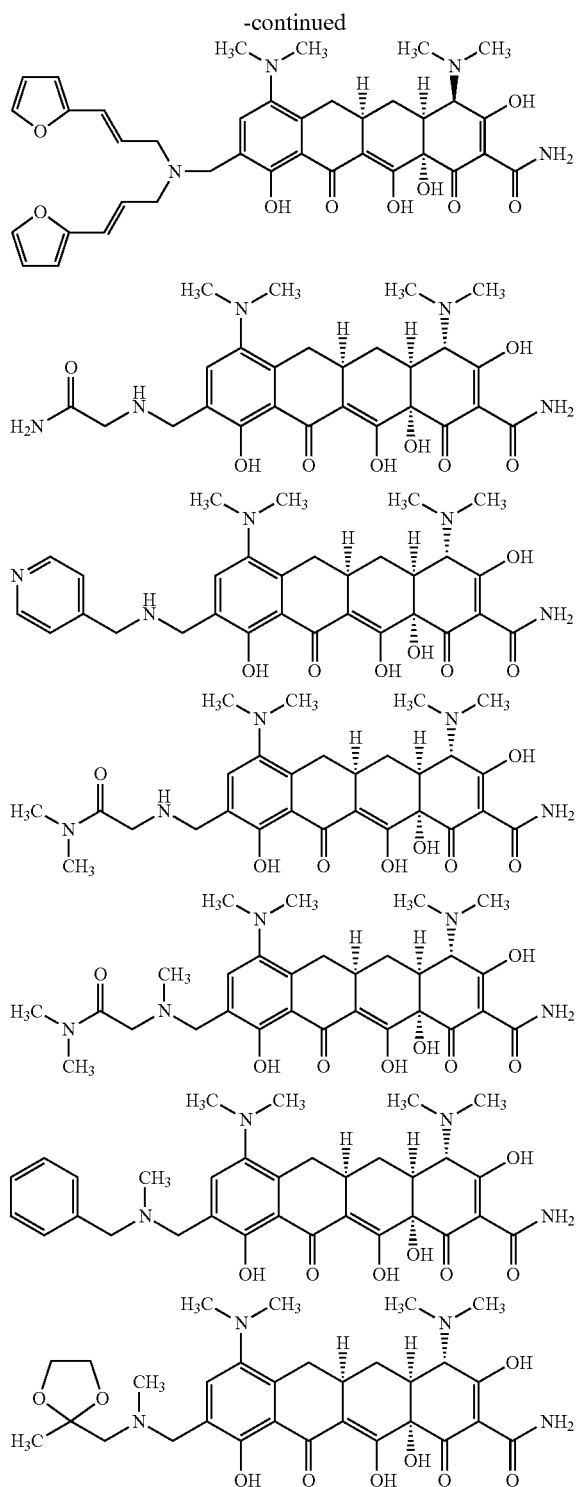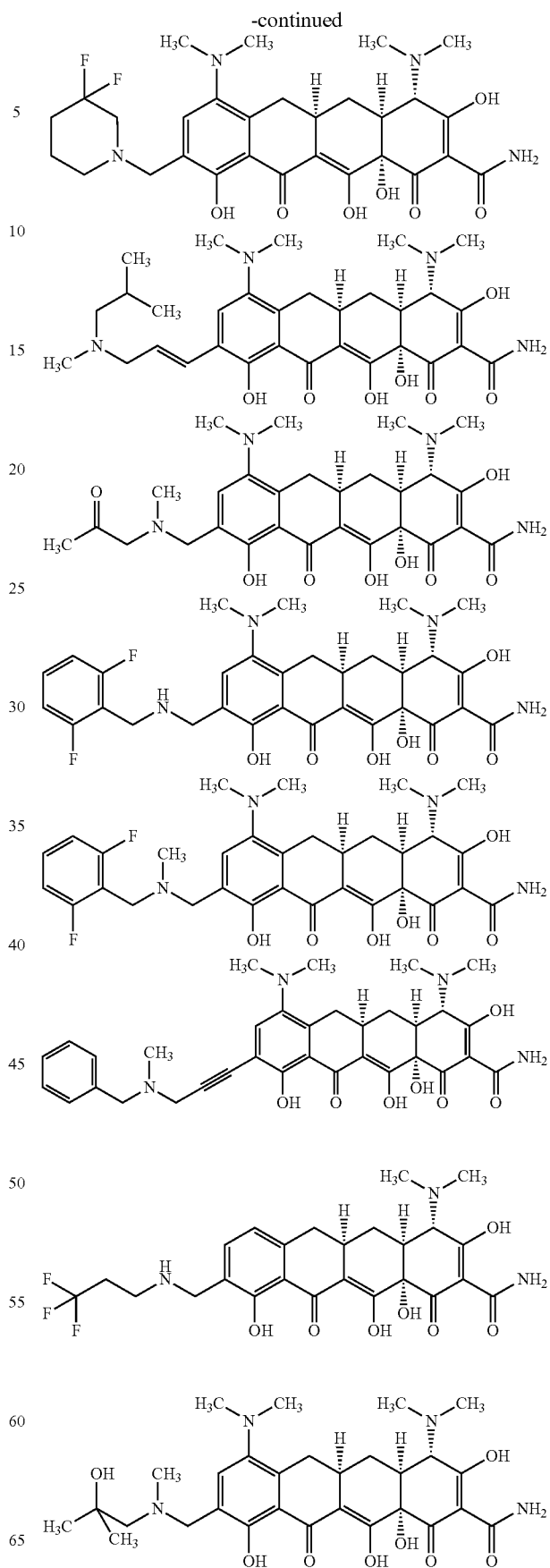

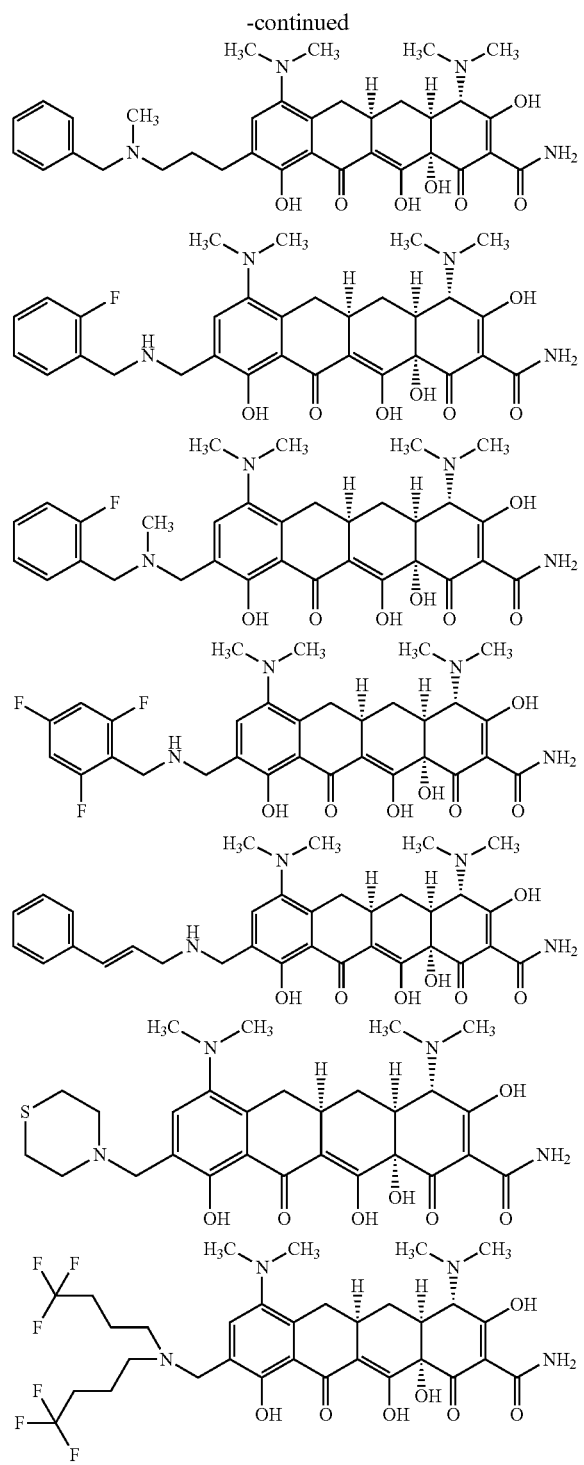
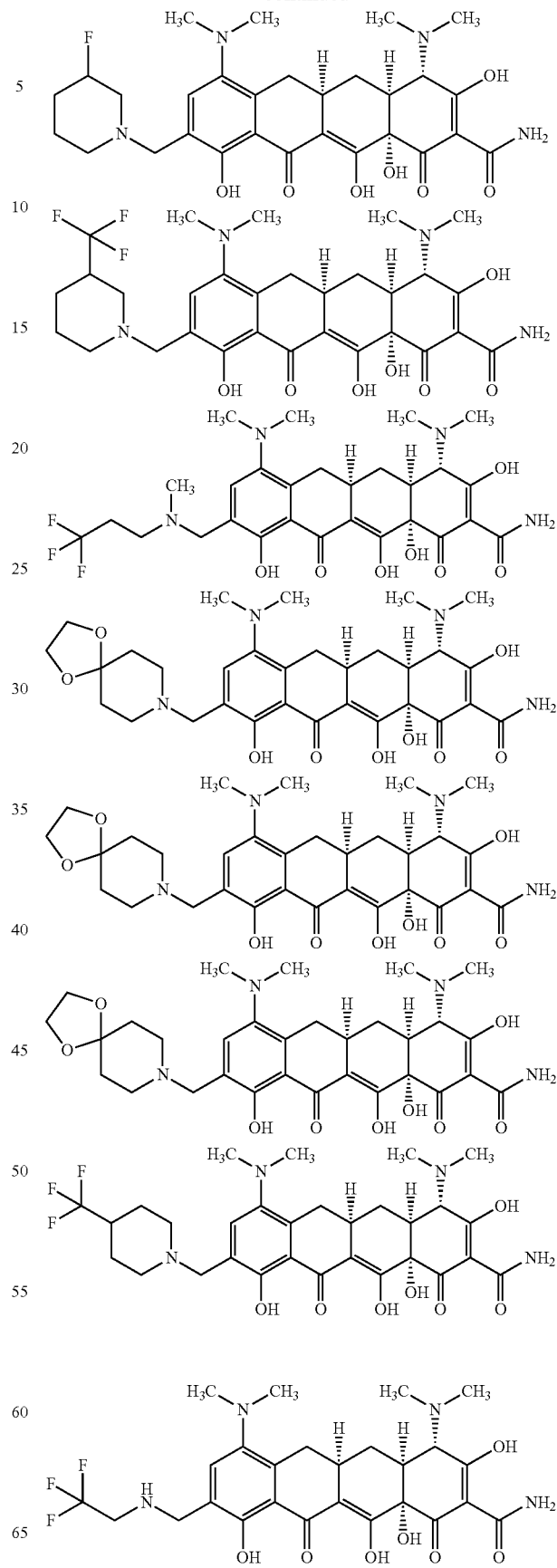

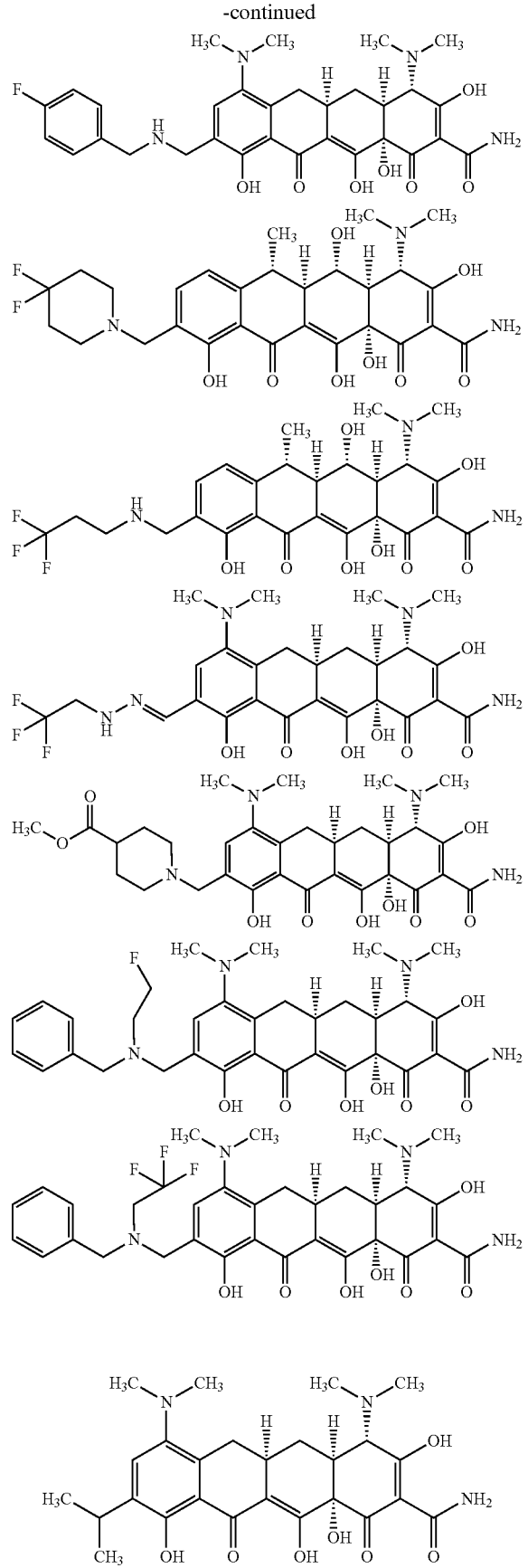
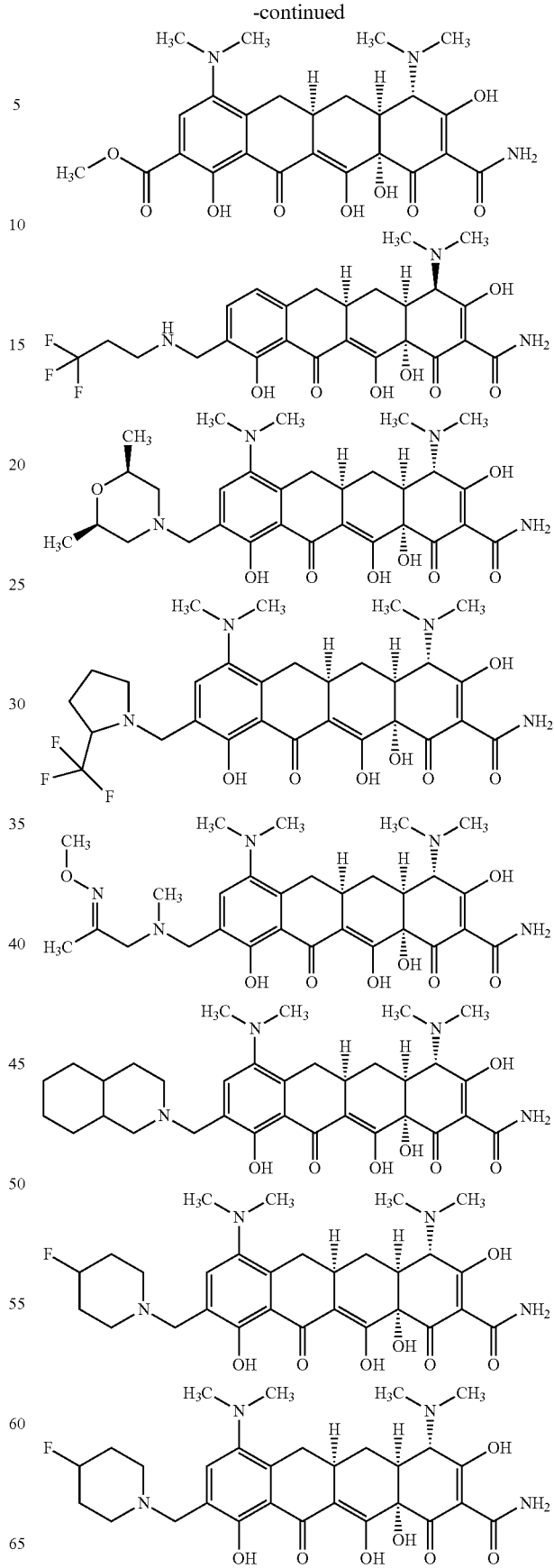

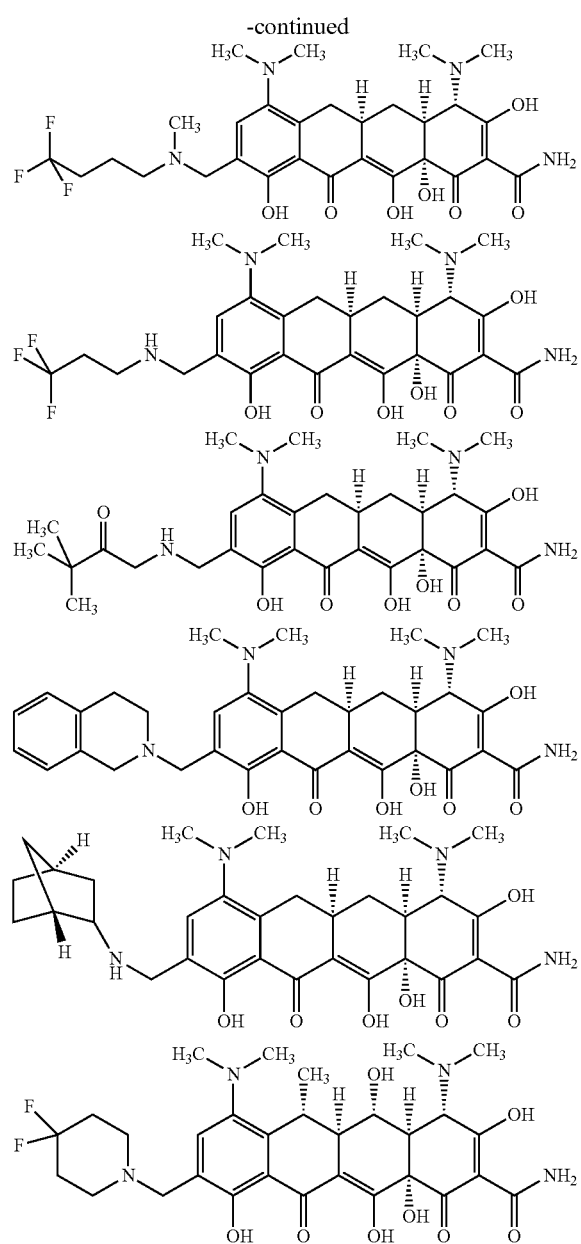
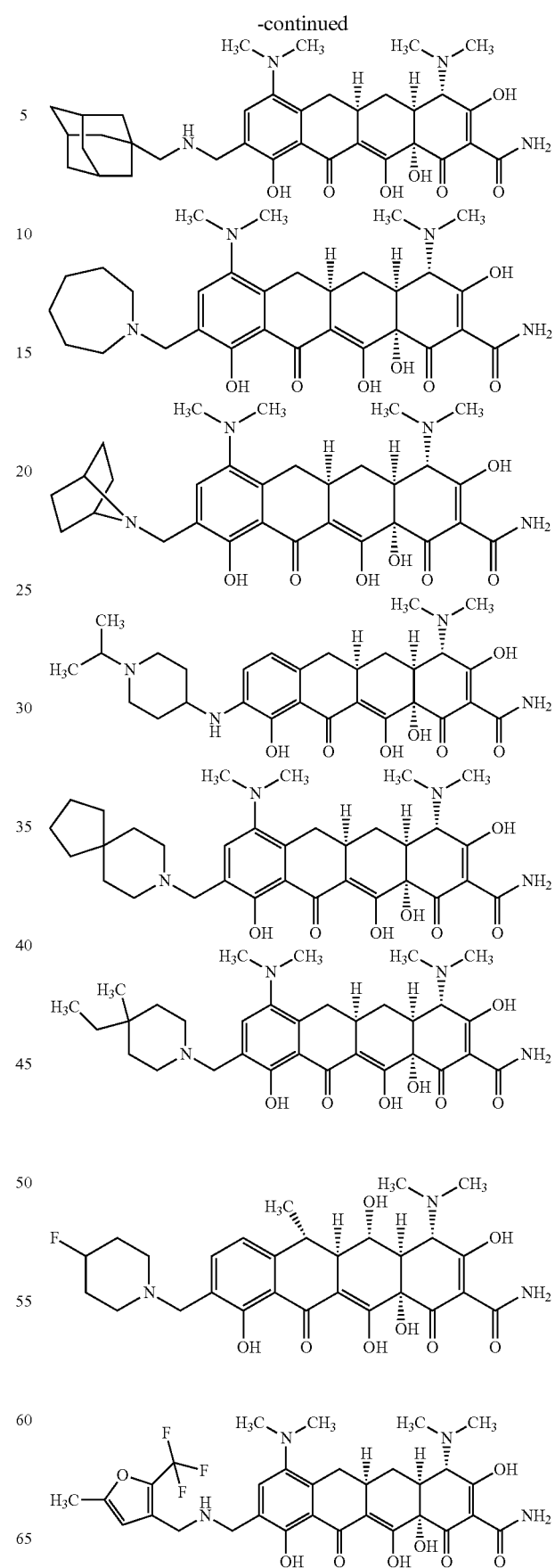

25
-continued
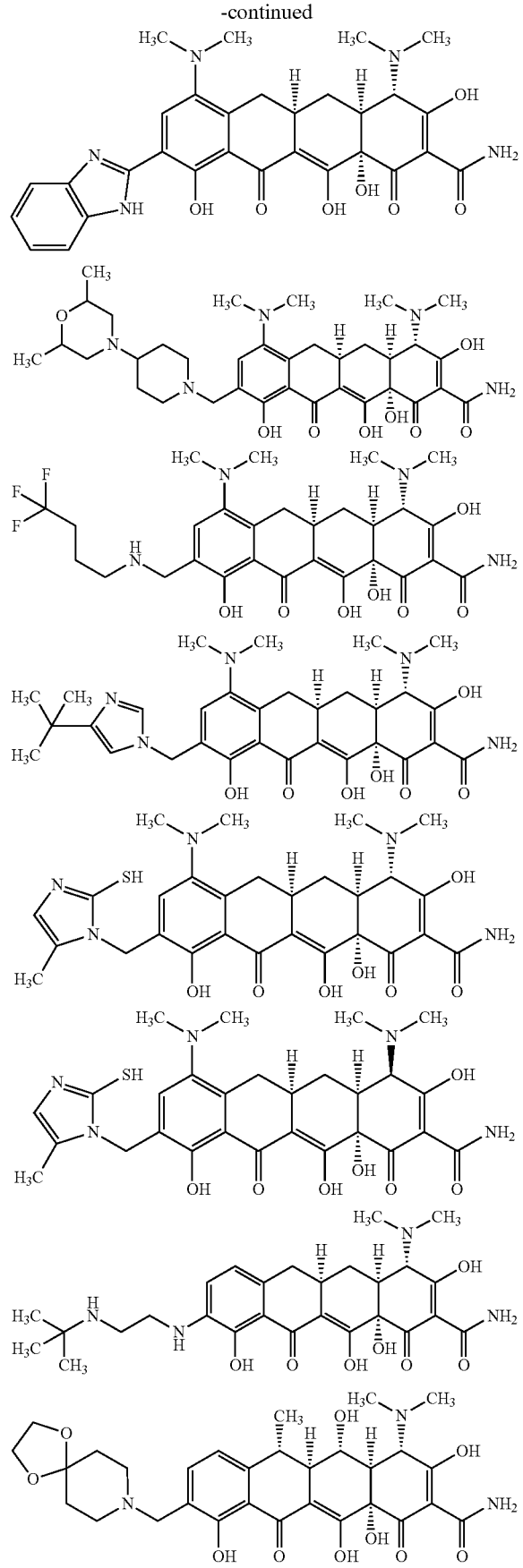
26
-continued
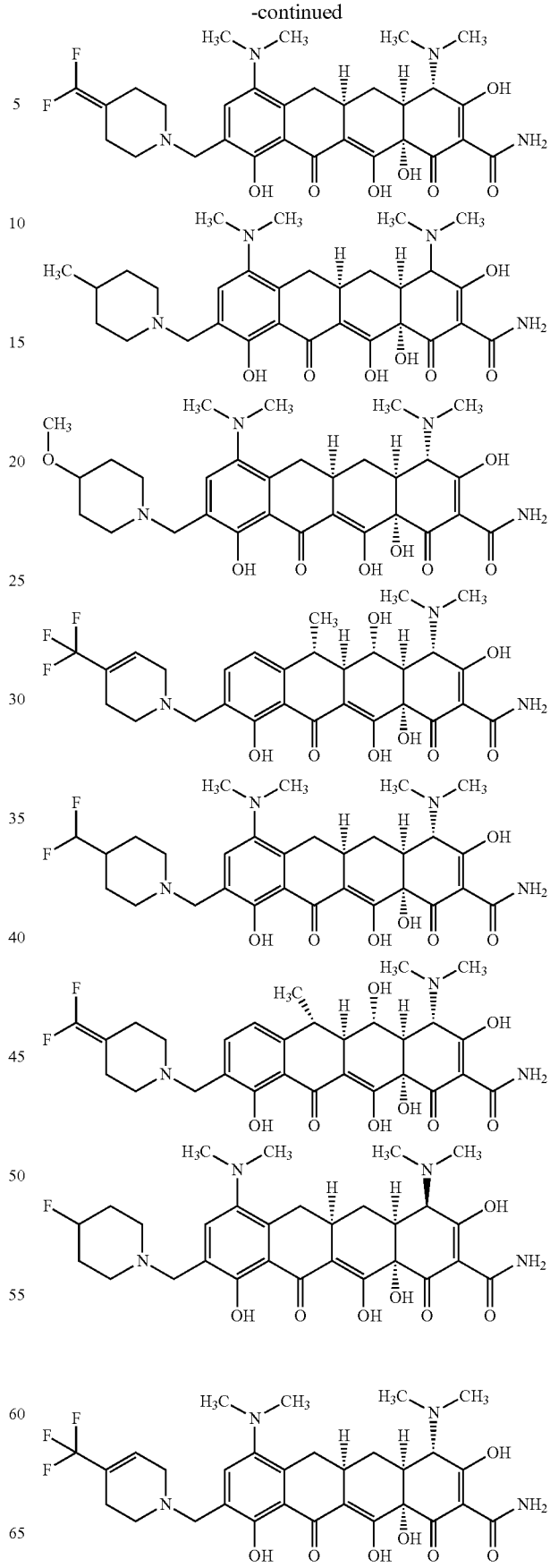

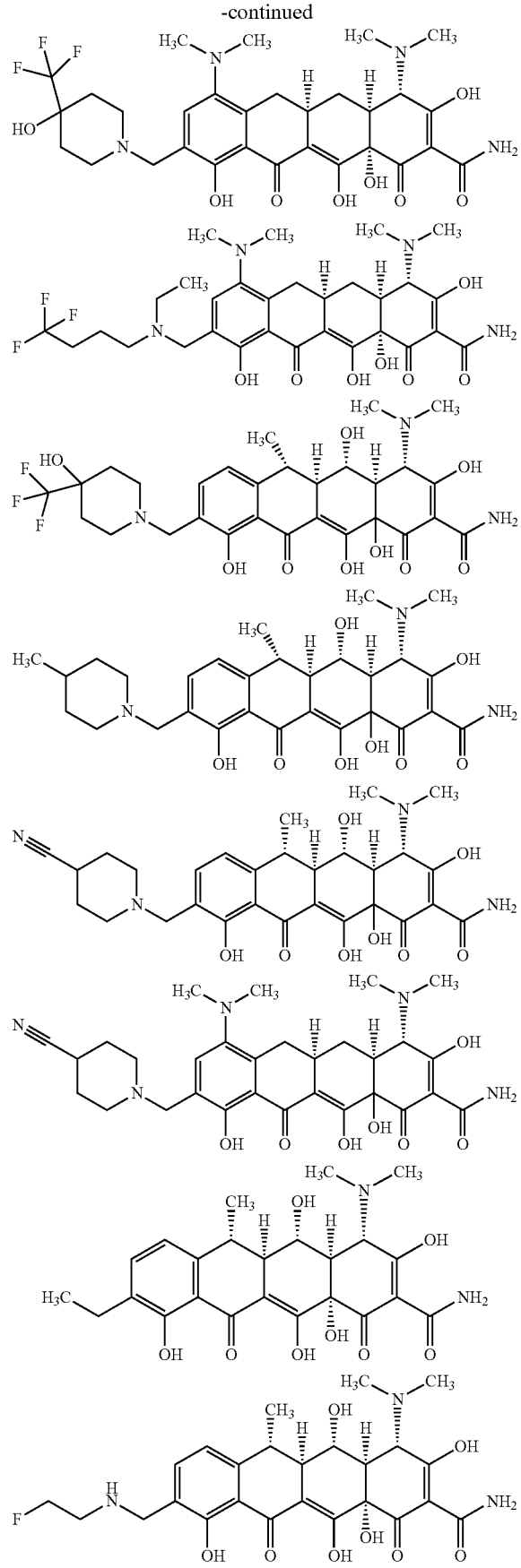
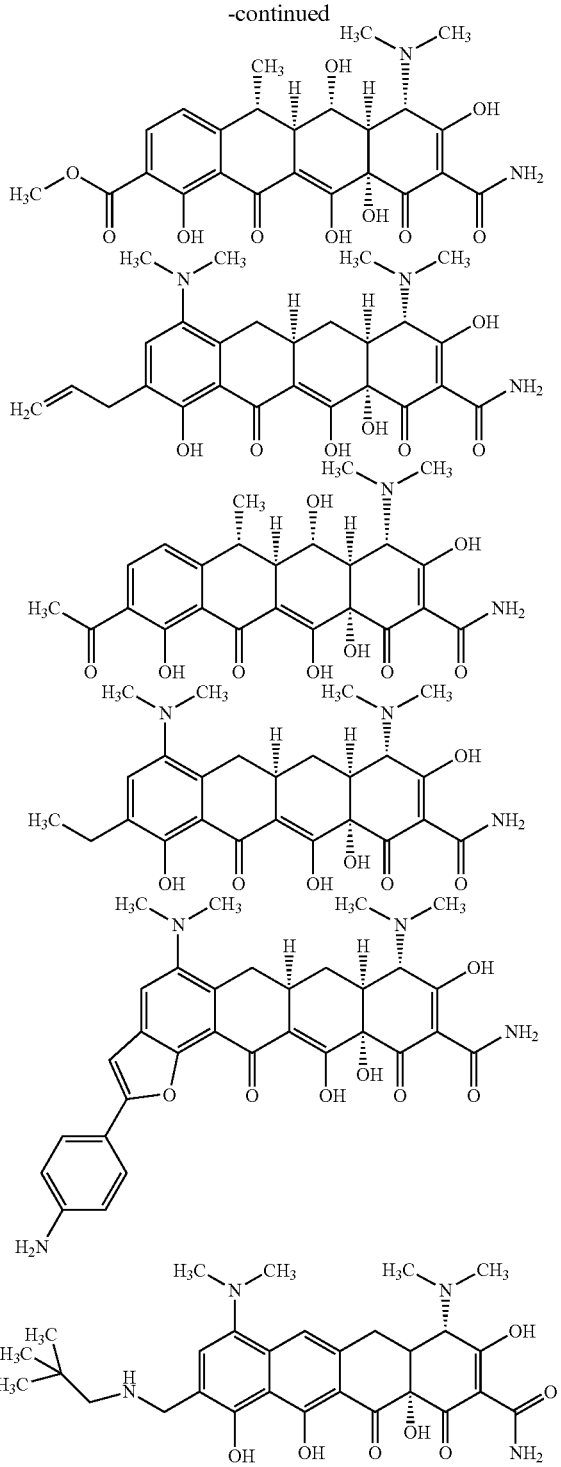

and pharmaceutically acceptable salts, esters, and prodrugs thereof.

3. 7-Substituted Tetracycline Compounds

In one embodiment, the invention pertains to novel 7-substituted tetracycline compounds.

The term "7-substituted tetracycline compounds" includes tetracycline compounds with substitution at the 7 position. In one embodiment, the substitution at the 7-position enhances the ability of the tetracycline compound to perform its intended function, e.g., treat tetracycline responsive states. In an embodiment, the 7-substituted tetracycline compound is 7-substituted tetracycline (e.g., wherein $R^4$ is $NR^{4'}R^{4''}$, $R^{4'}$ and $R^{4''}$ are methyl, $R^5$ is hydrogen and X is $CR^6R^{6'}$, wherein $R^6$ is methyl and $R^{6'}$ is hydroxy); 7-substituted doxycycline (e.g., wherein $R^4$ is $NR^{4'}R^{4''}$, $R^{4'}$ and $R^{4''}$ are methyl, $R^5$ is hydroxyl and X is $CR^6R^{6'}$, wherein $R^6$ is methyl and $R^{6'}$ is hydrogen); 7-substituted tetracycline compound, wherein X is $CR^6R^{6'}$, $R^4$, $R^5$, $R^{6'}$, and $R^6$ are hydrogen; or 7-substituted sancycline (wherein $R^4$ is $NR^{4'}R^{4''}$, $R^{4'}$ and $R^{4''}$ are methyl; $R^5$ is hydrogen and X is $CR^6R^{6'}$ wherein $R^6$ and $R^{6'}$ are hydrogen atoms).

The invention pertains, at least in part, to 7-substituted tetracycline compound of Formula III:

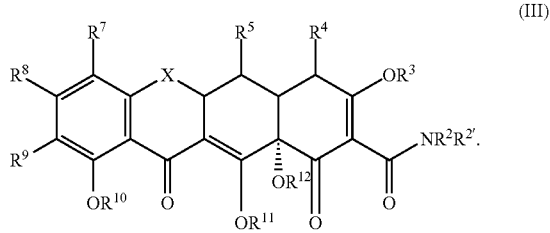

wherein:

X is $CHC(R^{13}Y'Y)$, $CR^6R^6$, $C=CR^6R^6$, S, $NR^6$, or O;

$R^2$, $R^{2'}$, $R^{4'}$, and $R^{4''}$ are each independently hydrogen, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;

$R^4$ is $NR^{4'}R^{4''}$, alkyl, alkenyl, alkynyl, aryl, hydroxyl, halogen, or hydrogen;

$R^{2'}$, $R^3$, $R^{10}$, $R^{11}$ and $R^{12}$ are each hydrogen or a pro-drug moiety;

$R^5$ is hydroxyl, hydrogen, thiol, alkanoyl, aroyl, alkaroyl, aryl, heteroaromatic, alkyl, alkenyl, alkynyl, alkoxy, alkylthio, alkylsulfinyl, alkylsulfonyl, alkylamino, arylalkyl, alkyl carbonyloxy, or aryl carbonyloxy;

$R^6$ and $R^{6'}$ are each independently hydrogen, methylene, absent, hydroxyl, halogen, thiol, alkyl, alkenyl, alkynyl, aryl, alkoxy, alkylthio, alkylsulfinyl, alkylsulfonyl, alkylamino, or an arylalkyl;

$R^7$ is substituted or unsubstituted pyrazolyl, furanyl, thiophenyl, or thiazolyl;

$R^8$ is hydrogen, hydroxyl, halogen, thiol, alkyl, alkenyl, alkynyl, aryl, alkoxy, alkylthio, alkylsulfinyl, alkylsulfonyl, alkylamino, or an arylalkyl;

$R^9$ is hydrogen;

$R^{13}$ is hydrogen, hydroxy, alkyl, alkenyl, alkynyl, alkoxy, alkylthio, alkylsulfinyl, alkylsulfonyl, alkylamino, or an arylalkyl; and Y' and Y are each independently hydrogen, halogen, hydroxyl, cyano, sulfhydryl, amino, alkyl, alkenyl, alkynyl, alkoxy, alkylthio, alkylsulfinyl, alkylsulfonyl, alkylamino, or an arylalkyl, and pharmaceutically acceptable salts thereof.

In a further embodiment, $R^4$ is $NR^{4'}R^{4''}$; X is $CR^6R^{6'}$, $R^2$, $R^{2'}$, $R^5$, $R^6$, $R^{6'}$, $R^8$, $R^9$, $R^{10}$, $R^{11}$, and $R^{12}$ are each hydrogen; and, $R^{4'}$, and $R^4$ are each lower alkyl, e.g., methyl.

In one embodiment, the tetracycline compound is a doxycycline compound and $R^7$ is substituted or unsubstituted aminomethyl (e.g., $-CH_2NR^{7a}R^{7b}$).

In one embodiment, $R^7$ is substituted (e.g., N-alkyl substituted) or unsubstituted pyrazolyl. In another embodiment, $R^7$ is diethyl amino. In another, $R^7$ is substituted amino methyl. In a further embodiment, the substituted aminomethyl is substituted with a pentyl group (e.g., $-CH_2-C(CH_3)_3$), two methyl groups, or fluorinated alkyl (e.g., fluorinated propyl, e.g., $-CH_2-CH_2-CF_3$).

In another embodiment, $R^7$ is substituted phenyl. In a further embodiment, $R^7$ is phenyl substituted at the 5 position (of the phenyl ring) with an alkyl substituted amino methyl group (e.g., ($-CH_2-N(CH_3)_2$, $-CH_2-NH-CH(CH_3)_2$, $-CH_2-N(CH_3)-CH(CH_3)_2$, $-CH_2-N$-piperdinyl), $-CH_2NH-CH_3$, $-CH_2-NH$-cyclopropyl, $CH_2-NH$-t-butyl, $-CH_2-N(CH_3)$-benzyl, $-CH_2-N(CH_3)-CH_2-CH=CH_2$, $CH_2-NH-(CH_2)_2-CF_3$, $CH_2-NH-CH_2-C(=O)-NH_2$, or $-CH_2-NH$-cyclohexyl). In a further embodiment, the piperdine may be substituted at its 4 position (e.g., with fluorine, methyl, etc.).

In another embodiment, when $R^7$ is a phenyl substituted at the 5 position with an alkyl substituted amino methyl group, the phenyl may also be substituted with a fluorine (e.g., at the 2, 3, 4, or 6 position) or an alkoxy (e.g., methoxy group) at the 2, 3, 4, or 6 position.

In another embodiment, $R^7$ is phenyl with a 2-position amino alkyl substituent. In a further embodiment, the substituent is dialkylaminomethyl (e.g., dimethylaminomethyl, $-CH_2$-N-piperazinyl). In a further embodiment, the piperazine is substituted with one or more fluorine or methyl groups. In another further embodiment, the phenyl $R^7$ is further substituted at the 3, 4, 5, or 6 position with a methoxy group. In another embodiment, the phenyl is linked to a methylene dioxy group through its 4 and 5 positions.

In another embodiment, $R^7$ is phenyl with a 4-position amino alkyl (e.g., aminomethyl) substituent. In a further embodiment, the aminoalkyl substituent is $-CH_2-NH-CH(CH_3)_2$, $-C(CH_3)-NH-(CH_2)_2-CH_2F$, $-CH_2-NH-CH_2$-cyclohexenyl, $-CH_2-N$-piperidinyl, $-CH_2-N(CH_3)-CH_2-CH=CH_2$, or $-CH_2-NH-(CH_2)_2-CF_3$).

In another embodiment, $R^7$ is phenyl substituted with a $-C(=N-O-R)-R'$ group, wherein R and R' are each alkyl. In a further embodiment, the substituent is at the 4-position of the phenyl ring. In another embodiment, $R^7$ is phenyl substituted at the 4-position with an alkoxyalkyl group ($-CH_2-O-CH_3$). In another embodiment, $R^7$ is phenyl substituted with an alkylcarbonylamino group.

In another embodiment, $R^7$ is substituted furanyl. In a further embodiment, the furanyl is attached at the 2-position of the furanyl ring. In a further embodiment, the furanyl is substituted with an amino alkyl, e.g., aminomethyl group at its 5-position. Examples of aminomethyl groups include: $-CH_2N(CH_3)-CH_2-C_6H_5$, $-CH_2-N(CH_3)-CH_2-CH=CH_2$, $-CH_2-N(CH_3)-CH(CH_3)_2$, or $-CH_2-N$-piperidinyl. In another embodiment, the furanyl is substituted at the 3-position, e.g., with an aminoalkyl substituent. Examples of such substituents include $-CH_2-N(CH_3)_2$, $-CH_2-N$-piperidinyl In another embodiment, $R^7$ is substituted furanyl attached at its 3-position. In a further embodiment, the furanyl is substituted with an aminoalkyl substituent. In another further embodiment, the aminoalkyl substituent is $-CH_2-N$-piperazinyl or $-CH_2-N-(CH_3)_2$.

In another embodiment, $R^7$ is substituted or unsubstituted thiophenyl. In a further embodiment $R^7$ is is substituted with an aminoalkyl moiety. In another further embodiment, the aminoalkyl moiety is $-CH_2-N-(CH_3)_2$.

In another further embodiment, $R^7$ is substituted pyridinyl. In a further embodiment, $R^7$ is attached to the phenyl ring at its 3-position. In another further embodiment, it is substituted with a aminoalkyl moiety at its 5-position.

Examples of aminoalkyl moieties include —CH₂—N—(CH₃)₂, —CH₂—N-piperidinyl, —CH₂—N(CH₃)—CH₂—CH=CH₂, or —CH₂—N(CH₃)—CH(CH₃)₂.

In another further embodiment, R⁷ is alkylcarbonylaminoalkyl. In another further embodiment, R⁷ is —CH₂—NH—C(=O)—CH₃.

In another further embodiment, R⁷ is amino substituted alkenyl. In another further embodiment, R⁷ is —CH=CH—CH₂—N(CH₃)₂ or —CH=CH—CH₂—N-piperidinyl. In another embodiment, R⁷ is amino substituted alkynyl (e.g., —C≡C—CH₂—N(CH₃)—(CH₂)₂—CF₃ or —C≡C—(CH₂)₂—N-piperidinyl.

In another further embodiment, R⁷ is substituted —CH₂—N-piperidinyl. In certain embodiments, the piperidinyl is substituted with one or more fluorines, e.g., at the 4-position of the piperdine ring.

In another embodiment, the R⁷ substitutent is alkylaminocarbonyl. In a further embodiment, the substituent is —C(=O)—NH—(CH₂)₂—N(CH₃)₂.

In another further embodiment, the R⁷ substituent is aminoalkylcarbonyl. In a further embodiment, the substituent is —C(=O)—CH₂—N(CH₃)₂, —C(=O)—CH₂—NH—(CH₂)₂—OCH₃, —C(=O)—CH₂—N-piperidinyl and —C(=O)—CH₂—N-pyrollidinyl.

In another further embodiment, the R⁷ substituent is N-piperdinyl substituted alkyl. In a further embodiment, the R⁷ substituent is —(CH₂)₄—N-piperdinyl or —(CH₂)₂—N-piperdinyl.

In another embodiment, the R⁷ substituted is —(CH₂)₂—N(CH₃)₂ or C(=O)—CH₃.

In another further embodiment, the R⁷ substituent is aminoalkyloxycarbonyl. Examples of aminoalkyloxycarbonyl substituents include C(=O)—O—(CH₂)₂—N-piperdinyl and —C(=O)—O—(CH₂)₂—N(CH₃)₂.

In a further embodiment, the compounds of the invention are:

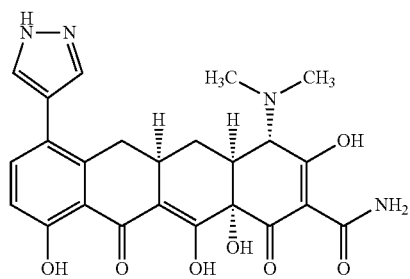

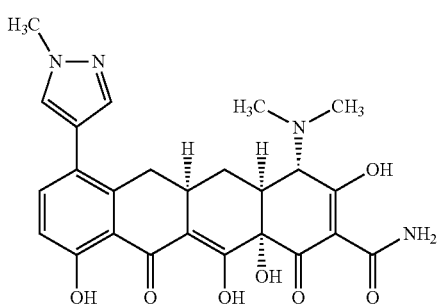

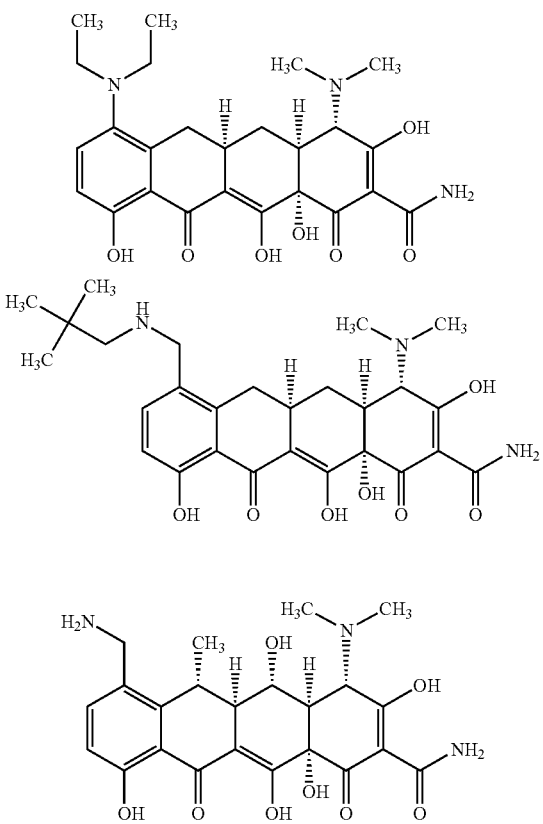

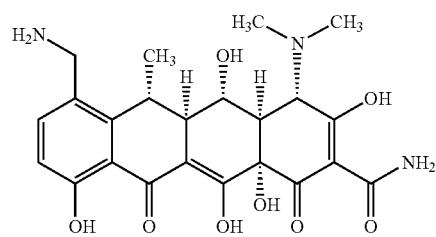

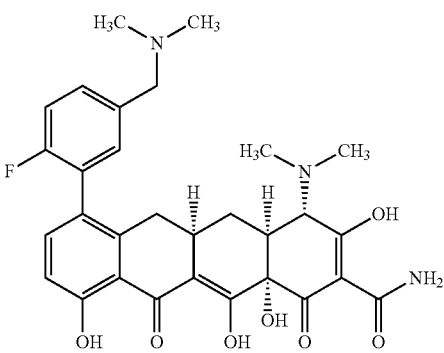

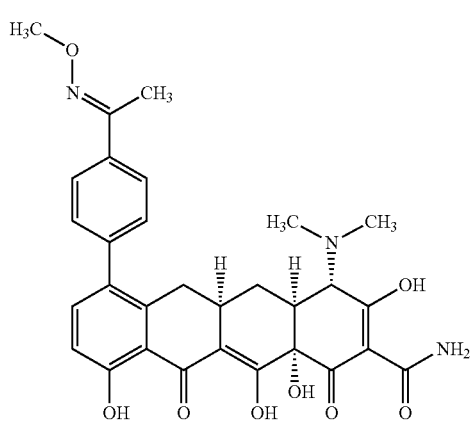

33
-continued
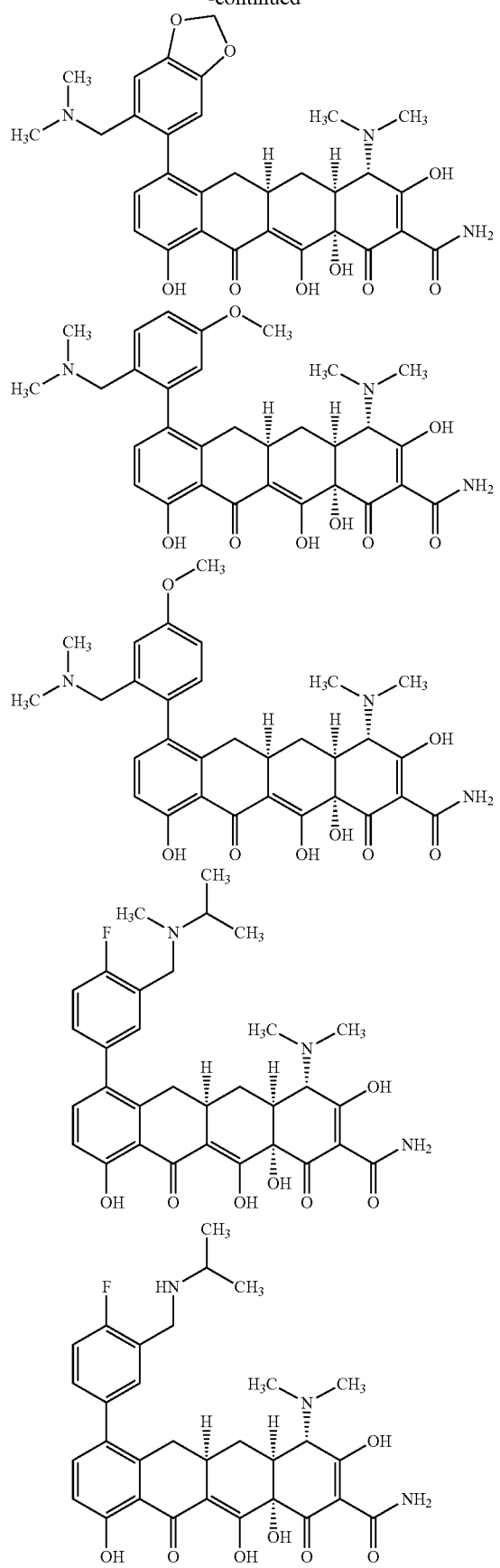
34
-continued
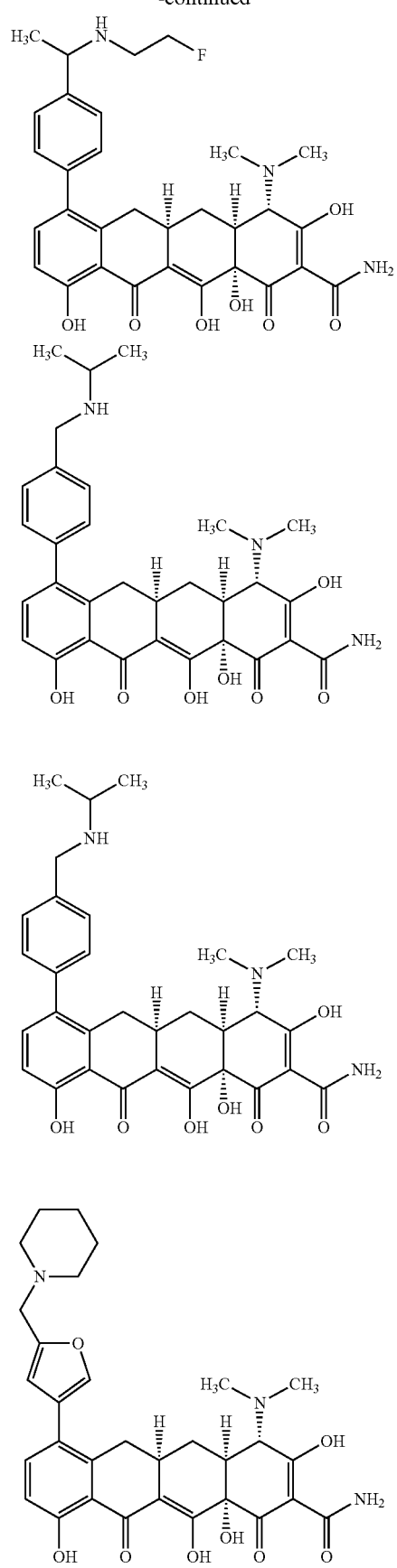

35
-continued
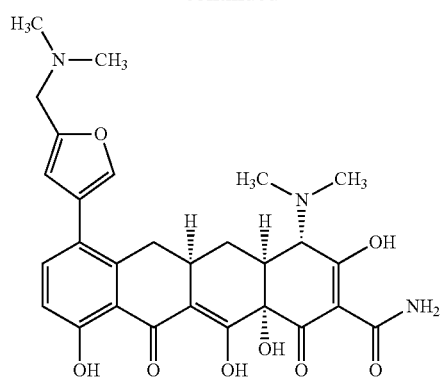
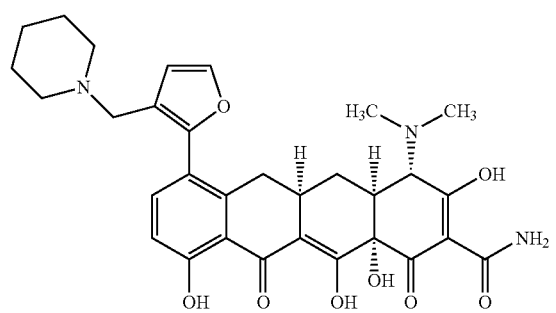
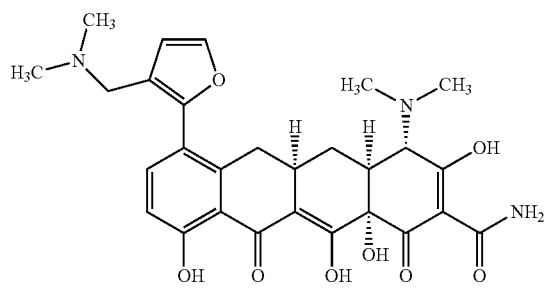
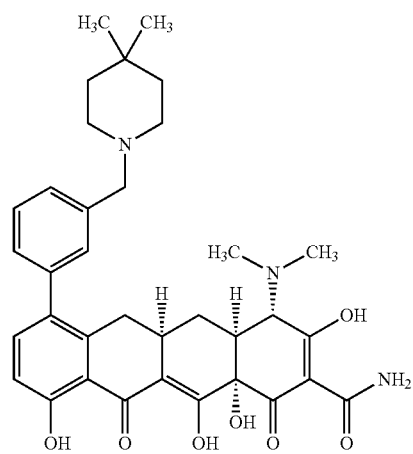
36
-continued
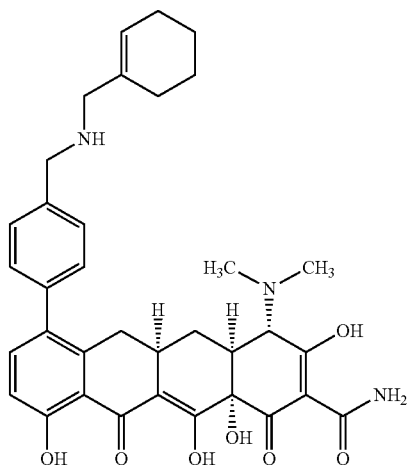
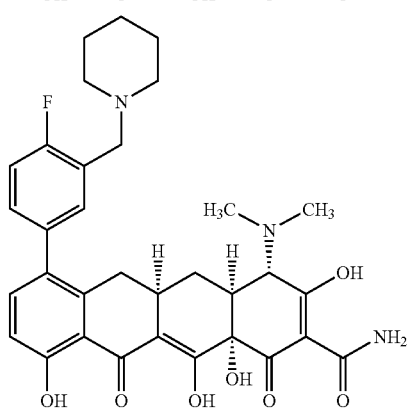
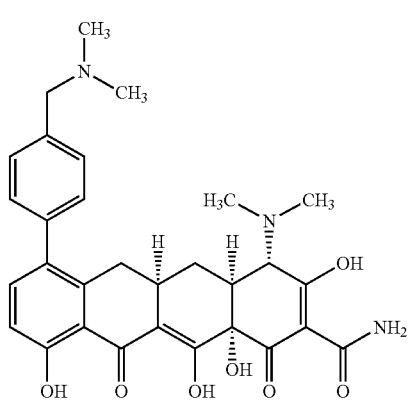
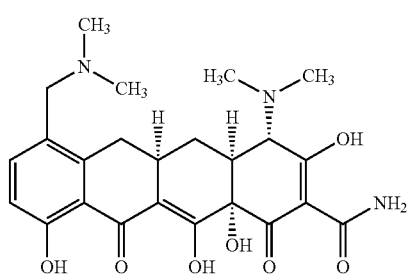

37
-continued
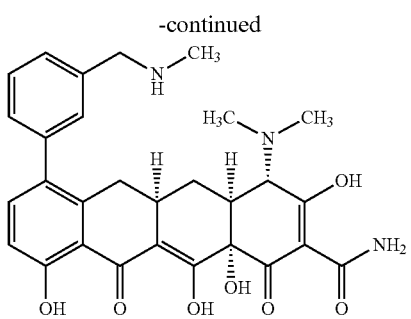
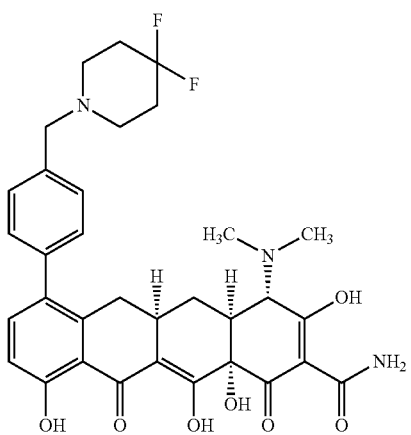
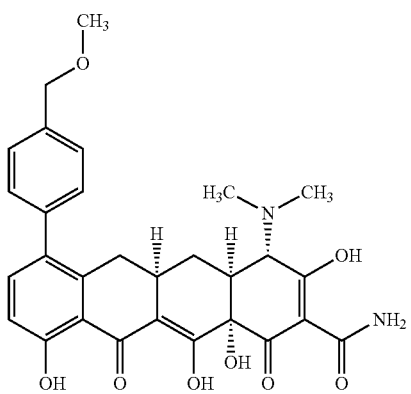
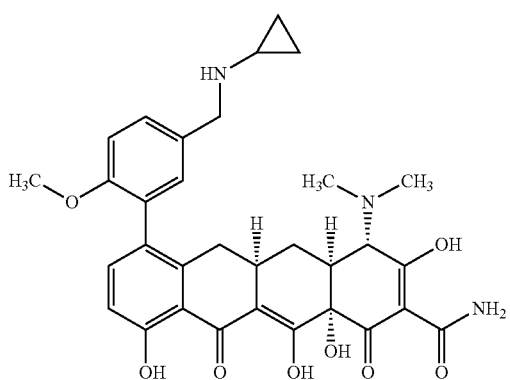
38
-continued
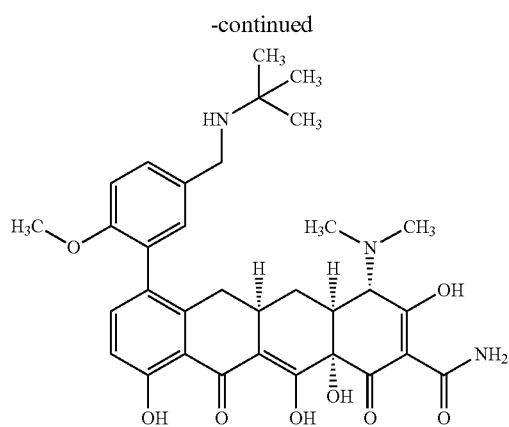
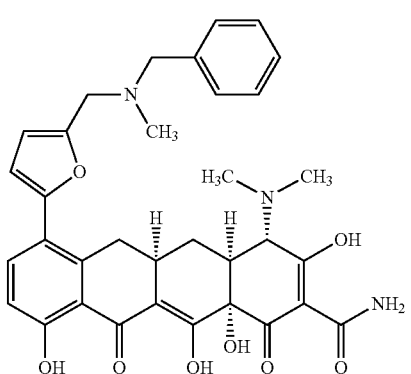
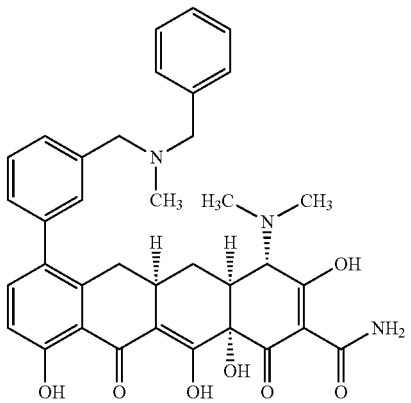
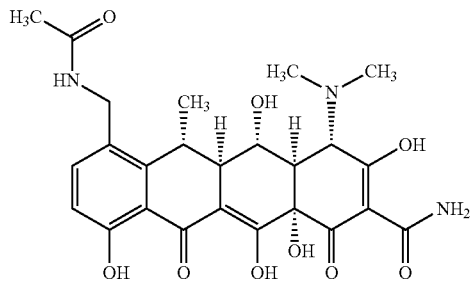

39
-continued
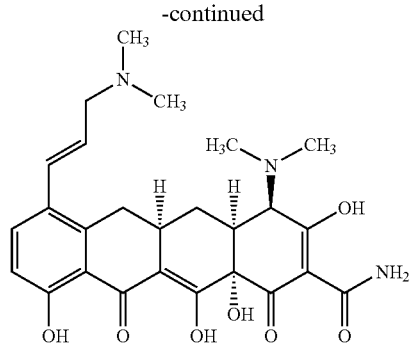
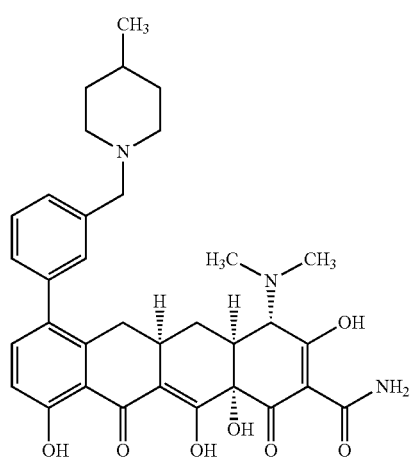
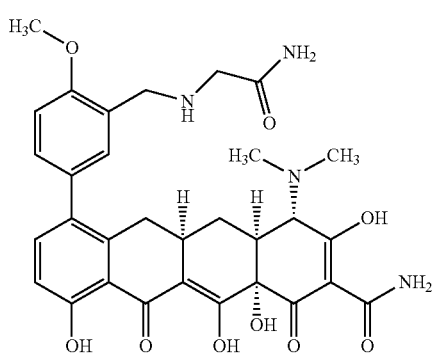
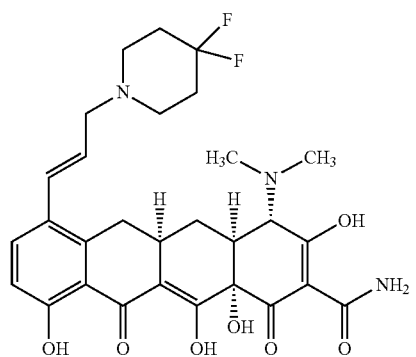
40
-continued
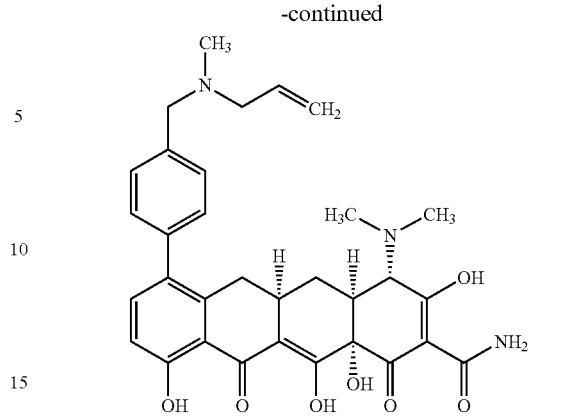
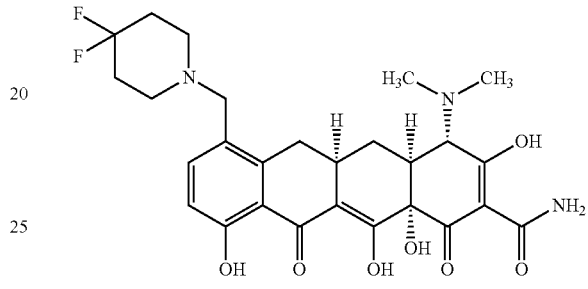
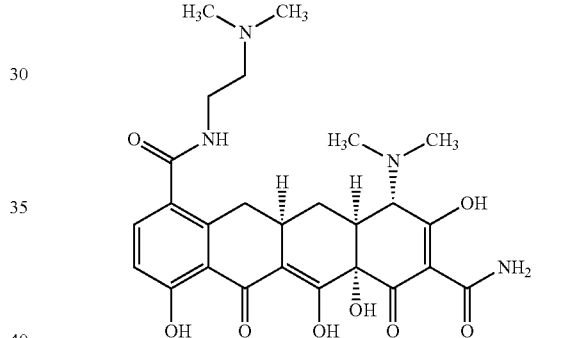
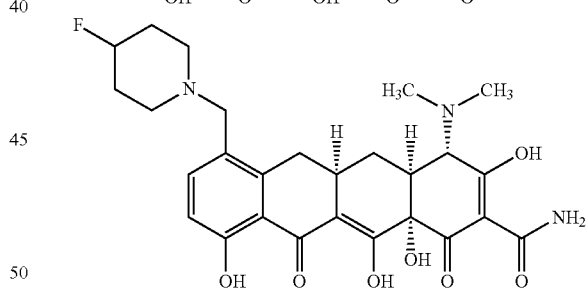
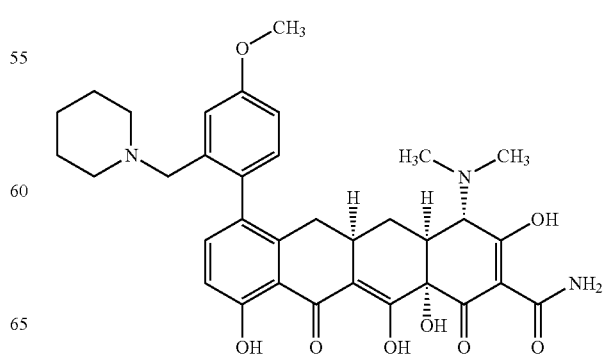

41
-continued
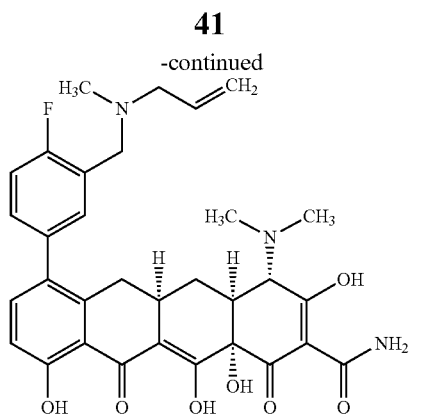
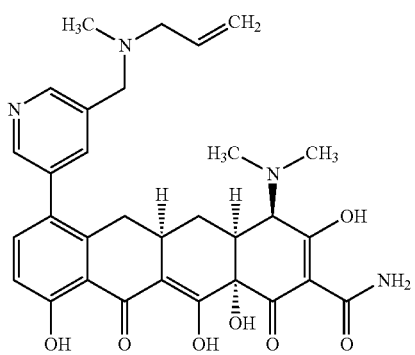
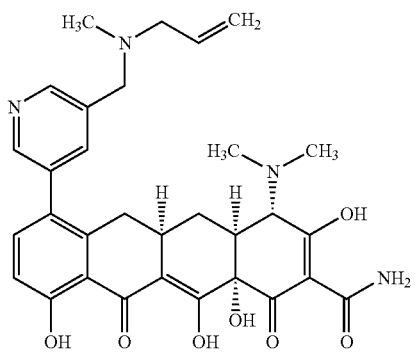
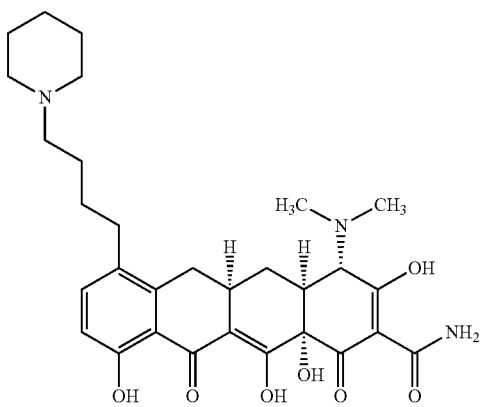
42
-continued
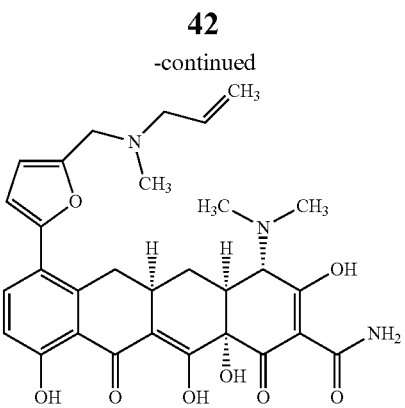
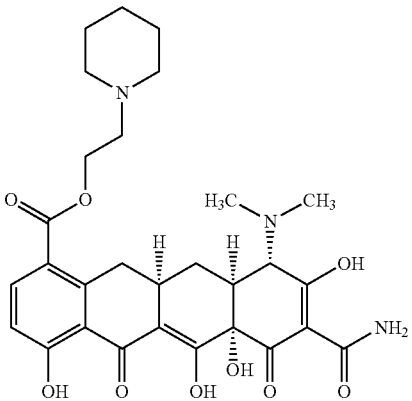
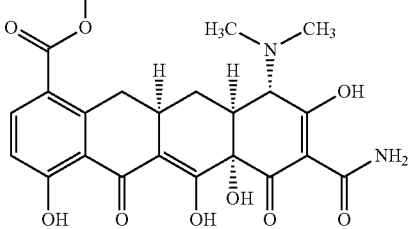
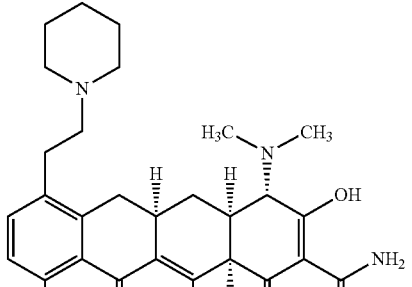
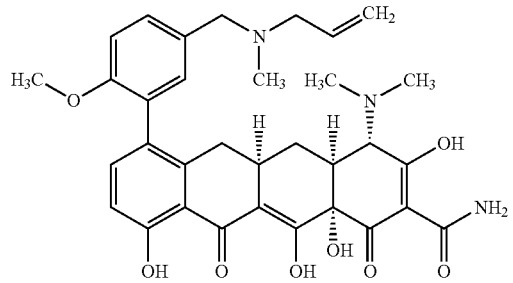

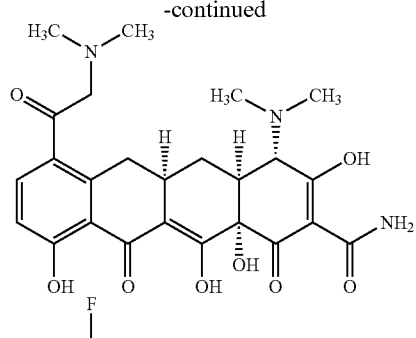
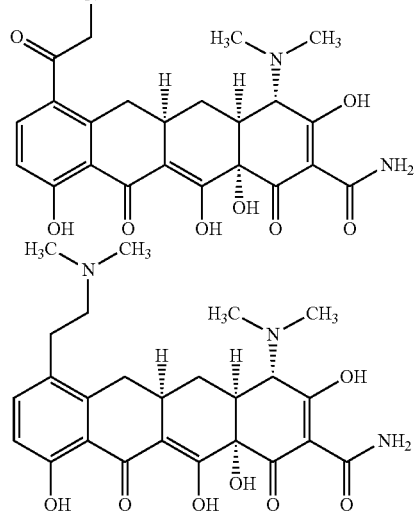
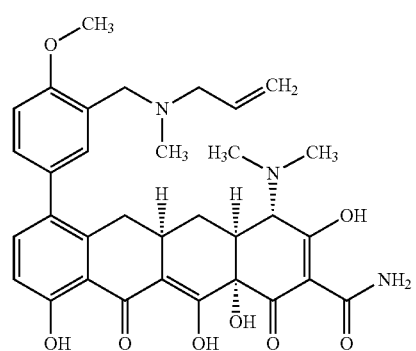
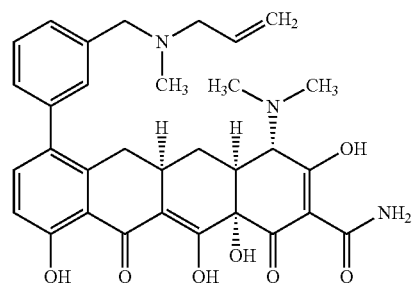
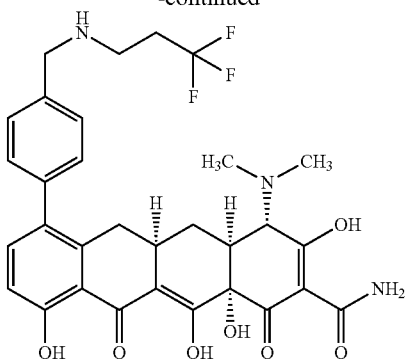
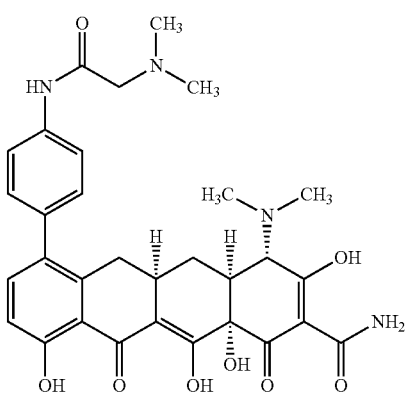
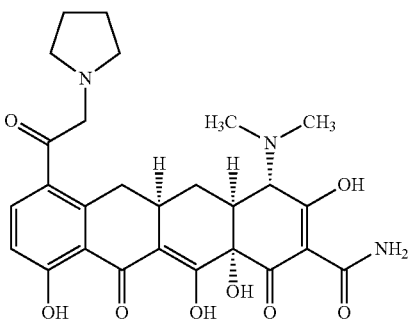
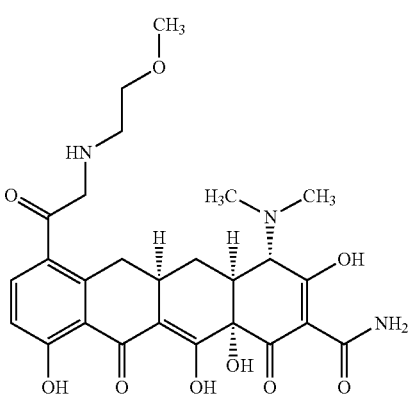

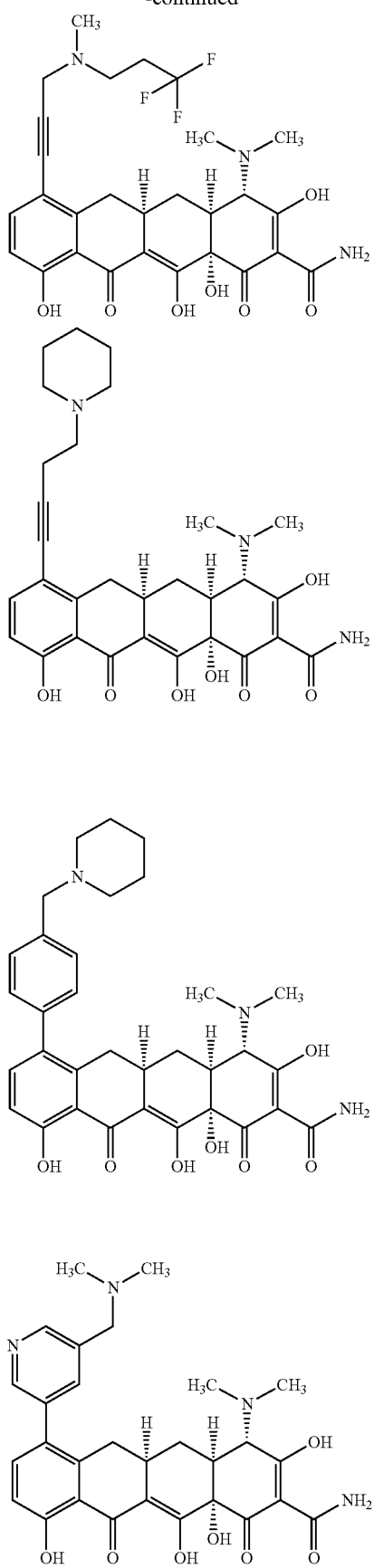
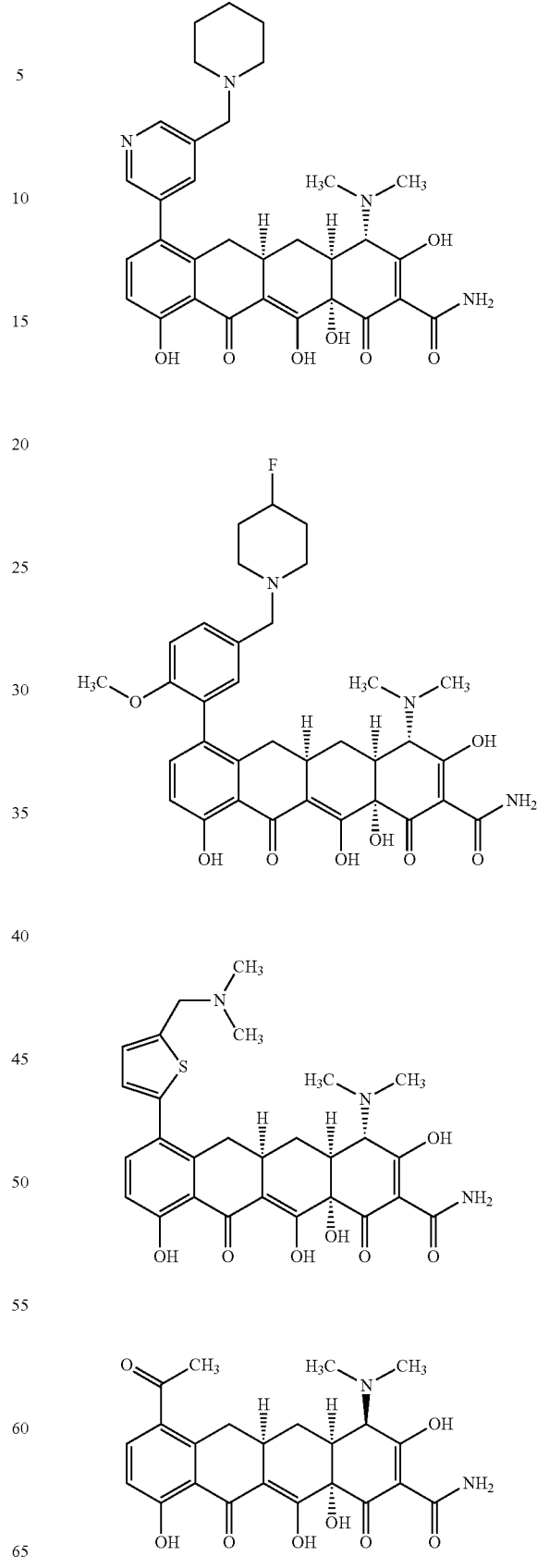

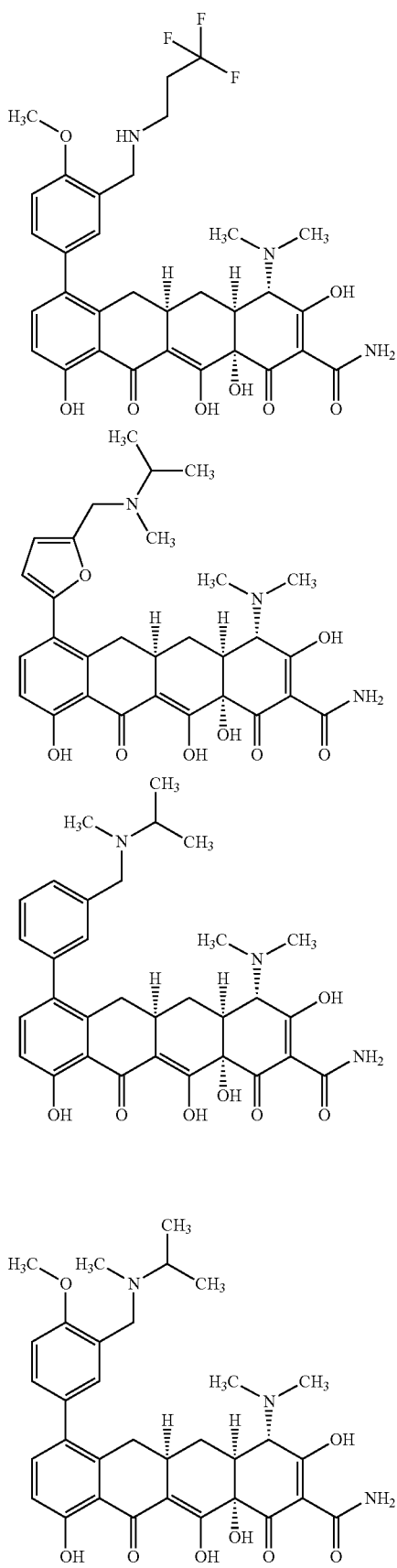
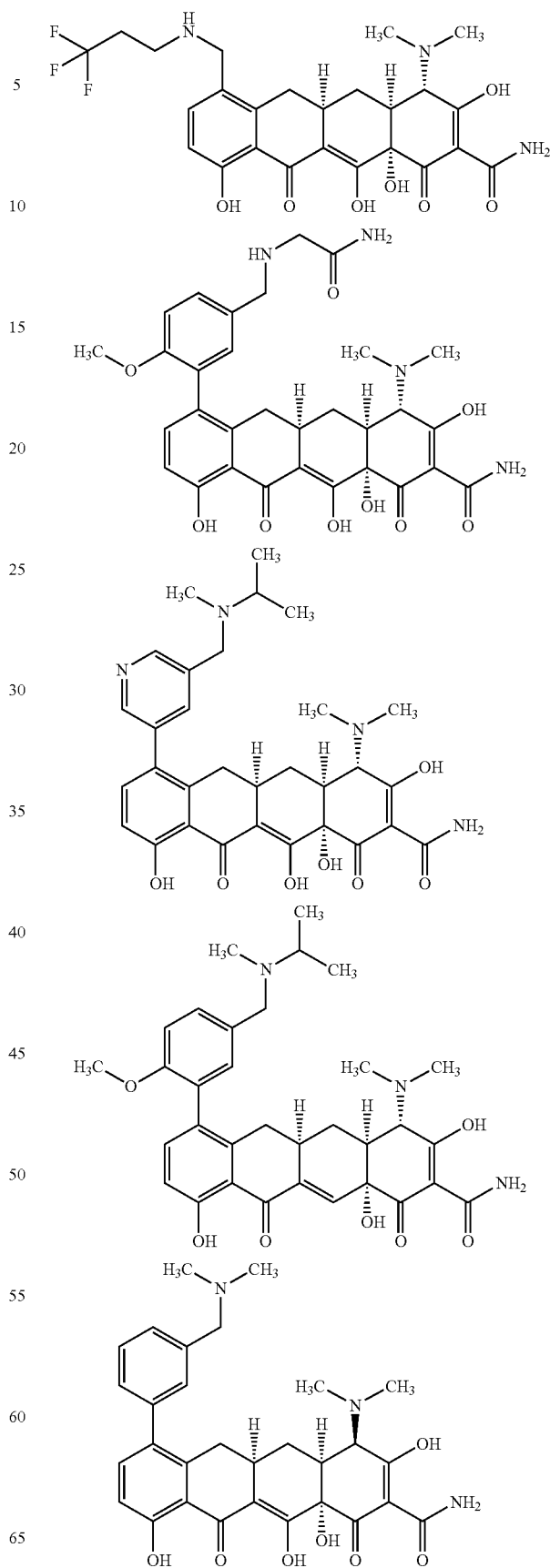

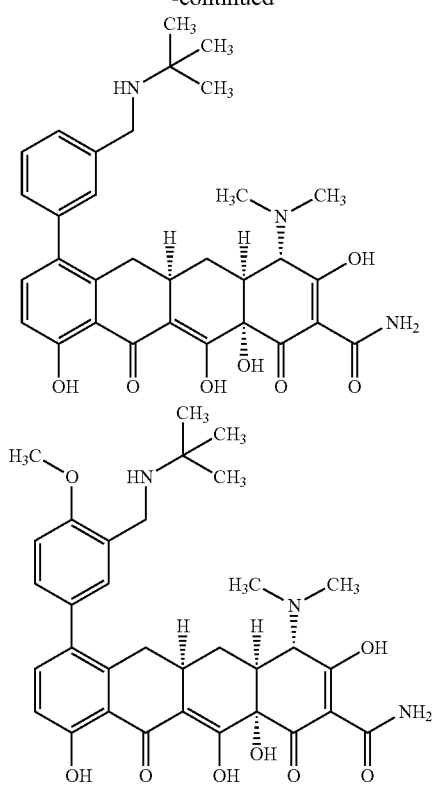
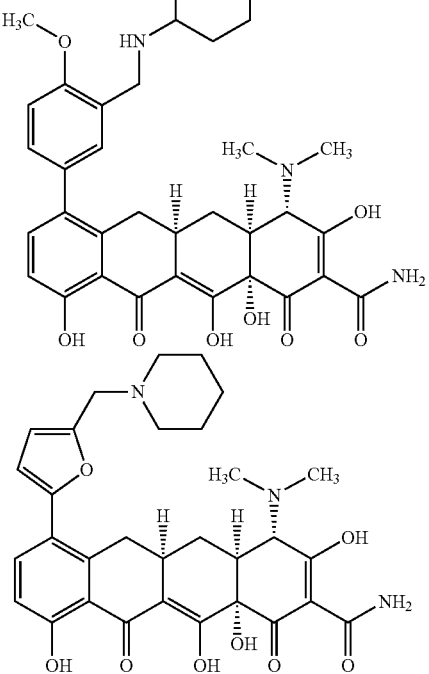
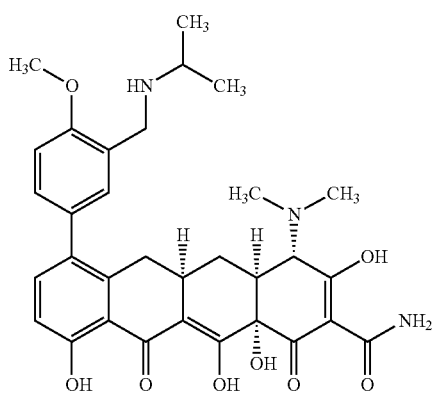
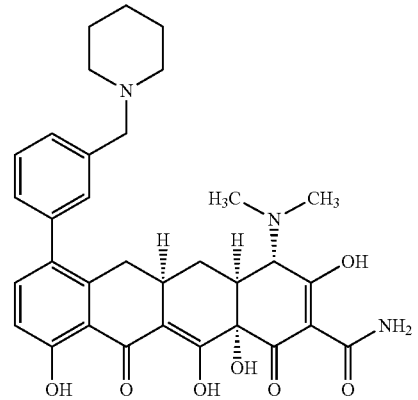
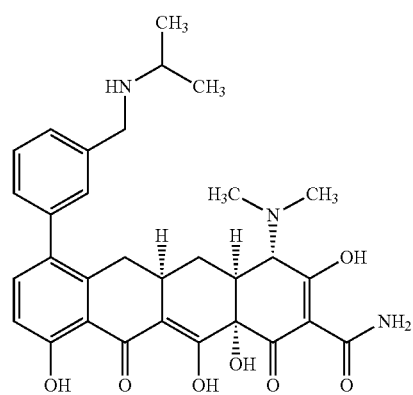
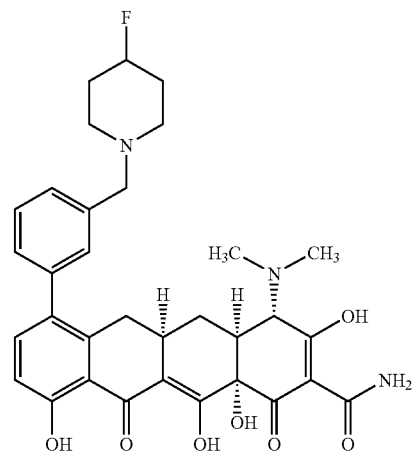

-continued

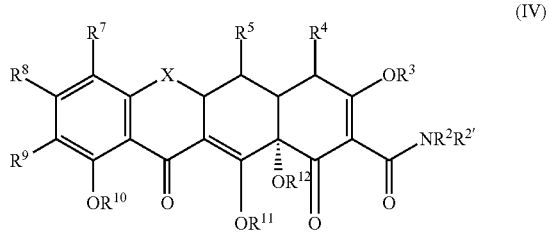

and pharmaceutically acceptable esters, prodrugs, and salts thereof.

4. 8-Substituted Tetracycline Compounds

The invention also pertains, at least in part to 8-substituted tetracycline compounds.

The term "8-substituted tetracycline compounds" includes tetracycline compounds with substitution at the 8-position. In one embodiment, the substitution at the 8-position enhances the ability of the tetracycline compound to perform its intended function, e.g., treat tetracycline responsive states. In an embodiment, the 8-substituted tetracycline compound is 8-substituted tetracycline (e.g., wherein $R^4$ is $NeR^{4''}$; $R^{4'}$ and $R^{4''}$ are methyl, $R^5$ is hydrogen and X is $CR^6R^{6'}$, wherein $R^6$ is methyl and $R^{6'}$ is hydroxy); 8-substituted doxycycline (e.g., wherein $R^4$ is $NR^{4'}R^{4''}$; $R^{4'}$ and $R^{4''}$ are methyl, $R^5$ is hydroxyl and X is $CR^6R^{6'}$, wherein $R^6$ is methyl and $R^{6'}$ is hydrogen); or 8-substituted sancycline (wherein $R^4$ is $NR^{4'}R^{4''}$; $R^{4'}$ and $R^{4''}$ are methyl; $R^5$ is hydrogen and X is $CR^6R^{6'}$ wherein $R^6$ and $R^{6'}$ are hydrogen atoms. In an embodiment, the substitution at the 7 position of the 8-substituted tetracycline compound is not chlorine or trimethylamino. In one embodiment, $R^4$ is hydrogen.

In one embodiment, the 8-substituted tetracycline compound is of formula IV:

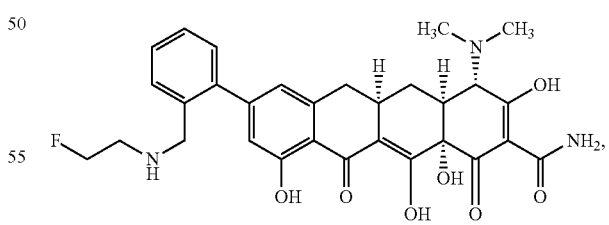

(IV)

wherein:

X is $CHC(R^{13}Y'Y)$, $CR^{6'}R^6$, S, $NR^6$, or O;

$R^2$, $R^{4'}$, $R^{4''}$, $R^{7'}$ and $R^{7''}$ are each hydrogen, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;

$R^4$ is $NR^{4'}R^{4''}$, alkyl, alkenyl, alkynyl, aryl, hydroxyl, halogen, or hydrogen;

$R^{2'}$, $R^3$, $R^{10}$, $R^{11}$ and $R^{12}$ are each hydrogen or a pro-drug moiety;

$R^5$ is hydroxyl, hydrogen, thiol, alkanoyl, aroyl, alkaroyl, aryl, heteroaromatic, alkyl, alkenyl, alkynyl, alkoxy, alkylthio, alkylsulfinyl, alkylsulfonyl, alkylamino, arylalkyl, alkyl carbonyloxy, or aryl carbonyloxy;

$R^6$ and $R^{6'}$ are independently hydrogen, methylene, absent, hydroxyl, halogen, thiol, alkyl, alkenyl, alkynyl, aryl, alkoxy, alkylthio, alkylsulfinyl, alkylsulfonyl, alkylamino, or an arylalkyl;

$R^7$ is hydrogen, hydroxyl, halogen, thiol, nitro, alkyl, alkenyl, alkynyl, aryl, alkoxy, alkylthio, alkylsulfinyl, alkylsulfonyl, arylalkyl, amino, arylalkenyl, arylalkynyl, acyl, aminoalkyl, heterocyclic, thionitroso, or $-(CH_2)_{0-3}(NR^{7'})_{0-1}C(=W')WR^{7a}$;

$R^8$ is substituted phenyl or substituted pyridinyl;

$R^9$ is hydrogen, hydroxyl, halogen, thiol, nitro, alkyl, alkenyl, alkynyl, aryl, alkoxy, alkylthio, alkylsulfinyl, alkylsulfonyl, arylalkyl, amino, arylalkenyl, arylalkynyl, acyl, aminoalkyl, heterocyclic, thionitroso, or $-(CH_2)_{0-3}NR^{9c}C(=Z')ZR^{9a}$;

$R^{7a}$, $R^{7b}$, $R^{7c}$, $R^{7d}$, $R^{7e}$, $R^{7f}$, $R^{9a}$, $R^{9b}$, $R^{9c}$, $R^{9d}$, $R^{9e}$, and $R^{8f}$ are each independently absent, hydrogen, acyl, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;

W is $CR^{7d}R^{7e}$, S, O or $NR^{7b}$;

W' is O, $NR^{7f}$, or S;

$R^{13}$ is hydrogen, hydroxy, alkyl, alkenyl, alkynyl, alkoxy, alkylthio, alkylsulfinyl, alkylsulfonyl, alkylamino, or an arylalkyl;

Y' and Y are each independently hydrogen, halogen, hydroxyl, cyano, sulfhydryl, amino, alkyl, alkenyl, alkynyl, alkoxy, alkylthio, alkylsulfinyl, alkylsulfonyl, alkylamino, or an arylalkyl, and pharmaceutically acceptable salts, esters and prodrugs thereof.

In a further embodiment, the invention pertains to compounds wherein X is $CR^{6'}R^6$; $R^2$, $R^{2'}$, $R^6$, $R^{6'}$, $R^8$, $R^{10}$, $R^{11}$, and $R^{12}$ are each hydrogen; $R^4$ is $NR^{4'}R^{4''}$; $R^{4'}$ and $R^{4''}$ are lower alkyl; and $R^5$ is hydroxy or hydrogen.

In a further embodiment, $R^8$ is substituted phenyl, e.g., o-substituted phenyl, e.g., aminomethyl substituted phenyl. In a further embodiment, the 8-substituted tetracycline compound is:

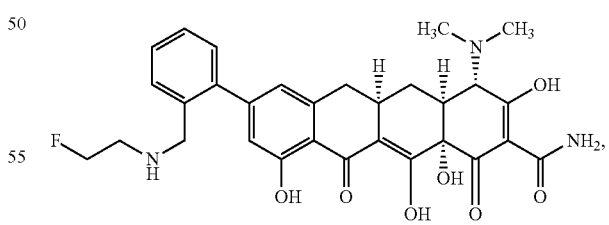

and pharmaceutically acceptable salts, esters, and prodrugs thereof.

In another further embodiment, $R^8$ is substituted pyridinyl, e.g., halo-substituted pyridinyl, e.g., 6-fluoro-pyridin-3-yl. In a further embodiment, $R^9$ is amino. In yet a further embodiment, the 8-substituted tetracycline compound is:

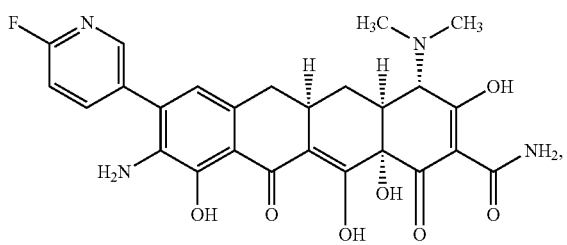 [SMILES: CN(C)[C@@H]1C(O)=C(C(N)=O)C(=O)[C@@]2(O)C(O)=C3C(=O)c4c(cc(-c5ccc(F)nc5)c(N)c4O)C[C@H]3C[C@@H]12]

and pharmaceutically acceptable salts, esters, and prodrugs thereof.

5. 13-Substituted Methacycline Compounds

In one embodiment, a 13-substituted tetracycline compound is of formula V:

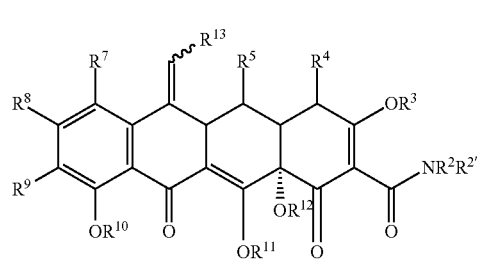

wherein:

$R^2$, $R^{4'}$, $R^{4''}$, $R^7$ and $R^{7''}$ are each hydrogen, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;

$R^4$ is $NR^{4'}R^{4''}$, alkyl, alkenyl, alkynyl, aryl, hydroxyl, halogen, or hydrogen;

$R^{2'}$, $R^3$, $R^{10}$, $R^{11}$ and $R^{12}$ are each hydrogen or a pro-drug moiety;

$R^5$ is hydroxyl, hydrogen, thiol, alkanoyl, aroyl, alkaroyl, aryl, heteroaromatic, alkyl, alkenyl, alkynyl, alkoxy, alkylthio, alkylsulfinyl, alkylsulfonyl, alkylamino, arylalkyl, alkyl carbonyloxy, or aryl carbonyloxy;

$R^7$ is hydrogen, hydroxyl, halogen, thiol, nitro, alkyl, alkenyl, alkynyl, aryl, alkoxy, alkylthio, alkylsulfinyl, alkylsulfonyl, arylalkyl, amino, arylalkenyl, arylalkynyl, acyl, aminoalkyl, heterocyclic, thionitroso, or $-(CH_2)_{0-3}(NR^{7c})_{0-1}C(=W')WR^{7a}$;

$R^8$ is substituted phenyl or substituted pyridinyl;

$R^9$ is hydrogen, hydroxyl, halogen, thiol, nitro, alkyl, alkenyl, alkynyl, aryl, alkoxy, alkylthio, alkylsulfinyl, alkylsulfonyl, arylalkyl, amino, arylalkenyl, arylalkynyl, acyl, aminoalkyl, heterocyclic, thionitroso, or $-(CH_2)_{0-3}NR^{9c}C(=Z')ZR^{9a}$;

$R^{7a}$, $R^{7b}$, $R^{7c}$, $R^{7d}$, $R^{7e}$, $R^{7f}$, $R^{9a}$, $R^{9b}$, $R^{9c}$, $R^{9d}$, $R^{9e}$, and $R^{8f}$ are each independently absent, hydrogen, acyl, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;

W is $CR^{7d}R^{7e}$, S, O or $NR^{7b}$;

W' is O, $NR^{7f}$, or S;

$R^{13}$ is 4-alkyl substituted phenyl, and pharmaceutically acceptable salts, esters and prodrugs thereof.

In a further embodiment, the invention pertains to compounds wherein $R^2$, $R^{2'}$, $R^8$, $R^{10}$, $R^{11}$, and $R^{12}$ are each hydrogen; $R^4$ is $NR^{4'}R^{4''}$; $R^{4'}$ and $R^{4''}$ are lower alkyl; and $R^5$ is hydroxy or hydrogen.

In a further embodiment, the phenyl $R^{13}$ group is substituted with an aminomethyl substituent. In another further embodiment, the aminomethyl substituent is dimethylaminomethyl. In another further embodiment, the invention pertains to compounds of the formula:

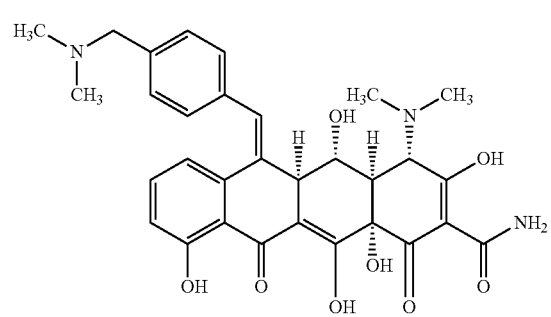 [SMILES: CN(C)Cc1ccc(/C=C2\c3cccc(O)c3C(=O)C3=C(O)[C@]4(O)C(=O)C(C(N)=O)=C(O)[C@@H](N(C)C)[C@@H]4[C@@H](O)[C@@H]32)cc1]

and pharmaceutically acceptable salts, esters, and prodrugs thereof.

In one embodiment, the tetracycline compounds of the invention do not include those described in U.S. Ser. Nos. 09/660,598, 09/823,884, 09/852,908, 10/819,343, 10/820,456, 09/894,805, 09/895,796, 09/895,812, 09/895,797, 09/895,857, 10/097,634, 10/759,484, 10/337,914, 10/636,437, 10/752,378, or 10/740,961. The entire contents of each of these applications are hereby incorporated herein in their entirety.

6. Methods for Synthesizing Tetracycline Compounds of the Invention

The tetracycline compounds of this invention can be synthesized using the methods described in the Schemes and/or by other techniques known to those of ordinary skill in the art.

The substituted tetracycline compounds of the invention can be synthesized using the methods described in the following schemes and by using art recognized techniques. All novel substituted tetracycline compounds described herein are included in the invention as compounds.

SCHEME 1

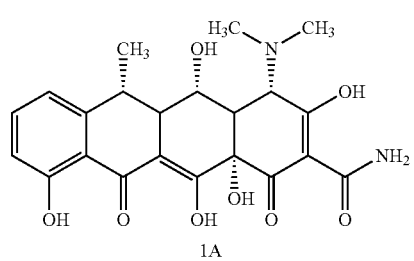 $\xrightarrow{\text{H}_2\text{SO}_4}{\text{NaNO}_3}$

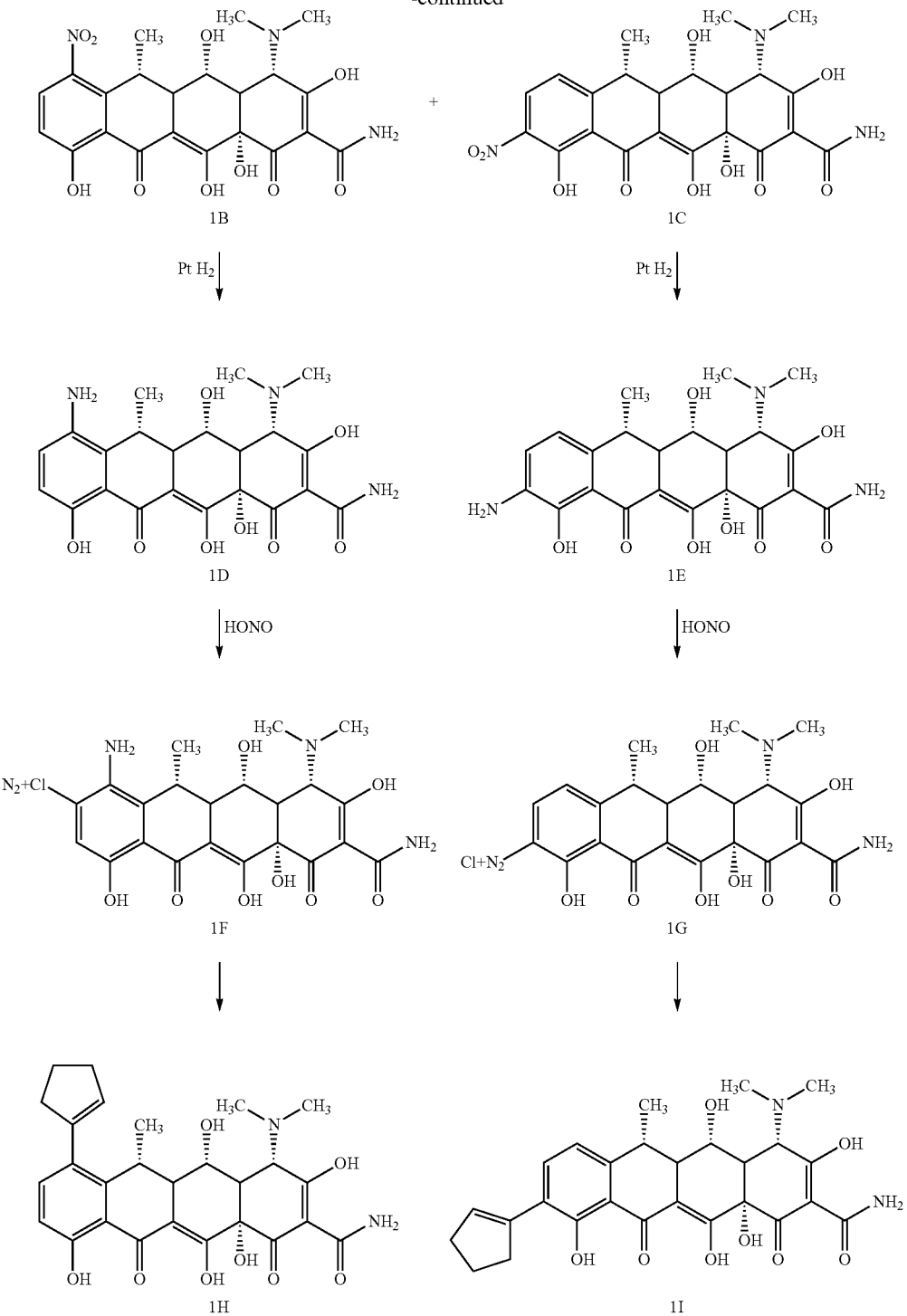

9- and 7-substituted tetracyclines can be synthesized by the method shown in Scheme 1. As shown in Scheme 1, 9- and 7-substituted tetracycline compounds can be synthesized by treating a tetracycline compound (e.g., doxycycline, 1A), with sulfuric acid and sodium nitrate. The resulting product is a mixture of the 7-nitro and 9-nitro isomers (1B and 1C, respectively). The 7-nitro (1B) and 9-nitro (1C) derivatives are treated by hydrogenation using hydrogen gas and a platinum catalyst to yield amines 1D and 1E. The isomers are separated at this time by conventional methods. To synthesize 7- or 9-substituted alkenyl derivatives, the 7- or 9-amino tetracycline compound (1E and 1F, respectively) is treated with HONO, to yield the diazonium salt (1G and 1H). The salt (1G and 1H) is treated with an appropriate reactive reagent to yield the desired compound (e.g., in Scheme 1,7-cyclopent-1-enyl doxycycline (1H) and 9-cyclopent-1-enyl doxycycline (1I)).

SCHEME 2

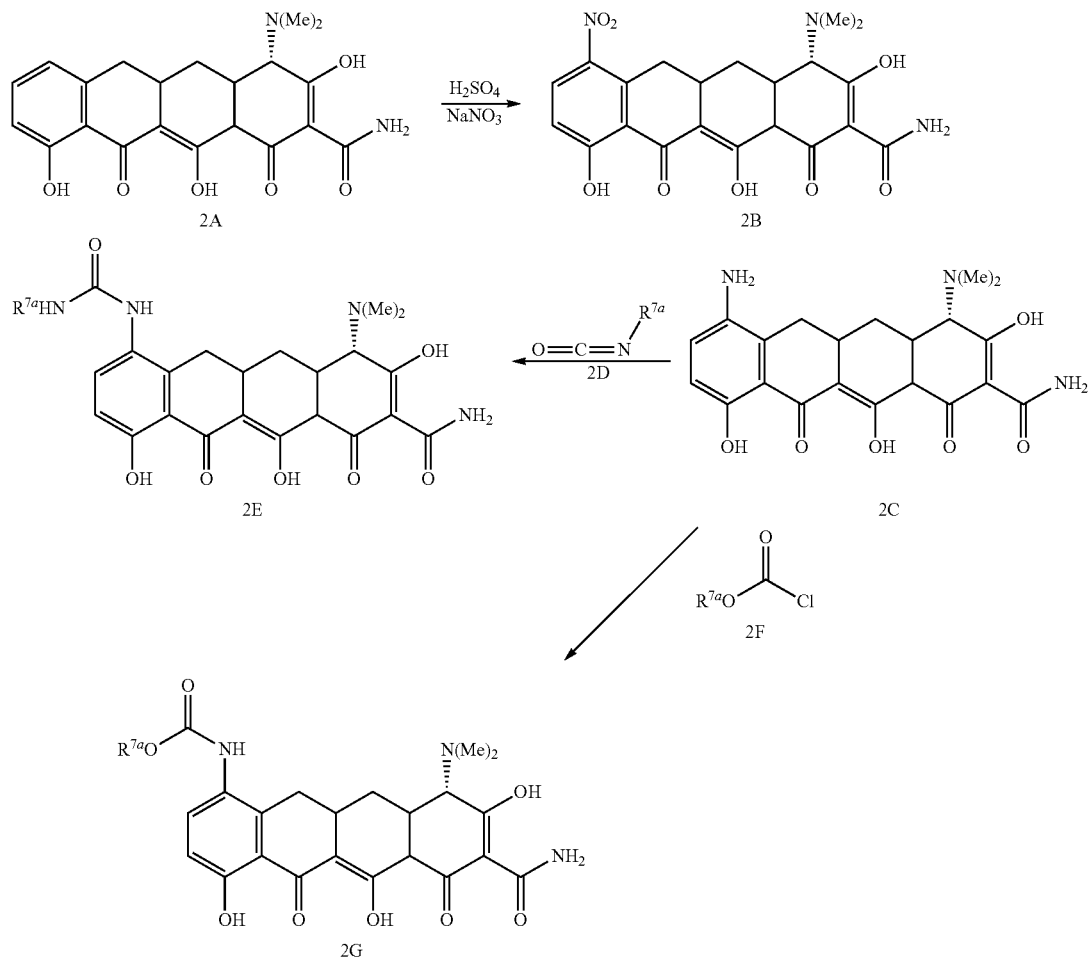

As shown in Scheme 2, tetracycline compounds of the invention wherein $R^7$ is a carbamate or a urea derivative can be synthesized using the following protocol. Sancycline (2A) is treated with $NaNO_2$ under acidic conditions forming 7-nitro sancycline (2B) in a mixture of positional isomers. 7-nitrosancycline (2B) is then treated with $H_2$ gas and a platinum catalyst to form the 7-amino sancycline derivative (2C). To form the urea derivative (2E), isocyanate (2D) is reacted with the 7-amino sancycline derivative (2C). To form the carbamate (2G), the appropriate acid chloride ester (2F) is reacted with 2C.

SCHEME 3

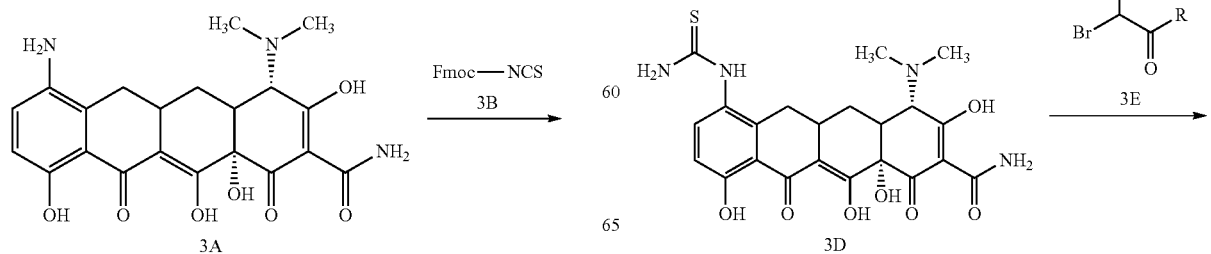

-continued

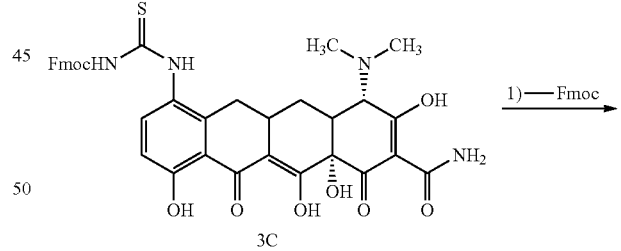

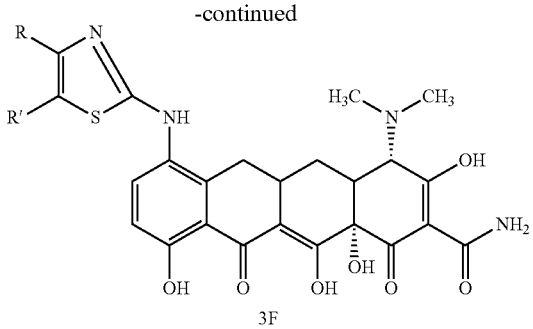

3F

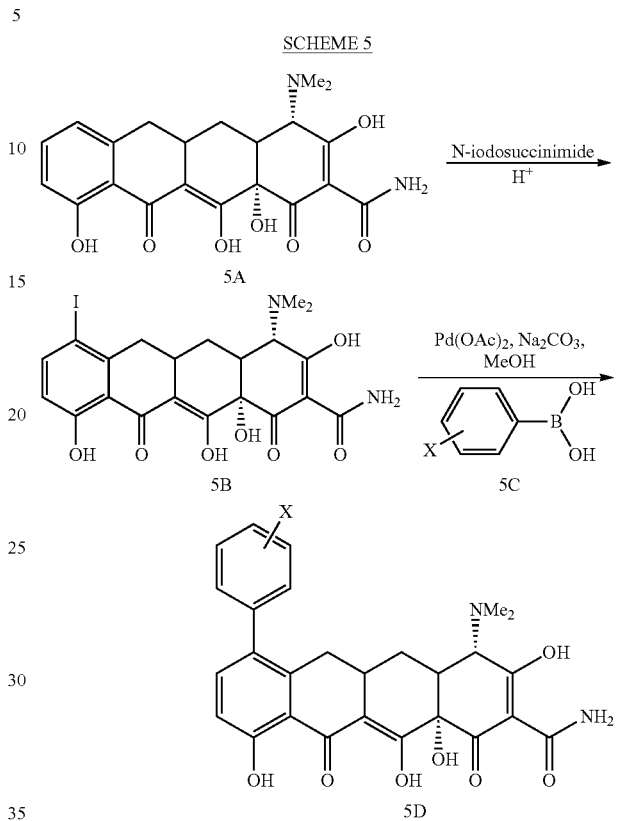

As shown in Scheme 3, tetracycline compounds of the invention, wherein R[7] is a heterocyclic (i.e. thiazole) substituted amino group can be synthesized using the above protocol. 7-amino sancycline (3A) is reacted with Fmoc-isothiocyanate (3B) to produce the protected thiourea (3C). The protected thiourea (3C) is then deprotected yielding the active sancycline thiourea (3D) compound. The sancycline thiourea (3D) is reacted with an α-haloketone (3E) to produce a thiazole substituted 7-amino sancycline (3F).

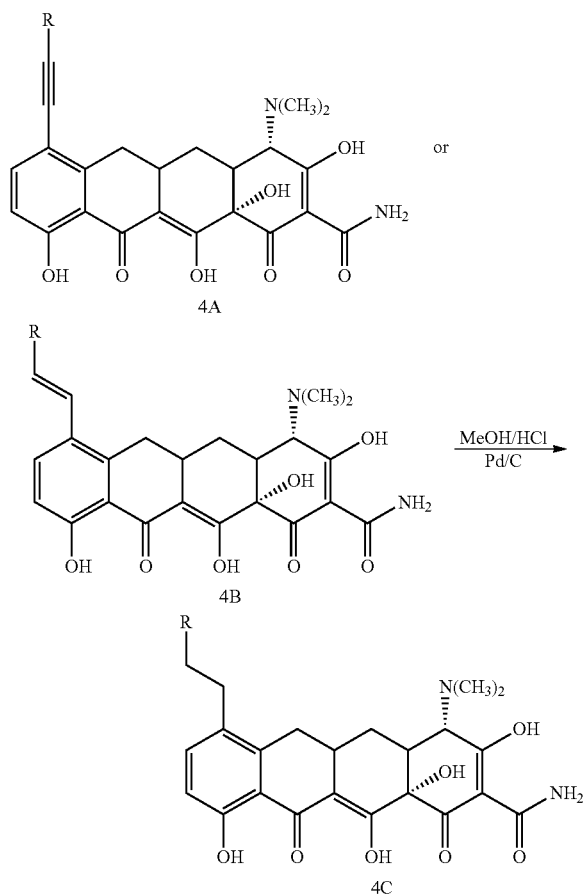

7-alkenyl tetracycline compounds, such as 7-alkynyl sancycline (4A) and 7-alkenyl sancycline (4B), can be hydrogenated to form 7-alkyl substituted tetracycline compounds (e.g., 7-alkyl sancycline, 4C). Scheme 4 depicts the selective hydrogenation of the 7-position double or triple bond, in saturated methanol and hydrochloric acid solution with a palladium/carbon catalyst under pressure, to yield the product.

In Scheme 5, a general synthetic scheme for synthesizing 7-position aryl derivatives is shown. A Suzuki coupling of an aryl boronic acid with an iodosancycline compound is shown. An iodo sancycline compound (5B) can be synthesized from sancycline by treating sancycline (5A) with at least one equivalent N-iodosuccinimide (NIS) under acidic conditions. The reaction is quenched, and the resulting 7-iodo sancycline (5B) can then be purified using standard techniques known in the art. To form the aryl derivative, 7-iodo sancycline (5B) is treated with an aqueous base (e.g., Na$_2$CO$_3$) and an appropriate boronic acid (5C) and under an inert atmosphere. The reaction is catalyzed with a palladium catalyst (e.g., Pd(OAc)$_2$). The product (5D) can be purified by methods known in the art (such as HPLC). Other 7-aryl, alkenyl, and alkynyl tetracycline compounds can be synthesized using similar protocols.

The 7-substituted tetracycline compounds of the invention can also be synthesized using Stille cross couplings. Stille cross couplings can be performed using an appropriate tin reagent (e.g., R—SnBu$_3$) and a halogenated tetracycline compound, (e.g., 7-iodosancycline). The tin reagent and the iodosancycline compound can be treated with a palladium catalyst (e.g., Pd(PPh$_3$)$_2$Cl$_2$ or Pd(AsPh$_3$)$_2$Cl$_2$) and, optionally, with an additional copper salt, e.g., CuI. The resulting compound can then be purified using techniques known in the art.

SCHEME 6

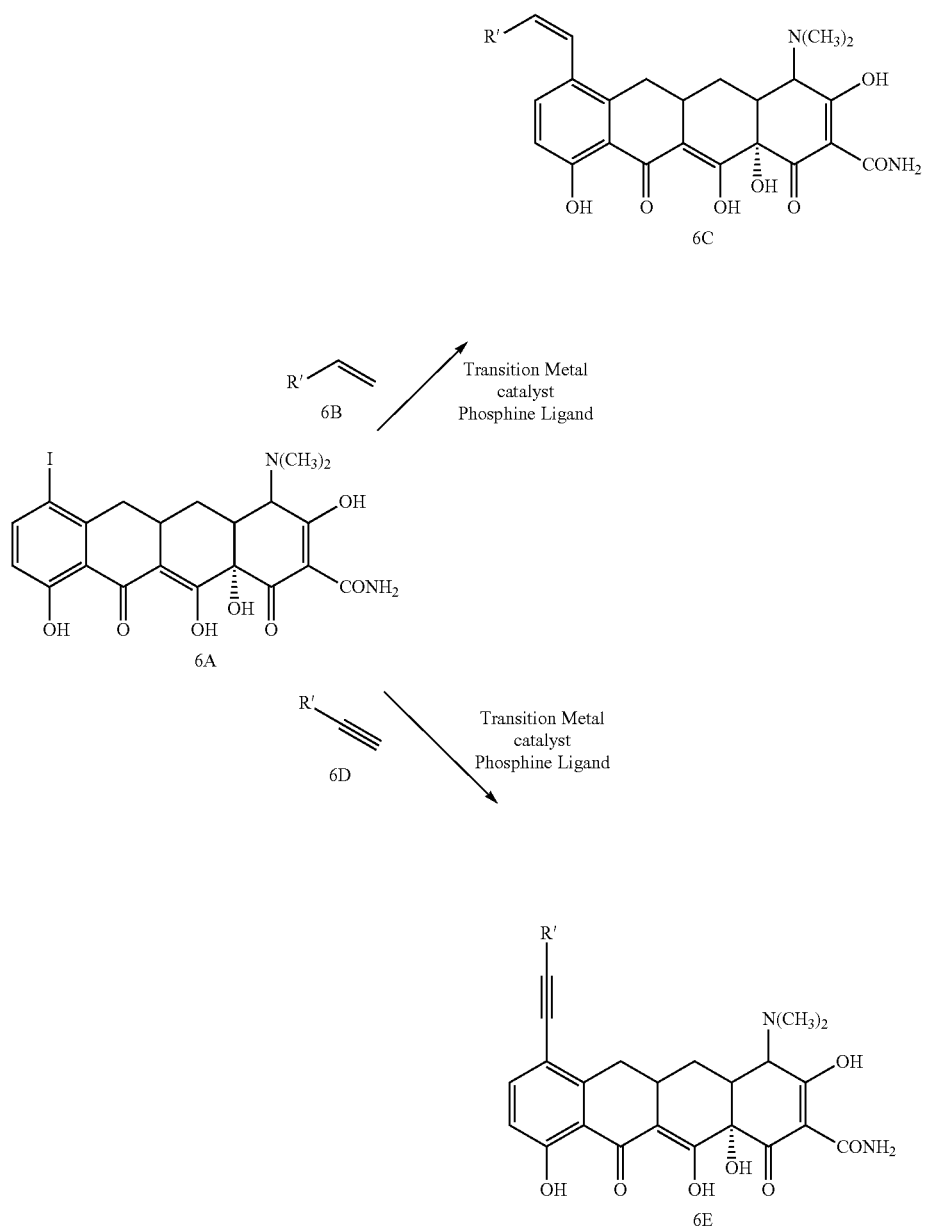

The compounds of the invention can also be synthesized using Heck-type cross coupling reactions. As shown in Scheme 6, Heck-type cross-couplings can be performed by suspending a halogenated tetracycline compound (e.g., 7-iodosancycline, 6A) and an appropriate palladium or other transition metal catalyst (e.g., Pd(OAc)$_2$ and CuI) in an appropriate solvent (e.g., degassed acetonitrile). The substrate, a reactive alkene (6B) or alkyne (6D), and triethylamine are then added and the mixture is heated for several hours, before being cooled to room temperature. The resulting 7-substituted alkenyl (6C) or 7-substituted alkynyl (6E) tetracycline compound can then be purified using techniques known in the art.

SCHEME 7

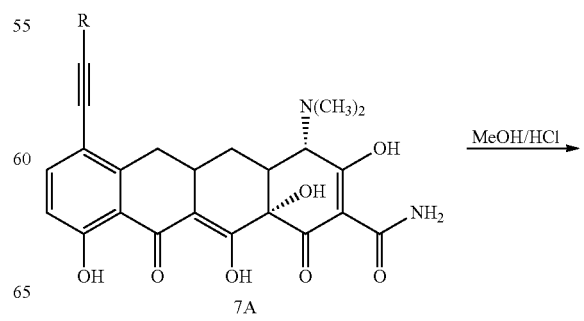

63

-continued

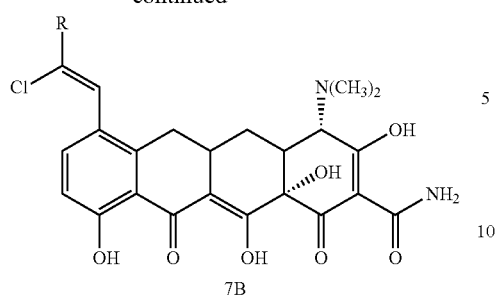

7B

64

-continued

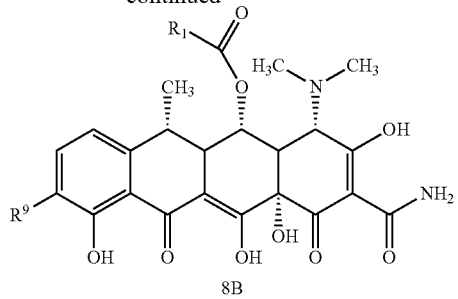

8B

To prepare 7-(2'-Chloro-alkenyl)-tetracycline compounds, the appropriate 7-(alkynyl)-sancycline (7A) is dissolved in saturated methanol and hydrochloric acid and stirred. The solvent is then removed to yield the product (7B).

As depicted in Scheme 8, 5-esters of 9-substituted tetracycline compounds can be formed by dissolving the 9-substituted compounds (8A) in strong acid (e.g. HF, methanesulphonic acid, and trifluoromethanesulfonic acid) and adding the appropriate carboxylic acid to yield the corresponding esters (8B).

As shown in Scheme 9 below, 7 and 9 aminomethyl tetracyclines may be synthesized using reagents such as hydroxymethyl-carbamic acid benzyl ester.

SCHEME 9

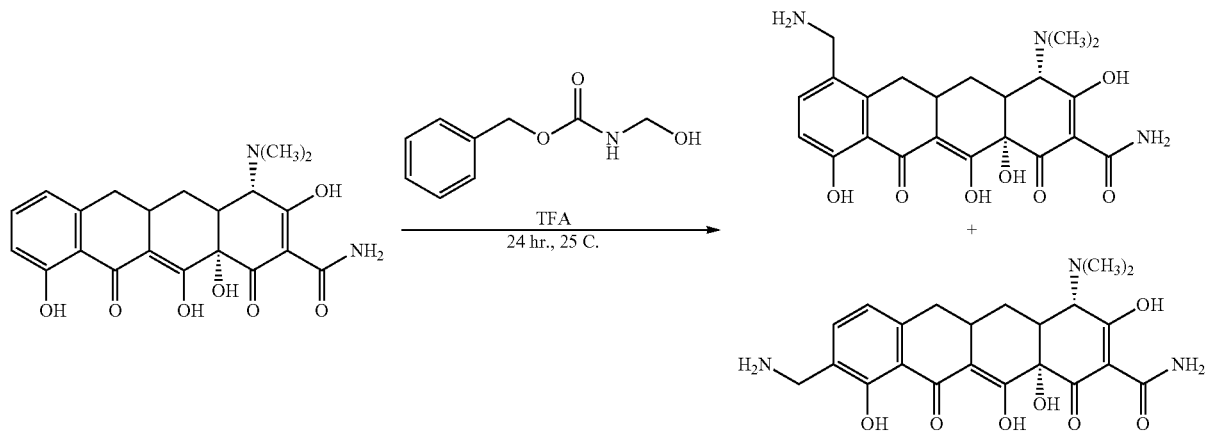

SCHEME 8

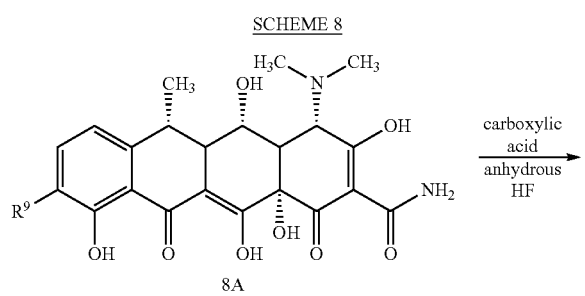

8A

The term "alkyl" includes saturated aliphatic groups, including straight-chain alkyl groups (e.g., methyl, ethyl, propyl, butyl, pentyl, hexyl, heptyl, octyl, nonyl, decyl, etc.), branched-chain alkyl groups (isopropyl, tert-butyl, isobutyl, etc.), cycloalkyl (alicyclic) groups (cyclopropyl, cyclopentyl, cyclohexyl, cycloheptyl, cyclooctyl), alkyl substituted cycloalkyl groups, and cycloalkyl substituted alkyl groups. The term alkyl further includes alkyl groups, which can further include oxygen, nitrogen, sulfur or phosphorous atoms replacing one or more carbons of the hydrocarbon backbone. In certain embodiments, a straight chain or branched chain alkyl has 6 or fewer carbon atoms in its backbone (e.g., $C_1$-$C_6$ for straight chain, $C_3$-$C_6$ for branched chain), and more preferably 4 or fewer. Likewise, preferred cycloalkyls have from 3-8 carbon atoms in their ring structure, and more preferably have 5 or 6 carbons in the ring structure. The term $C_1$-$C_6$ includes alkyl groups containing 1 to 6 carbon atoms.

Moreover, the term alkyl includes both "unsubstituted alkyls" and "substituted alkyls", the latter of which refers to alkyl moieties having substituents replacing a hydrogen on one or more carbons of the hydrocarbon backbone. Such substituents can include, for example, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Cycloalkyls can be further substituted, e.g., with the substituents described above. An "alkylaryl" or an "arylalkyl" moiety is an alkyl substituted with an aryl (e.g., phenylmethyl (benzyl)). The term "alkyl" also includes the side chains of natural and unnatural amino acids.

The term "aryl" includes groups, including 5- and 6-membered single-ring aromatic groups that may include from zero to four heteroatoms, for example, benzene, phenyl, pyrrole, furan, thiophene, thiazole, isothiaozole, imidazole, triazole, tetrazole, pyrazole, oxazole, isooxazole, pyridine, pyrazine, pyridazine, and pyrimidine, and the like. Furthermore, the term "aryl" includes multicyclic aryl groups, e.g., tricyclic, bicyclic, e.g., naphthalene, benzoxazole, benzodioxazole, benzothiazole, benzoimidazole, benzothiophene, methylenedioxyphenyl, quinoline, isoquinoline, napthridine, indole, benzofuran, purine, benzofuran, deazapurine, or indolizine. Those aryl groups having heteroatoms in the ring structure may also be referred to as "aryl heterocycles", "heterocycles," "heteroaryls" or "heteroaromatics". The aromatic ring can be substituted at one or more ring positions with such substituents as described above, as for example, halogen, hydroxyl, alkoxy, alkylcarbonyloxy, arylcarbonyloxy, alkoxycarbonyloxy, aryloxycarbonyloxy, carboxylate, alkylcarbonyl, alkylaminoacarbonyl, arylalkyl aminocarbonyl, alkenylaminocarbonyl, alkylcarbonyl, arylcarbonyl, arylalkylcarbonyl, alkenylcarbonyl, alkoxycarbonyl, aminocarbonyl, alkylthiocarbonyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings which are not aromatic so as to form a polycycle (e.g., tetralin).

The term "alkenyl" includes unsaturated aliphatic groups analogous in length and possible substitution to the alkyls described above, but that contain at least one double bond.

For example, the term "alkenyl" includes straight-chain alkenyl groups (e.g., ethylenyl, propenyl, butenyl, pentenyl, hexenyl, heptenyl, octenyl, nonenyl, decenyl, etc.), branched-chain alkenyl groups, cycloalkenyl (alicyclic) groups (cyclopropenyl, cyclopentenyl, cyclohexenyl, cycloheptenyl, cyclooctenyl), alkyl or alkenyl substituted cycloalkenyl groups, and cycloalkyl or cycloalkenyl substituted alkenyl groups. The term alkenyl further includes alkenyl groups which include oxygen, nitrogen, sulfur or phosphorous atoms replacing one or more carbons of the hydrocarbon backbone. In certain embodiments, a straight chain or branched chain alkenyl group has 6 or fewer carbon atoms in its backbone (e.g., $C_2$-$C_6$ for straight chain, $C_3$-$C_6$ for branched chain). Likewise, cycloalkenyl groups may have from 3-8 carbon atoms in their ring structure, and more preferably have 5 or 6 carbons in the ring structure. The term $C_2$-$C_6$ includes alkenyl groups containing 2 to 6 carbon atoms.

Moreover, the term alkenyl includes both "unsubstituted alkenyls" and "substituted alkenyls", the latter of which refers to alkenyl moieties having substituents replacing a hydrogen on one or more carbons of the hydrocarbon backbone. Such substituents can include, for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

The term "alkynyl" includes unsaturated aliphatic groups analogous in length and possible substitution to the alkyls described above, but which contain at least one triple bond.

For example, the term "alkynyl" includes straight-chain alkynyl groups (e.g., ethynyl, propynyl, butynyl, pentynyl, hexynyl, heptynyl, octynyl, nonynyl, decynyl, etc.), branched-chain alkynyl groups, and cycloalkyl or cycloalkenyl substituted alkynyl groups. The term alkynyl further includes alkynyl groups which include oxygen, nitrogen, sulfur or phosphorous atoms replacing one or more carbons of the hydrocarbon backbone. In certain embodiments, a straight chain or branched chain alkynyl group has 6 or fewer carbon atoms in its backbone (e.g., $C_2$-$C_6$ for straight chain, $C_3$-$C_6$ for branched chain). The term $C_2$-$C_6$ includes alkynyl groups containing 2 to 6 carbon atoms.

Moreover, the term alkynyl includes both "unsubstituted alkynyls" and "substituted alkynyls", the latter of which refers to alkynyl moieties having substituents replacing a hydrogen on one or more carbons of the hydrocarbon backbone. Such substituents can include, for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

Unless the number of carbons is otherwise specified, "lower alkyl" as used herein means an alkyl group, as defined above, but having from one to five carbon atoms in its backbone structure. "Lower alkenyl" and "lower alkynyl" have chain lengths of, for example, 2-5 carbon atoms.

The term "acyl" includes compounds and moieties which contain the acyl radical (CH₃CO—) or a carbonyl group. It includes substituted acyl moieties. The term "substituted acyl" includes acyl groups where one or more of the hydrogen atoms are replaced by for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

The term "acylamino" includes moieties wherein an acyl moiety is bonded to an amino group. For example, the term includes alkylcarbonylamino, arylcarbonylamino, carbamoyl and ureido groups.

The term "aroyl" includes compounds and moieties with an aryl or heteroaromatic moiety bound to a carbonyl group. Examples of aroyl groups include phenylcarboxy, naphthyl carboxy, etc.

The terms "alkoxyalkyl", "alkylaminoalkyl" and "thioalkoxyalkyl" include alkyl groups, as described above, which further include oxygen, nitrogen or sulfur atoms replacing one or more carbons of the hydrocarbon backbone, e.g., oxygen, nitrogen or sulfur atoms.

The term "alkoxy" includes substituted and unsubstituted alkyl, alkenyl, and alkynyl groups covalently linked to an oxygen atom. Examples of alkoxy groups include methoxy, ethoxy, isopropyloxy, propoxy, butoxy, and pentoxy groups. Examples of substituted alkoxy groups include halogenated alkoxy groups. The alkoxy groups can be substituted with groups such as alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties. Examples of halogen substituted alkoxy groups include, but are not limited to, fluoromethoxy, difluoromethoxy, trifluoromethoxy, chloromethoxy, dichloromethoxy, trichloromethoxy, etc.

The term "amine" or "amino" includes compounds where a nitrogen atom is covalently bonded to at least one carbon or heteroatom. The term includes "alkyl amino" which comprises groups and compounds wherein the nitrogen is bound to at least one additional alkyl group. The term "dialkyl amino" includes groups wherein the nitrogen atom is bound to at least two additional alkyl groups. The term "arylamino" and "diarylamino" include groups wherein the nitrogen is bound to at least one or two aryl groups, respectively. The term "alkylarylamino," "alkylaminoaryl" or "arylaminoalkyl" refers to an amino group which is bound to at least one alkyl group and at least one aryl group.

The term "alkaminoalkyl" refers to an alkyl, alkenyl, or alkynyl group bound to a nitrogen atom which is also bound to an alkyl group.

The term "amide," "amido" or "aminocarbonyl" includes compounds or moieties which contain a nitrogen atom which is bound to the carbon of a carbonyl or a thiocarbonyl group. The term includes "alkaminocarbonyl" or "alkylaminocarbonyl" groups which include alkyl, alkenyl, aryl or alkynyl groups bound to an amino group bound to a carbonyl group. It includes arylaminocarbonyl and arylcarbonylamino groups which include aryl or heteroaryl moieties bound to an amino group which is bound to the carbon of a carbonyl or thiocarbonyl group. The terms "alkylaminocarbonyl," "alkenylaminocarbonyl," "alkynylaminocarbonyl," "arylaminocarbonyl," "alkylcarbonylamino," "alkenylcarbonylamino," "alkynylcarbonylamino," and "arylcarbonylamino" are included in term "amide." Amides also include urea groups (aminocarbonylamino) and carbamates (oxycarbonylamino).

The term "carbonyl" or "carboxy" includes compounds and moieties which contain a carbon connected with a double bond to an oxygen atom. The carbonyl can be further substituted with any moiety which allows the compounds of the invention to perform its intended function. For example, carbonyl moieties may be substituted with alkyls, alkenyls, alkynyls, aryls, alkoxy, aminos, etc. Examples of moieties which contain a carbonyl include aldehydes, ketones, carboxylic acids, amides, esters, anhydrides, etc.

The term "thiocarbonyl" or "thiocarboxy" includes compounds and moieties which contain a carbon connected with a double bond to a sulfur atom.

The term "ether" includes compounds or moieties which contain an oxygen bonded to two different carbon atoms or heteroatoms. For example, the term includes "alkoxyalkyl" which refers to an alkyl, alkenyl, or alkynyl group covalently bonded to an oxygen atom which is covalently bonded to another alkyl group.

The term "ester" includes compounds and moieties which contain a carbon or a heteroatom bound to an oxygen atom which is bonded to the carbon of a carbonyl group. The term "ester" includes alkoxycarboxy groups such as methoxycarbonyl, ethoxycarbonyl, propoxycarbonyl, butoxycarbonyl, pentoxycarbonyl, etc. The alkyl, alkenyl, or alkynyl groups are as defined above.

The term "thioether" includes compounds and moieties which contain a sulfur atom bonded to two different carbon or hetero atoms. Examples of thioethers include, but are not limited to alkthioalkyls, alkthioalkenyls, and alkthioalkynyls. The term "alkthioalkyls" include compounds with an alkyl, alkenyl, or alkynyl group bonded to a sulfur atom which is bonded to an alkyl group. Similarly, the term "alkthioalkenyls" and alkthioalkynyls" refer to compounds or moieties wherein an alkyl, alkenyl, or alkynyl group is bonded to a sulfur atom which is covalently bonded to an alkynyl group.

The term "hydroxy" or "hydroxyl" includes groups with an —OH or

The term "halogen" includes fluorine, bromine, chlorine, iodine, etc. The term "perhalogenated" generally refers to a moiety wherein all hydrogens are replaced by halogen atoms.

The terms "polycyclyl" or "polycyclic radical" refer to two or more cyclic rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, alkylaminoacarbonyl, arylalkylaminocarbonyl, alkenylaminocarbonyl, alkylcarbonyl, arylcarbonyl, arylalkyl carbonyl, alkenylcarbonyl, aminocarbonyl, alkylthiocarbonyl, alkoxyl, phosphate, phosphonato, phosphinato, cyano, amido, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkyl, alkylaryl, or an aromatic or heteroaromatic moiety.

The term "heteroatom" includes atoms of any element other than carbon or hydrogen. Preferred heteroatoms are nitrogen, oxygen, sulfur and phosphorus.

The term "prodrug moiety" includes moieties which can be metabolized in vivo to a hydroxyl group and moieties which may advantageously remain esterified in vivo. Preferably, the prodrugs moieties are metabolized in vivo by esterases or by other mechanisms to hydroxyl groups or other advantageous groups. Examples of prodrugs and their uses are well known in the art (See, e.g., Berge et al. (1977) "Pharmaceutical Salts", *J. Pharm. Sci.* 66:1-19). The prodrugs can be prepared in situ during the final isolation and purification of the compounds, or by separately reacting the purified compound in its free acid form or hydroxyl with a suitable esterifying agent. Hydroxyl groups can be converted into esters via treatment with a carboxylic acid. Examples of prodrug moieties include substituted and unsubstituted, branch or unbranched lower alkyl ester moieties, (e.g., propionic acid esters), lower alkenyl esters, di-lower alkyl-amino lower-alkyl esters (e.g., dimethylaminoethyl ester), acylamino lower alkyl esters (e.g., acetyloxymethyl ester), acyloxy lower alkyl esters (e.g., pivaloyloxymethyl ester), aryl esters (phenyl ester), aryl-lower alkyl esters (e.g., benzyl ester), substituted (e.g., with methyl, halo, or methoxy substituents) aryl and aryl-lower alkyl esters, amides, lower-alkyl amides, di-lower alkyl amides, and hydroxy amides. Preferred prodrug moieties are propionoic acid esters and acyl esters.

It will be noted that the structure of some of the tetracycline compounds of this invention includes asymmetric carbon atoms. It is to be understood accordingly that the isomers arising from such asymmetry (e.g., all enantiomers and diastereomers) are included within the scope of this invention, unless indicated otherwise. Such isomers can be obtained in substantially pure form by classical separation techniques and by stereochemically controlled synthesis. Furthermore, the structures and other compounds and moieties discussed in this application also include all tautomers thereof.

7. Methods for Treating Tetracycline Responsive States

The invention also pertains to methods for treating a tetracycline responsive states in subjects, by administering to a subject an effective amount of a tetracycline compound of the invention (e.g., a compound of Formula I, II, III, IV, V or otherwise described herein), such that the tetracycline responsive state is treated.

The term "treating" includes curing as well as ameliorating at least one symptom of the state, disease or disorder, e.g., the tetracycline compound responsive state.

The language "tetracycline compound responsive state" or "tetracycline responsive state" includes states which can be treated, prevented, or otherwise ameliorated by the administration of a tetracycline compound of the invention, e.g., a 3, 10, and/or 12a substituted tetracycline compound. Tetracycline compound responsive states include bacterial, viral, and fungal infections (including those which are resistant to other tetracycline compounds), cancer (e.g., prostate, breast, colon, lung melanoma and lymph cancers and other disorders characterized by unwanted cellular proliferation, including, but not limited to, those described in U.S. Pat. No. 6,100,248), arthritis, osteoporosis, diabetes, and other states for which tetracycline compounds have been found to be active (see, for example, U.S. Pat. Nos. 5,789, 395; 5,834,450; 6,277,061 and 5,532,227, each of which is expressly incorporated herein by reference). Compounds of the invention can be used to prevent or control important mammalian and veterinary diseases such as diarrhea, urinary tract infections, infections of skin and skin structure, ear, nose and throat infections, wound infection, mastitis and the like. In addition, methods for treating neoplasms using tetracycline compounds of the invention are also included (van der Bozert et al., *Cancer Res.,* 48:6686-6690 (1988)). In a further embodiment, the tetracycline responsive state is not a bacterial infection. In another embodiment, the tetracycline compounds of the invention are essentially non-antibacterial. For example, non-antibacterial tetracycline compounds of the invention may have MIC values greater than about 4 µg/ml (as measured by assays known in the art and/or the assay given in Example 2).

Tetracycline compound responsive states also include inflammatory process associated states (IPAS). The term "inflammatory process associated state" includes states in which inflammation or inflammatory factors (e.g., matrix metalloproteinases (MMPs), nitric oxide (NO), TNF, interleukins, plasma proteins, cellular defense systems, cytokines, lipid metabolites, proteases, toxic radicals, adhesion molecules, etc.) are involved or are present in an area in aberrant amounts, e.g., in amounts which may be advantageous to alter, e.g., to benefit the subject. The inflammatory process is the response of living tissue to damage. The cause of inflammation may be due to physical damage, chemical substances, micro-organisms, tissue necrosis, cancer or other agents. Acute inflammation is short-lasting, lasting only a few days. If it is longer lasting however, then it may be referred to as chronic inflammation.

IPAF's include inflammatory disorders. Inflammatory disorders are generally characterized by heat, redness, swelling, pain and loss of function. Examples of causes of inflammatory disorders include, but are not limited to, microbial infections (e.g., bacterial and fungal infections), physical agents (e.g., burns, radiation, and trauma), chemical agents (e.g., toxins and caustic substances), tissue necrosis and various types of immunologic reactions.

Examples of inflammatory disorders include, but are not limited to, osteoarthritis, rheumatoid arthritis, acute and chronic infections (bacterial and fungal, including diphtheria and pertussis); acute and chronic bronchitis, sinusitis, and upper respiratory infections, including the common cold; acute and chronic gastroenteritis and colitis; acute and chronic cystitis and urethritis; acute and chronic dermatitis; acute and chronic conjunctivitis; acute and chronic serositis (pericarditis, peritonitis, synovitis, pleuritis and tendinitis); uremic pericarditis; acute and chronic cholecystis; acute and chronic vaginitis; acute and chronic uveitis; drug reactions; insect bites; burns (thermal, chemical, and electrical); and sunburn.

Tetracycline compound responsive states also include NO associated states. The term "NO associated state" includes states which involve or are associated with nitric oxide (NO) or inducible nitric oxide synthase (iNOS). NO associated state includes states which are characterized by aberrant amounts of NO and/or iNOS. Preferably, the NO associated state can be treated by administering tetracycline compounds of the invention, e.g., a 3, 10, and/or 12a substituted tetracycline compound. The disorders, diseases and states described in U.S. Pat. Nos. 6,231,894; 6,015,804; 5,919,774; and 5,789,395 are also included as NO associated states. The entire contents of each of these patents are hereby incorporated herein by reference.

Other examples of NO associated states include, but are not limited to, malaria, senescence, diabetes, vascular stroke, neurodegenerative disorders (Alzheimer's disease & Huntington's disease), cardiac disease (reperfusion-associated injury following infarction), juvenile diabetes, inflammatory disorders, osteoarthritis, rheumatoid arthritis, acute, recurrent and chronic infections (bacterial, viral and fungal); acute and chronic bronchitis, sinusitis, and respiratory infections, including the common cold; acute and chronic gastroenteritis and colitis; acute and chronic cystitis and urethritis; acute and chronic dermatitis; acute and chronic conjunctivitis; acute and chronic serositis (pericarditis, peritonitis, synovitis, pleuritis and tendonitis); uremic pericarditis; acute and chronic cholecystis; cystic fibrosis, acute and chronic vaginitis; acute and chronic uveitis; drug reactions; insect bites; burns (thermal, chemical, and electrical); and sunburn.

The term "inflammatory process associated state" also includes, in one embodiment, matrix metalloproteinase associated states (MMPAS). MMPAS include states charachterized by abberrant amounts of MMPs or MMP activity. These are also include as tetracycline compound responsive states which may be treated using compounds of the invention, e.g., 3, 10, and/or 12a substituted tetracycline compounds.

Examples of matrix metalloproteinase associated states ("MMPAS's") include, but are not limited to, arteriosclerosis, corneal ulceration, emphysema, osteoarthritis, multiple sclerosis (Liedtke et al., *Ann. Neurol.* 1998, 44:35-46; Chandler et al., *J. Neuroimmunol.* 1997, 72:155-71), osteosarcoma, osteomyelitis, bronchiectasis, chronic pulmonary obstructive disease, skin and eye diseases, periodontitis, osteoporosis, rheumatoid arthritis, ulcerative colitis, inflammatory disorders, tumor growth and invasion (Stetler-Stevenson et al., *Annu. Rev. Cell Biol.* 1993, 9:541-73; Tryggvason et al., *Biochim. Biophys. Acta* 1987, 907:191-217; Li et al., *Mol. Carcinog.* 1998, 22:84-89)), metastasis, acute lung injury, stroke, ischemia, diabetes, aortic or vascular aneurysms, skin tissue wounds, dry eye, bone and cartilage degradation (Greenwald et al., *Bone* 1998, 22:33-38; Ryan et al., *Curr. Op. Rheumatol.* 1996, 8; 238-247). Other MMPAS include those described in U.S. Pat. Nos. 5,459,135; 5,321,017; 5,308,839; 5,258,371; 4,935,412; 4,704,383, 4,666,897, and RE 34,656, incorporated herein by reference in their entirety.

In another embodiment, the tetracycline compound responsive state is cancer. Examples of cancers which the tetracycline compounds of the invention may be useful to treat include all solid tumors, i.e., carcinomas e.g., adenocarcinomas, and sarcomas. Adenocarcinomas are carcinomas derived from glandular tissue or in which the tumor cells form recognizable glandular structures. Sarcomas broadly include tumors whose cells are embedded in a fibrillar or homogeneous substance like embryonic connective tissue. Examples of carcinomas which may be treated using the methods of the invention include, but are not limited to, carcinomas of the prostate, breast, ovary, testis, lung, colon, and breast. The methods of the invention are not limited to the treatment of these tumor types, but extend to any solid tumor derived from any organ system. Examples of treatable cancers include, but are not limited to, colon cancer, bladder cancer, breast cancer, melanoma, ovarian carcinoma, prostatic carcinoma, lung cancer, and a variety of other cancers as well. The methods of the invention also cause the inhibition of cancer growth in adenocarcinomas, such as, for example, those of the prostate, breast, kidney, ovary, testes, and colon.

In an embodiment, the tetracycline responsive state of the invention is cancer. The invention pertains to a method for treating a subject suffering or at risk of suffering from cancer, by administering an effective amount of a substituted tetracycline compound, such that inhibition cancer cell growth occurs, i.e., cellular proliferation, invasiveness, metastasis, or tumor incidence is decreased, slowed, or stopped. The inhibition may result from inhibition of an inflammatory process, down-regulation of an inflammatory process, some other mechanism, or a combination of mechanisms. Alternatively, the tetracycline compounds may be useful for preventing cancer recurrence, for example, to treat residual cancer following surgical resection or radiation therapy. The tetracycline compounds useful according to the invention are especially advantageous as they are substantially non-toxic compared to other cancer treatments. In a further embodiment, the compounds of the invention are administered in combination with standard cancer therapy, such as, but not limited to, chemotherapy.

Examples of tetracycline responsive states also include neurological disorders which include both neuropsychiatric and neurodegenerative disorders, but are not limited to, such as Alzheimer's disease, dementias related to Alzheimer's disease (such as Pick's disease), Parkinson's and other Lewy diffuse body diseases, senile dementia, Huntington's disease, Gilles de la Tourette's syndrome, multiple sclerosis, amylotrophic lateral sclerosis (ALS), progressive supranuclear palsy, epilepsy, and Creutzfeldt-Jakob disease; autonomic function disorders such as hypertension and sleep disorders, and neuropsychiatric disorders, such as depression, schizophrenia, schizoaffective disorder, Korsakoff's psychosis, mania, anxiety disorders, or phobic disorders; learning or memory disorders, e.g., amnesia or age-related memory loss, attention deficit disorder, dysthymic disorder, major depressive disorder, mania, obsessive-compulsive disorder, psychoactive substance use disorders, anxiety, phobias, panic disorder, as well as bipolar affective disorder, e.g., severe bipolar affective (mood) disorder (BP-1), bipolar affective neurological disorders, e.g., migraine and obesity. Further neurological disorders include, for example, those listed in the American Psychiatric Association's Diagnostic and Statistical manual of Mental Disorders (DSM), the most current version of which is incorporated herein by reference in its entirety.

Other examples of tetracycline compound responsive states are described in WO 03/005971A2, U.S. Ser. No. 60/421,248, and U.S. Ser. No. 60/480,482, each incorporated herein by reference.

The language "in combination with" another therapeutic agent or treatment includes co-administration of the tetracycline compound, (e.g., inhibitor) and with the other therapeutic agent or treatment, administration of the tetracycline compound first, followed by the other therapeutic agent or treatment and administration of the other therapeutic agent or treatment first, followed by the tetracycline compound. The other therapeutic agent may be any agent which is known in the art to treat, prevent, or reduce the symptoms of an IPAS. Furthermore, the other therapeutic agent may be any agent of benefit to the patient when administered in combination with the administration of an tetracycline compound. In one embodiment, the cancers treated by methods of the invention include those described in U.S. Pat. Nos. 6,100,248; 5,843,925; 5,837,696; or 5,668,122, incorporated herein by reference in their entirety.

In another embodiment, the tetracycline compound responsive state is diabetes, e.g., juvenile diabetes, diabetes mellitus, diabetes type I, or diabetes type II. In a further embodiment, protein glycosylation is not affected by the administration of the tetracycline compounds of the invention. In another embodiment, the tetracycline compound of the invention is administered in combination with standard diabetic therapies, such as, but not limited to insulin therapy. In a further embodiment, the IPAS includes disorders described in U.S. Pat. Nos. 5,929,055; and 5,532,227, incorporated herein by reference in their entirety.

In another embodiment, the tetracycline compound responsive state is a bone mass disorder. Bone mass disorders include disorders where a subjects bones are disorders and states where the formation, repair or remodeling of bone is advantageous. For examples bone mass disorders include osteoporosis (e.g., a decrease in bone strength and density), bone fractures, bone formation associated with surgical procedures (e.g., facial reconstruction), osteogenesis imperfecta (brittle bone disease), hypophosphatasia, Paget's disease, fibrous dysplasia, osteopetrosis, myeloma bone disease, and the depletion of calcium in bone, such as that which is related to primary hyperparathyroidism. Bone mass disorders include all states in which the formation, repair or remodeling of bone is advantageous to the subject as well as all other disorders associated with the bones or skeletal system of a subject which can be treated with the tetracycline compounds of the invention. In a further embodiment, the bone mass disorders include those described in U.S. Pat. Nos. 5,459,135; 5,231,017; 5,998,390; 5,770,588; RE 34,656; 5,308,839; 4,925,833; 3,304,227; and 4,666,897, each of which is hereby incorporated herein by reference in its entirety.

In another embodiment, the tetracycline compound responsive state is acute lung injury. Acute lung injuries include adult respiratory distress syndrome (ARDS), post-pump syndrome (PPS), and trauma. Trauma includes any injury to living tissue caused by an extrinsic agent or event. Examples of trauma include, but are not limited to, crush injuries, contact with a hard surface, or cutting or other damage to the lungs.

The invention also pertains to a method for treating acute lung injury by administering a substituted tetracycline compound of the invention.

The tetracycline responsive states of the invention also include chronic lung disorders. The invention pertains to methods for treating chronic lung disorders by administering a tetracycline compound, such as those described herein. The method includes administering to a subject an effective amount of a substituted tetracycline compound such that the chronic lung disorder is treated. Examples of chronic lung disorders include, but are not limited, to asthma, cystic fibrosis, and emphesema. In a further embodiment, the tetracycline compounds of the invention used to treat acute and/or chronic lung disorders such as those described in U.S. Pat. Nos. 5,977,091; 6,043,231; 5,523,297; and 5,773,430, each of which is hereby incorporated herein by reference in its entirety.

In yet another embodiment, the tetracycline compound responsive state is ischemia, stroke, or ischemic stroke. The invention also pertains to a method for treating ischemia, stroke, or ischemic stroke by administering an effective amount of a substituted tetracycline compound of the invention. In a further embodiment, the tetracycline compounds of the invention are used to treat such disorders as described in U.S. Pat. Nos. 6,231,894; 5,773,430; 5,919,775 or 5,789,395, incorporated herein by reference.

In another embodiment, the tetracycline compound responsive state is a skin wound. The invention also pertains, at least in part, to a method for improving the healing response of the epithelialized tissue (e.g., skin, mucusae) to acute traumatic injury (e.g., cut, burn, scrape, etc.). The method may include using a tetracycline compound of the invention (which may or may not have antibacterial activity) to improve the capacity of the epithelialized tissue to heal acute wounds. The method may increase the rate of collagen accumulation of the healing tissue. The method may also decrease the proteolytic activity in the epthithelialized tissue by decreasing the collagenolytic and/or gellatinolytic activity of MMPs. In a further embodiment, the tetracycline compound of the invention is administered to the surface of the skin (e.g., topically). In a further embodiment, the tetracycline compound of the invention used to treat a skin wound, and other such disorders as described in, for example, U.S. Pat. Nos. 5,827,840; 4,704,383; 4,935,412; 5,258,371; 5,308,8391 5,459,135; 5,532,227; and 6,015,804; each of which is incorporated herein by reference in its entirety.

In yet another embodiment, the tetracycline compound responsive state is an aortic or vascular aneurysm in vascular tissue of a subject (e.g., a subject having or at risk of having an aortic or vascular aneurysm, etc.). The tetracycline compound may by effective to reduce the size of the vascular aneurysm or it may be administered to the subject prior to the onset of the vascular aneurysm such that the aneurysm is prevented. In one embodiment, the vascular tissue is an artery, e.g., the aorta, e.g., the abdominal aorta. In a further embodiment, the tetracycline compounds of the invention are used to treat disorders described in U.S. Pat. Nos. 6,043,225 and 5,834,449, incorporated herein by reference in their entirety.

Bacterial infections may be caused by a wide variety of gram positive and gram negative bacteria. The compounds of the invention are useful as antibiotics against organisms which are resistant to other tetracycline compounds. The antibiotic activity of the tetracycline compounds of the invention may be determined using the method discussed in Example 2, or by using the in vitro standard broth dilution method described in Waitz, J. A., *National Commission for Clinical Laboratory Standards, Document M7-A2*, vol. 10, no. 8, pp. 13-20, $2^{nd}$ edition, Villanova, Pa. (1990).

The tetracycline compounds may also be used to treat infections traditionally treated with tetracycline compounds such as, for example, rickettsiae; a number of gram-positive and gram-negative bacteria; and the agents responsible for lymphogranuloma venereum, inclusion conjunctivitis, psittacosis. The tetracycline compounds may be used to treat infections of, e.g., *K. pneumoniae, Salmonella, E. hirae, A. baumanii, B. catarrhalis, H. influenzae, P. aeruginosa, E. faecium, E. coli, S. aureus* or *E. faecalis*. In one embodiment, the tetracycline compound is used to treat a bacterial infection that is resistant to other tetracycline antibiotic compounds. The tetracycline compound of the invention may be administered with a pharmaceutically acceptable carrier.

The language "effective amount" of the compound is that amount necessary or sufficient to treat or prevent a tetracycline compound responsive state. The effective amount can vary depending on such factors as the size and weight of the subject, the type of illness, or the particular tetracycline compound. For example, the choice of the tetracycline compound can affect what constitutes an "effective amount". One of ordinary skill in the art would be able to study the aforementioned factors and make the determination regarding the effective amount of the tetracycline compound without undue experimentation.

The invention also pertains to methods of treatment against microorganism infections and associated diseases. The methods include administration of an effective amount of one or more tetracycline compounds to a subject. The subject can be either a plant or, advantageously, an animal, e.g., a mammal, e.g., a human.

In the therapeutic methods of the invention, one or more tetracycline compounds of the invention may be administered alone to a subject, or more typically a compound of the invention will be administered as part of a pharmaceutical composition in mixture with conventional excipient, i.e., pharmaceutically acceptable organic or inorganic carrier substances suitable for parenteral, oral or other desired administration and which do not deleteriously react with the active compounds and are not deleterious to the recipient thereof.

7. Pharmaceutical Compositions of the Invention

The invention also pertains to pharmaceutical compositions comprising a therapeutically effective amount of a tetracycline compound (e.g., a compound of Formula I, II, III, IV, V or any other compound described herein) and, optionally, a pharmaceutically acceptable carrier.

The language "pharmaceutically acceptable carrier" includes substances capable of being coadministered with the tetracycline compound(s), and which allow both to perform their intended function, e.g., treat or prevent a tetracycline responsive state. Suitable pharmaceutically acceptable carriers include but are not limited to water, salt solutions, alcohol, vegetable oils, polyethylene glycols, gelatin, lactose, amylose, magnesium stearate, talc, silicic acid, viscous paraffin, perfume oil, fatty acid monoglycerides and diglycerides, petroethral fatty acid esters, hydroxymethyl-cellulose, polyvinylpyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously react with the active compounds of the invention.

The tetracycline compounds of the invention that are basic in nature are capable of forming a wide variety of salts with various inorganic and organic acids. The acids that may be used to prepare pharmaceutically acceptable acid addition salts of the tetracycline compounds of the invention that are basic in nature are those that form non-toxic acid addition salts, i.e., salts containing pharmaceutically acceptable anions, such as the hydrochloride, hydrobromide, hydroiodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and palmoate [i.e., 1,1'-methylene-bis-(2-hydroxy-3-naphthoate)] salts. Although such salts must be pharmaceutically acceptable for administration to a subject, e.g., a mammal, it is often desirable in practice to initially isolate a tetracycline compound of the invention from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent, such as methanol or ethanol. Upon careful evaporation of the solvent, the desired solid salt is readily obtained. The preparation of other tetracycline compounds of the invention not specifically described in the foregoing experimental section can be accomplished using combinations of the reactions described above that will be apparent to those skilled in the art.

The preparation of other tetracycline compounds of the invention not specifically described in the foregoing experimental section can be accomplished using combinations of the reactions described above that will be apparent to those skilled in the art.

The tetracycline compounds of the invention that are acidic in nature are capable of forming a wide variety of base salts. The chemical bases that may be used as reagents to prepare pharmaceutically acceptable base salts of those tetracycline compounds of the invention that are acidic in nature are those that form non-toxic base salts with such compounds. Such non-toxic base salts include, but are not limited to those derived from such pharmaceutically acceptable cations such as alkali metal cations (e.g., potassium and sodium) and alkaline earth metal cations (e.g., calcium and magnesium), ammonium or water-soluble amine addition salts such as N-methylglucamine-(meglumine), and the lower alkanolammonium and other base salts of pharmaceutically acceptable organic amines. The pharmaceutically acceptable base addition salts of tetracycline compounds of the invention that are acidic in nature may be formed with pharmaceutically acceptable cations by conventional methods. Thus, these salts may be readily prepared by treating the tetracycline compound of the invention with an aqueous solution of the desired pharmaceutically acceptable cation and evaporating the resulting solution to dryness, preferably under reduced pressure. Alternatively, a lower alkyl alcohol solution of the tetracycline compound of the invention may be mixed with an alkoxide of the desired metal and the solution subsequently evaporated to dryness.

The preparation of other tetracycline compounds of the invention not specifically described in the foregoing experimental section can be accomplished using combinations of the reactions described above that will be apparent to those skilled in the art.

The tetracycline compounds of the invention and pharmaceutically acceptable salts thereof can be administered via either the oral, parenteral or topical routes. In general, these compounds are most desirably administered in effective dosages, depending upon the weight and condition of the subject being treated and the particular route of administration chosen. Variations may occur depending upon the species of the subject being treated and its individual response to said medicament, as well as on the type of pharmaceutical formulation chosen and the time period and interval at which such administration is carried out.

The pharmaceutical compositions of the invention may be administered alone or in combination with other known compositions for treating tetracycline responsive states in a subject, e.g., a mammal. Preferred mammals include pets (e.g., cats, dogs, ferrets, etc.), farm animals (cows, sheep, pigs, horses, goats, etc.), lab animals (rats, mice, monkeys, etc.), and primates (chimpanzees, humans, gorillas). The language "in combination with" a known composition is intended to include simultaneous administration of the composition of the invention and the known composition, administration of the composition of the invention first, followed by the known composition and administration of the known composition first, followed by the composition of the invention. Any of the therapeutically composition known in the art for treating tetracycline responsive states can be used in the methods of the invention.

The tetracycline compounds of the invention may be administered alone or in combination with pharmaceutically acceptable carriers or diluents by any of the routes previously mentioned, and the administration may be carried out in single or multiple doses. For example, the novel therapeutic agents of this invention can be administered advantageously in a wide variety of different dosage forms, i.e., they may be combined with various pharmaceutically acceptable inert carriers in the form of tablets, capsules, lozenges, troches, hard candies, powders, sprays (e.g., aerosols, etc.), creams, salves, suppositories, jellies, gels, pastes, lotions, ointments, aqueous suspensions, injectable solutions, elixirs, syrups, and the like. Such carriers include solid diluents or fillers, sterile aqueous media and various non-toxic organic solvents, etc. Moreover, oral pharmaceutical compositions can be suitably sweetened and/or flavored. In general, the therapeutically-effective compounds of this invention are present in such dosage forms at concentration levels ranging from about 5.0% to about 70% by weight.

For oral administration, tablets containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelatin and *acacia*. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof. The compositions of the invention may be formulated such that the tetracycline compositions are released over a period of time after administration.

For parenteral administration (including intraperitoneal, subcutaneous, intravenous, intradermal or intramuscular injection), solutions of a therapeutic compound of the present invention in either sesame or peanut oil or in aqueous propylene glycol may be employed. The aqueous solutions should be suitably buffered (preferably pH greater than 8) if necessary and the liquid diluent first rendered isotonic. These aqueous solutions are suitable for intravenous injection purposes. The oily solutions are suitable for intraarticular, intramuscular and subcutaneous injection purposes. The preparation of all these solutions under sterile conditions is readily accomplished by standard pharmaceutical techniques well known to those skilled in the art. For parenteral application, examples of suitable preparations include solutions, preferably oily or aqueous solutions as well as suspensions, emulsions, or implants, including suppositories. Therapeutic compounds may be formulated in sterile form in multiple or single dose formats such as being dispersed in a fluid carrier such as sterile physiological saline or 5% saline dextrose solutions commonly used with injectables.

Additionally, it is also possible to administer the compounds of the present invention topically when treating inflammatory conditions of the skin. Examples of methods of topical administration include transdermal, buccal or sublingual application. For topical applications, therapeutic compounds can be suitably admixed in a pharmacologically inert topical carrier such as a gel, an ointment, a lotion or a cream. Such topical carriers include water, glycerol, alcohol, propylene glycol, fatty alcohols, triglycerides, fatty acid esters, or mineral oils. Other possible topical carriers are liquid petrolatum, isopropylpalmitate, polyethylene glycol, ethanol 95%, polyoxyethylene monolauriate 5% in water, sodium lauryl sulfate 5% in water, and the like. In addition, materials such as anti-oxidants, humectants, viscosity stabilizers and the like also may be added if desired.

For enteral application, particularly suitable are tablets, dragees or capsules having talc and/or carbohydrate carrier binder or the like, the carrier preferably being lactose and/or corn starch and/or potato starch. A syrup, elixir or the like can be used wherein a sweetened vehicle is employed. Sustained release compositions can be formulated including those wherein the active component is protected with differentially degradable coatings, e.g., by microencapsulation, multiple coatings, etc.

In addition to treatment of human subjects, the therapeutic methods of the invention also will have significant veterinary applications, e.g. for treatment of livestock such as cattle, sheep, goats, cows, swine and the like; poultry such as chickens, ducks, geese, turkeys and the like; horses; and pets such as dogs and cats. Also, the compounds of the invention may be used to treat non-animal subjects, such as plants.

It will be appreciated that the actual preferred amounts of active compounds used in a given therapy will vary according to the specific compound being utilized, the particular compositions formulated, the mode of application, the particular site of administration, etc. Optimal administration rates for a given protocol of administration can be readily ascertained by those skilled in the art using conventional dosage determination tests conducted with regard to the foregoing guidelines.

In general, compounds of the invention for treatment can be administered to a subject in dosages used in prior tetracycline therapies. See, for example, the *Physicians' Desk Reference*. For example, a suitable effective dose of one or more compounds of the invention will be in the range of from 0.01 to 100 milligrams per kilogram of body weight of recipient per day, preferably in the range of from 0.1 to 50 milligrams per kilogram body weight of recipient per day, more preferably in the range of 1 to 20 milligrams per kilogram body weight of recipient per day. The desired dose is suitably administered once daily, or several sub-doses, e.g. 2 to 5 sub-doses, are administered at appropriate intervals through the day, or other appropriate schedule.

It will also be understood that normal, conventionally known precautions will be taken regarding the administration of tetracyclines generally to ensure their efficacy under normal use circumstances. Especially when employed for therapeutic treatment of humans and animals in vivo, the practitioner should take all sensible precautions to avoid conventionally known contradictions and toxic effects.

Thus, the conventionally recognized adverse reactions of gastrointestinal distress and inflammations, the renal toxicity, hypersensitivity reactions, changes in blood, and impairment of absorption through aluminum, calcium, and magnesium ions should be duly considered in the conventional manner.

Furthermore, the invention also pertains to the use of a tetracycline compound of formula I, II, III, IV, V, or any other compound described herein, for the preparation of a medicament. The medicament may include a pharmaceutically acceptable carrier and the tetracycline compound is an effective amount, e.g., an effective amount to treat a tetracycline responsive state.

EXEMPLIFICATION OF THE INVENTION

Example 1

Synthesis of Selected Compounds of the Invention

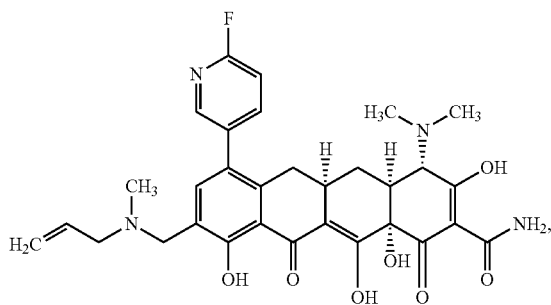 [SMILES: C=CCN(C)Cc1cc(-c2ccc(F)nc2)c2c(c1O)C(=O)C1=C(O)[C@]3(O)C(=O)C(C(N)=O)=C(O)[C@@H](N(C)C)[C@@H]3C[C@@H]1C2]

The above compound was prepared from 7-iodo-sancycline (15.0 g, 22.9 mmol) combined with Pd(dppf)$_2$Cl$_2$ (1.7 g, 2.29 mmol) and DMF (300 mL) in a 1 L round bottom 2 neck flask. Na$_2$CO$_3$ (7.2 g, 68.2 mmol) was dissolved in water (15 mL) was added to reaction solution. 2-fluoropyridine-5-boronic acid (6.4 g, 45.9 mmol) was dissolved in DMF (25 mL) and also added to reaction solution. Reaction mixture was stirred at 65° C. (oil bath temperature) under an argon atmosphere and reaction was monitored by HPLC and LC/MS. Reaction shown to be complete within 3 hr. Filtered through celite and evaporated solvent in vacuo. Redissolved in MeOH (30 mL) and precipitated in MTBE (3 L) to produce a yellow precipitate. Filtered and dried under vacuum overnight to yield 15 g of yellow powder. This crude material (9 g, 17.8 mmol) was dissolved in TFA/Triflic acid (83 mL/7 mL) and cooled to 0° C. using an ice bath. N-iodo-succinimide (8 g, 35.6 mmol) was added portion-wise to reaction solution over 2 hr. Reaction complete after 3 hrs—and 20% more NIS added to reaction. Evaporated TFA in vacuo and precipitated remaining acid in MTBE (1.4 L) at room temp. Yellow precipitate. Filtered and dried under vacuum overnight to yield 8.4 g of crude product. This crude material (4 g, 6.3 mmol) was combined with NaOAc (0.52 g, 6.3 mmol) in an oven-dried 250 mL 2 neck round bottom flask. Anhydrous DMF (60 mL) was syringed into reaction flask. Stirred under argon at room temp 1 hr. Diluted with more anhydrous DMF (120 mL) and a CO-filled balloon was placed on top neck of reaction flask. CO was purged through reaction direction from lecture bottle for 15 min. Flask open to CO-filled balloon and allowed to stir at 60° C. (oil bath temp) while Pd(PPh$_3$)$_4$ (2.2 g, 1.9 mmol) was added as a DMF slurry via syringe. Stirred at temperature 1 hr. SnBu$_3$H (1.6 g, 6.3 mmol) was added via syringe pump over 2 hr. Reaction monitored by HPLC and LC/MS and shown to be complete upon completion of tin addition. Evaporated solvent in vacuo. Purified by preparative HPLC in 20% yield in preparation for final synthesis step. This purified material (0.25 g, 0.46 mmol) was combined with anhydrous DMF (15 mL) in an oven-dried 100 mL flask. InCl$_3$(0.005 g, 0.023 mmol), N-methyl-allylamine (0.17 g, 0.23 mmol) were added to reaction and stirred at room temperature under argon 1 hr. NaCNBH$_3$ (0.035 g, 0.55 mmol) was added to reaction solution and was monitored by HPLC and LC/NIS. Reaction 80% complete within 6 hrs of reaction time. Evaporated solvent in vacuo. Final product was isolated by preparative HPLC in 10% yield as a yellow solid. ESI-MS: m/z (M+H) 593.

7-Ethyl-9-(4',4'-Difluoro-N-Piperidinyl methyl)-Sancycline

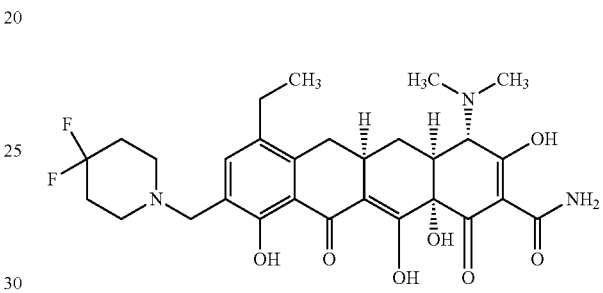

The compound was prepared from 7-ethyl-9-formyl-sancycline (0.23 g, 0.49 mmol) combined with InCl$_3$ (0.011 g, 0.049 mmol), 4,4-difluoropiperidine.HCl (0.17 g, 0.98 mmol), Et$_3$N (0.099 g, 0.98 mmol), and DMF (8 mL) in a glass vial. Stirred under argon at room temperature 30 min. NaCNBH$_3$ (0.043 g, 0.69 mmol) was added to reaction vial and continued to stir at room temperature under argon. Reaction was monitored by LC/MS and HPLC and shown to be complete in 2 hrs. Quenched reaction with MeOH (15 mL) and evaporated solvent in vacuo. Product was isolated by preparative HPLC in 20% yield as a yellow solid. ESI-MS: m/z (M+H) 576.

7-(Trifluoroalkenyl)-9-(2'-trans-2-methyl-2-butene) aminomethyl Sancycline

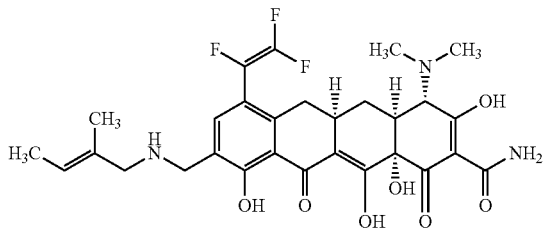 [SMILES: C/C=C(\C)CNCc1cc(C(F)=C(F)F)c2c(c1O)C(=O)C1=C(O)[C@]3(O)C(=O)C(C(N)=O)=C(O)[C@@H](N(C)C)[C@@H]3C[C@@H]1C2]

To a stirred solution of powered Zn (5.00 g, 76.5 mmol) in dry THF (50.0 mL) at 0 C was added iodo-trifluor alkene (2.00 mL, 4.50 g, 21.0 mmol) slowly over a 0.5 h time period. The reaction was stirred for an additional 1.5 h before it was filtered under an inert atmosphere and reduced of all solvent using rotary evaporation (25.0 C, 5.00 mm Hg) to yield the trifluoro-zinc-iodo-alkene reagent (approximately 3 mL). Dry DMF (10 mL) was added to the above zinc-reagent and this solution was added to a stirred solution of 7-Iodo-9-trans-2-methyl-2-butene sancycline free base (1.00 g, 1.57 mmol) and tetrakis(triphenylphosphine)palladium (0.181 g, 0.156 mmol) in dry DMF (10 mL). The contents were heated to 40 C and allowed to stir for 20 minutes. The reaction was then filtered and purified using reverse phase HPLC to give 7-trifluoroalkene sancycline product (557 mg, 0.0942 mmol, 60% yield) LCMS m/z=592.2392 (M+H).

7-(2'-Pyrazinyl)-9-(3',3',3'-Trifluoro-propylamino)-methyl-Sancycline

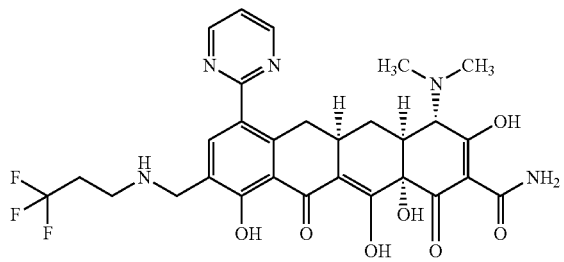 [SMILES: CN(C)[C@@H]1C(O)=C(C(N)=O)C(=O)[C@@]2(O)C(O)=C3C(=O)c4c(O)c(CNCCC(F)(F)F)cc(-c5ncccn5)c4C[C@H]3C[C@@H]12]

Step 1:
7-Iodo-9-aminomethyl sancycline (569 mg, 1 mmol), indium trichloride (22 mg, 0.1 mmol) and trifluoropropionaldehyde (224 μL, 2 mmol) were taken in DMF (25 mL) and stirred at room temperature for 10 minutes. To this solution, sodium triacetoxyborohydride (635 mg, 3 mmol) was added at once and the reaction mixture was stirred at room temperature for another 30 minutes. Progress of the reaction was monitored by HPLC and LC/MS. Reaction was completed in 30 minutes. DMF was then removed and the crude material obtained was then precipitated using diethyl ether/MeOH (100/10 mL). Filteration of the precipitate gave a yellow powder, which was used for the next step without further purification.

Step 2:
7-Iodo-9-(3,3,3-trifluoro-propylamino)-methyl-sancycline (665 mg, 1 mmol), Pd(PPh$_3$)$_4$ (115 mg, 0.1 mmol), Pd(OAc)$_2$ (22 mg, 0.1 mmol), CuI (19 mg, 0.1 mmol) were taken in anhydrous DMF (30 mL) and purged with argon for 5 minutes. To this solution, 2-pyrazine-stannane (738 mg, 2 mmol) was added and the reaction mixture was stirred at room temperature for 2 hours. Reaction was completed by then (monitored by HPLC/LCMS). It was then filtered through celite, washed with 5 mL of methanol. Solvent was evaporated to dryness. The crude material obtained was purified using preparative HPLC. A yellow solid was obtained after evaporating the fractions, which was converted to its HCl salt using MeOH/HCl solution. LC-MS (M+1 618).

7-Amino-9-Iodo-Doxycycline

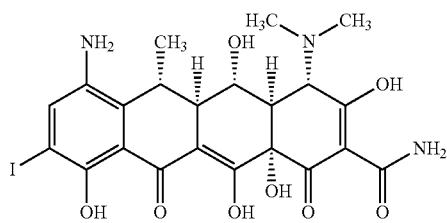 [SMILES: C[C@H]1c2c(N)cc(I)c(O)c2C(=O)C2=C(O)[C@]3(O)C(=O)C(C(N)=O)=C(O)[C@@H](N(C)C)[C@@H]3[C@@H](O)[C@@H]21]

To 500 mg of 9-iodo-doxycycline in 10 ml of methanesulfonic acid was added 1.1 eq. of sodium nitrate. The reaction mixture was left stirring for several hrs and was monitored by analytical HPLC. The intermediate (9-Iodo-7-nitro-doxycycline) was isolated by diluting the solution with ice-water, adjusting the pH with sodium hydroxide (pH ~4) and extracting the product with n-butanol. The solvent was evaporated under reduced pressure and the crude material was subjected to hydrogenation using 10% Pd/C in methanol. The final product was obtained via preparative HPLC. The LCMS showed the desired material; MS: 586. The structure was confirmed by NMR.

7-(Dimethylamino)-9-(4',4'-Difluoropiperdinl)-Doxycycline

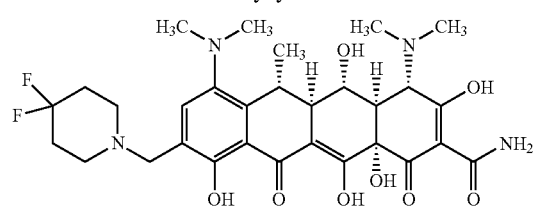

To a solution of 105 mg (0.16 mmol) of 9-(4-difluoropiperdinyl)-doxycycline dihydrochloride in 10 mL of methanesulfonic acid at room temperature, was added 19.4 mg (0.19 mmol) of potassium nitrate dissolved in 4 mL of methanesulfonic acid. The reaction was monitored by LCMS. After 30 minutes, the reaction mixture was poured over ice and diluted to 160 mL with ice water. The solution was loaded onto a 2.5×1 cm column of divinylbenzene resin (1000 angstrom, 5-25 μm) equilibrated with water. The crude reaction mixture was washed with excess water to remove methanesulfonic acid followed an excess of 1N ammonium acetate to neutralize the crude mixture. The excess ammonium acetate was removed by a water wash and the crude compound was purified by elution with 40% methanol in water with 0.1% HCl. The purified material was evaporated to dryness to yield 70 mg of 9-(4-difluoropiperdinyl)-7-nitro-doxycycline as the dihydrochloride salt (Yield=63%). LCMS (MH+) 623. To 70 mg (0.10 mmol) of 9-(4-difluoropiperdinyl)-7-nitro-doxycycline dihydrochloride in 20 mL of methoxyethanol was added 200 mL of sulfuric acid and 162 mL (2 mmol) of 37% formaldehyde in water. The reaction mixture was purged with Argon gas and 40 mg of 10% wet Palladium on carbon was added with stirring. The reaction was hydrogenated at room temperature and 760 torr hydrogen gas for 12 hours. The crude reaction was passed through Celite and evaporated to dryness. The crude reaction mixture was purified by preparative HPLC (1 inch×25 cm, Phenomenex Luna C18, 10 mm, Gradient 5-40% B buffer, A=water+0.1% TFA, B=acetonitrile+0.1% TFA, detection at 280 nm) to yield 20 mg of the product as the dihydrochloride salt (Yield=30%). LCMS (MH+) 621.

7-Diethylamino-9-(4'-Fluoro-N-Piperidinyl methyl)-Sancycline

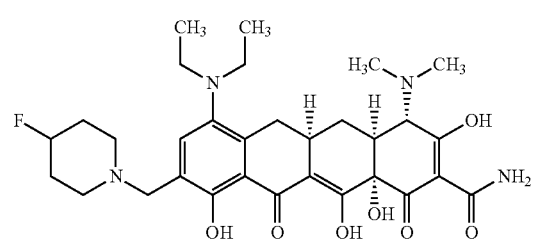 [SMILES: CCN(CC)c1cc(CN2CCC(F)CC2)c(O)c2c1C[C@H]1C[C@H]3[C@H](N(C)C)C(O)=C(C(N)=O)C(=O)[C@@]3(O)C(O)=C1C2=O]

7-NH$_2$-sancycline (4.0 g, 9.32 mmol) was combined with 2-methoxyethanol (100 mL), H$_2$SO$_4$ (5 mL of 1N solution) in a 2-neck 250 mL round bottom flask. Acetaldehyde (5.2 mL, 9.32 mmol) was added to reaction solution and contents were stirred at room temperature under argon for 20 minutes. Pd/C (1.25 g) was added to reaction and contents were evacuated/flushed with argon 3 times. A balloon filled with H$_2$ was placed on top neck of reaction flask and reaction solution was evacuated/flushed with H$_2$ three times. The reaction was stirred overnight under H$_2$ pressure at room temperature. The reaction was monitored by HPLC and LC/MS and shown to be complete by morning. The mixture was filtered through celite and solvent evaporated in vacuo. The residue was redissolved in water (1 L) and the pH was adjusted with Et$_3$N to pH~5. The mixture was filtered again through celite and loaded onto a DVB column. The compound eluted at 15% CH$_3$CN. Clean fractions were evaporated and dried overnight under vacuum. A yellow/brown solid (7-diethylamino sancycline) was isolated in 40% yield.

7-diethylamino sancycline (1.4 g, 2.88 mmol) was dissolved in TFA/Triflic acid (22 mL/6 mL) in a 100 mL flask. N-iodosuccinimide (1.2 g, 5.78 mmol) was added portionwise to reaction solution every 20 minutes. The reaction monitored by HPLC and LC/MS and shown to be complete within 3 hours. The reaction solution was diluted with H$_2$O (0.1% TFA) (30 mL) and the solvent was evaporated. The residue was redissolved in H$_2$O (100 mL) and loaded onto a 5 g DVB cartridge. The crude product eluted at 30-50% CH$_3$CN. A yellow/brown crude product was isolated in 90% yield.

This crude material, 7-diethylamino-9-iodo-sancycline, (1.8 g, 2.95 mmol) was dissolved in anhydrous DMF (100 mL) in a 2 neck 1 L round bottom flask and placed under argon. NaOAc (0.61 g, 7.36 mmol) was added to reaction solution and stirred at room temperature 45 min. Pd(PPh$_3$)$_4$ (1.02 g, 8.85 mmol) was added to reaction and a CO-filled balloon was placed on top neck of reaction flask. CO was bubbled through reaction solution for 10 min. then flask opened to CO balloon. SnBu$_3$H (0.8 g, 2.95 mmol) was added via syringe pump to reaction solution over 1 hour while heating to 65° C. (oil bath temperature). The reaction was monitored by LC/MS and shown to be complete upon addition of tin hydride. H$_2$O (0.1% TFA, 0.3 L) was added to the reaction flask and a precipitate formed. The mixture was filtered through celite and the filtrate was evaporated in vacuo. A brown solid in 90% yield (crude material) was isolated.

7-diethylamino-9-formyl-sancycline (0.25 g, 0.49 mmol) was dissolved in DMF (10 mL). InCl$_3$ (0.01 g, 0.049 mmol), 4-fluoropiperidine.HCl (0.15 g, 0.98 mmol), and Et$_3$N (0.09 g, 0.98 mmol) were added to reaction solution. The reaction was stirred at room temperature under argon 45 minutes. NaCNBH$_3$ (0.043 g, 0.68 mmol) was added to the reaction and it was monitored by HPLC and LC/MS. The reaction was shown to be complete in 3 hours and it was quenched with MeOH (30 mL). The final product was isolated by preparative HPLC in 10% yield as a yellow solid. ESI-MS: m/z (M+H) 601.

Synthesis of 7-Aminomethyl Doxycycline

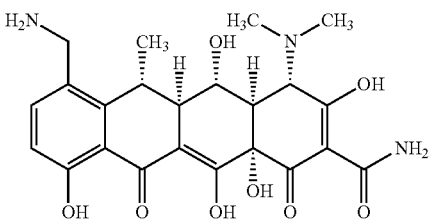 [SMILES: C[C@H]1c2c(CN)ccc(O)c2C(=O)C2=C(O)[C@]3(O)C(=O)C(C(N)=O)=C(O)[C@@H](N(C)C)[C@@H]3[C@@H](O)[C@@H]21]

To 1 gram of 9-tert-butyl-doxycycline, dissolved in 15 ml of methanesulfonic acid, was added an excess of HMBC (Hydroxymethyl-carbamic acid benzyl ester). The reaction mixture was monitored by analytical HPLC. The LCMS showed MS: 530 corresponding to the desired material, 7-aminomethyl-9-t-butyl doxycycline. The product was isolated via preparative HPLC and the structure confirmed by NMR. Removal of the t-butyl in triflic acid afforded the 7-aminomethyl doxycycline in good yield.

Synthesis of 9-(3',3',3'-Trifluoropropylamino)methyl Minocycline

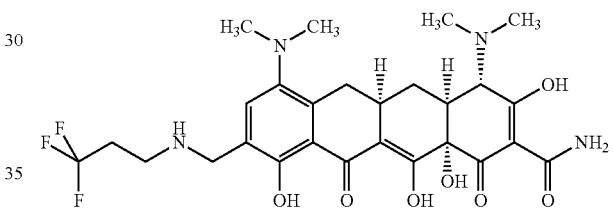

9-formyl-minocycline (0.2 g, 0.42 mmol) was combined with InCl$_3$ (0.01 g, 0.005 mmol), 3,3,3-trifluoropropylamine.HCl (0.25 g, 1.7 mmol), Et$_3$N (0.17 g, 1.7 mmol), and DMF (10 mL) in a glass vial. The reaction was stirred at room temperature under argon for 1 hour. NaCNBH$_3$ (0.032 g, 0.50 mmol) was added to reaction solution and was monitored by HPLC and LC/MS. The reaction was complete within 1 hour, quenched with MeOH (20 mL) and the solvent evacuated in vacuo. The final product was isolated by preparative HPLC in 25% yield as a yellow solid. ESI-MS: m/z (M+H) 583.

9-(4'-Difluoromethylene-N-piperidinyl) methyl Minocycline

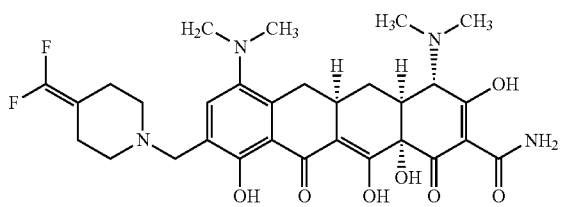 [SMILES: CN(C)c1cc(CN2CCC(=C(F)F)CC2)c(O)c2c1C[C@H]1C[C@H]3[C@H](N(C)C)C(O)=C(C(N)=O)C(=O)[C@@]3(O)C(O)=C1C2=O]

Anhydrous tetrahydrofuran (THF, 200 mL) was placed in a flame-dried 500 mL round bottom flask at 0° C. in an ice bath. Dibromodifluoromethane (97%, Aldrich, 10.00 mL, 106.19 mmol, 4.3 eq.) was added via syringe. Ten minutes later, Hexamethylphosphorous triamide (HMPT, 97%, Aldrich, 19.50 mL, 104.07 mmol, 4.2 eq.) was added dropwise. The clear solution turned milky white and was stirred for 1 hour at 0° C. A solution of tert-Butyl 4-oxo-1-piperidinecarboxylate (98%, Aldrich, 5.00 g, 24.59 mmol, 1.0 eq.) in anhydrous THF (50 mL) was then added dropwise via syringe at 0° C. and the solution was allowed to warm up slowly to room temperature over 1 hour by removing the ice bath. The powdered zinc (99.998%, Aldrich, powdered, −100 mesh, 6.56 g, 98.34 mmol, 4.0 eq.) was then added followed by HMPT (1.15 mL, 6.14 mmol, 25%) and the reaction mixture was refluxed for 3 hours. Water (250 mL) and Diethyl ether ($Et_2O$, 250 mL) were added and the mixture was extracted with $Et_2O$ (3 times 100 mL). The combined organic layers were washed with a saturated solution of Copper(II) sulfate ($CuSO_4$) in Water (150 mL) then with water (150 mL). The organic layer was dried over Magnesium sulfate ($MgSO_4$), filtered, and evaporated under reduced pressure to yield the desired fluorinated piperidine as a yellow oil, which was used without further purification in the next step.

A 100 mL round bottom flask equipped with a magnetic stirring bar was loaded with the BOC-protected piperidine (2.00 g, 8.57 mmol, 1.0 eq.) in a saturated HCl solution in Methanol (50 mL) at room temperature. The mixture was then stirred at 40° C. for 30 minutes and the solvent was evaporated under reduced pressure to a minimal volume. The HCl salt was then precipitated from $Et_2O$, filtered, and dried in vacuo to yield the desired fluorinated piperidine (1.10 g, 6.49 mmol, 76% yield) as a beige solid used without further purification in the next step.

A flame-dried 50 mL round bottom flask equipped with a magnetic stirring bar was loaded with 9-Formyl-minocycline (500 mg, 1.03 mmol, 1.0 eq.) in anhydrous Dimethylformamide (DMF, 10.00 mL) at room temperature. Indium chloride ($InCl_3$, 99.999%, Aldrich, 59 mg, 0.27 mmol, 26%) was added and the reaction mixture was stirred at 30° C. for 10 minutes. The amine (350 mg, 2.06 mmol, 2.0 eq.) was added in anhydrous DMF (2 mL), followed by Triethylamine ($NEt_3$, 99.5%, Alfa-Aesar, 290 µL, 2.08 mmol, 2.0 eq.). The mixture was then stirred at 30° C. for 1 hour and Sodium triacetoxyborohydride ($NaBH(OAc)_3$, 95%, Aldrich, 220 mg, 1.04 mmol, 1.0 eq.) was added followed by more $NEt_3$ (300 µL). After 2 hours, the reaction was done and the solvent evaporated under reduced pressure. The residue was purified by preparative HPLC (Acetonitrile/Water/0.1% Trifluoroacetic acid gradient) to yield the desired product as a yellow solid. MS m/z 603.

Synthesis of 9-(4'-Fluoro-N-Piperdinyl) methyl Doxycycline

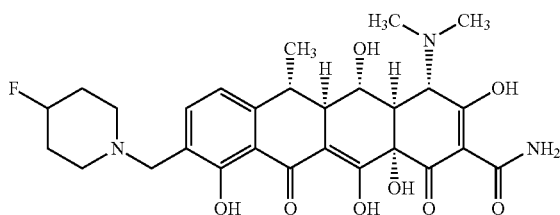 [SMILES: C[C@H]1c2ccc(CN3CCC(F)CC3)c(O)c2C(=O)C2=C(O)[C@]3(O)C(=O)C(C(N)=O)=C(O)[C@@H](N(C)C)[C@@H]3[C@@H](O)[C@@H]21]

The compound was prepared from Doxycycline (2.5 g, 5.0 mmol) dissolved in MeOH (anhydrous) (25 mL) and combined with $AgSO4$ (3.7 g, 11 mmol) and $I_2$ (3.1 g, 11 mmol) in a 100 mL round bottom flask. $H_2SO_{4conc}$ (2 drops) was added to the reaction solution and stirred at room temperature under argon for 1 hour. The reaction solution turned bright yellow after 30 minutes and the reaction was monitored by LC/MS and shown to be complete in 1 hour. Sodium sulfite (sat) (8 mL) was added to the reaction solution and a thick yellow precipitate was formed. The mixture was stirred at room temperature for 20 minutes. The mixture was diluted with $CH_3CN$ (75 mL), filtered through celite and evaporated solvent in vacuo to yield 1.7 g of crude 9-iodo-doxycycline material.

9-iodo-doxycycline (1.3 g, 2.4 mmol) was dissolved in anhydrous DMF (20 mL) in a 200 mL 2 neck round bottom flask and $Pd(PPh_3)_4$ (0.82 g, 0.71 mmol) was added. A CO-filled balloon was placed on top neck of reaction flask and CO was bubbled directly into reaction from lecture bottole. The flask was then opened to the balloon and $SnBu_3H$ (0.70 g, 2.7 mmol) was added via syringe pump over 1 hour. The reaction solution was heated to 65° C. during the tin addition. The reaction was monitored by LC/MS and it was shown to be complete once the tin addition was complete. Water (0.1% TFA) (200 mL) was then added to reaction solution and a yellow precipitate formed. The mixture was then filtered through celite and the filtrate was evaporated in vacuo. A brown/yellow solid in 50% yield was isolated.

(9-formyl-doxycycline (0.20 g, 0.42 mmol) combined with $InCl_3$ (0.01 g, 0.042 mmol), 4-fluoropiperidine (0.13 g, 0.84 mmol), $Et_3N$ (0.09 g, 0.84 mmol), and DMF (5 mL) in a glass vial. The mixture was stirred under argon at room temperature for 30 minutes. $NaCNBH_3$ (0.037 g, 0.59 mmol) was added to the reaction vial and the reaction continued to be stirred at room temperature under argon. The reaction was monitored by LC/MS and HPLC and shown to be complete after 1 hour. The reaction was quenched with MeOH (15 mL) and the solvent was evacuated in vacuo. The product was isolated by preparative HPLC in 10% yield as a yellow solid. ESI-MS: m/z (M+H) 559.

Synthesis of 9-(Benzyl-methyl-amino)-Propenyl)-Minocycline

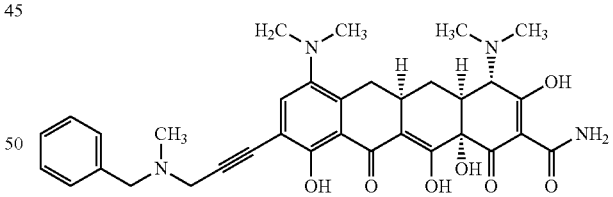

7-Iodo-minocycline (1.08 g, 1.86 mmol), taken in 25 mL of acetonitrile was degassed and purged with nitrogen (three times). To this suspension $Pd(OAc)_2$ (20 mg, 0.089 mmol), CuI (10 mg, 0.053 mmol), (o-tolyl)$_3$P (56 mg, 0.186 mmol) were added and purged with nitrogen for few minutes. Benzyl-methyl-prop-2-ynyl-amine (318 µL, 2 mmol) and triethylamine (1 mL) were added to the suspension. It turned into a brown solution after the addition of $Et_3N$. The reaction mixture was then heated to 70 C for 2 hours. The progress of the reaction was monitored by HPLC/LCMS. It was then cooled down to room temperature and was filtered through celite. Evaporation of the solvent gave a brown solid, which was then purified on preparative HPLC to afford the desired compound. LC-MS (M+1 615).

Synthesis of 8-(2'-[(2'-Fluoro-ethylamino)-methyl]-phenyl)-Sancycline

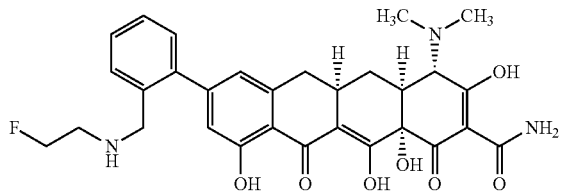 [SMILES: CN(C)[C@@H]1C(O)=C(C(N)=O)C(=O)[C@@]2(O)C(O)=C3C(=O)c4c(O)cc(-c5ccccc5CNCCF)cc4C[C@H]3C[C@@H]12]

Step 1:
To a stirred solution (cooled at 0° C., ice-bath) of 9-amino-sancycline (7 g, 16.3 mmol) in 200 mL of MeOH, 48% $HBF_4$ solution (5.32 mL, 40.75 mmol) was added slowly under an argon atmosphere. After 5 minutes, n-BuNO2 (2.1 mL, 17.93 mmol) was added slowly (drop-wise). The reaction mixture was then stirred at 0 C for 3 hours (monitored by HPLC/LC-MS). $NaN_3$ (1.06 g, 16.3 mmol) was then added the reaction mixture (all at once). The reaction mixture was stirred at 0 C for another 3 hours (monitored by HPLC/LC-MS). The reaction mixture was then poured slowly into stirring diethyl ether (~1 L at ice-bath temperature). A yellow precipitate was obtained and it was filtered, washed with ether (20 ml×3) and dried under vacuum, sealed in a vial and stored at 0 C. Isolated yield 7 g.

Step 2:
Hydrobromic acid (30% in acetic acid) (14 mL) was added to a flask and cooled to 0 C. 9-Azido-sancycline (1 g, 2.2 mmol) was added to the flask and the reaction was left to stir for one hour. After 1 hour, the reaction was complete. The reaction mixture was precipitated in 300 mL of diethyl ether. After letting the solution settle, the top layer of diethyl ether was decanted and the reaction mixture was dried under vacuum. A brown-black solid was then dissolved in methanol and precipitated using diethyl ether. The solid obtained was filtered and dried under vacuum.

Step 3:
To a stirred solution (cooled at 0 C, ice-bath) of 8-bromo-9-amino-sancycline (828 mg, 1.6 mmol) in 200 mL of MeOH, 48% $HBF_4$ solution (0.53 mL, 4.0 mmol) was added slowly under an argon atmosphere. After 5 minutes, n-$BuNO_2$ (0.2 mL, 1.79 mmol) was added slowly (drop-wise). The reaction mixture was then stirred at 0 C for 2 hours and left overnight at room temperature (monitored by HPLC/LC-MS). The solvent was evaporated and the crude material obtained was precipitated using diethyl ether (300 mL). The solid obtained was filtered and dried under vacuum.

Step 4:
8-Bromo-sancycline (492 mg, 1 mmol) and $Pd(OAc)_2$ (22 mg, 0.1 mmol) were taken in methanol (150 mL) and purged with argon while heating the reaction mixture at 65 C (oil bath temperature). After 10 minutes, an aqueous solution of sodium carbonate (315 mg, 3 mmol in 10 mL of water) was added. A yellow precipitate was obtained which was further heated for another 10 minutes, before adding a DMF solution of the boronic acid (300 mg, 2 mmol in 10 mL of DMF). The reaction was then heated at 65 C for 3 hours. The reaction was monitored by HPLC/LCMS. The reaction was cooled down to room temperature and then filtered through celite. The solvent was then evaporated and the crude material obtained was precipitated using methanol/diethyl ether (10/200 mL). The crude material was then filtered and dried under vacuum. The yellow-brown material obtained was used as such without further purification.

Step 5:
To a solution of 8-(2-formyl-phenyl)-sancycline (518 mg, 1 mmol) in 30 mL of DCE under an argon atmosphere, 2-fluoro-ethylamine hydrochloride (198 mg, 2 mmol) and triethylamine (202 µL, 2 mmol) were added. The reaction mixture was then stirred at room temperature for 2 hours. The reaction was monitored by using HPLC/LCMS, and was completed in 2 hours. The solvent was then evaporated and the crude material was purified using preparative HPLC to afford the desired compound. LC-MS (M+1 566).

7-Pyrazolyl-Sancycline

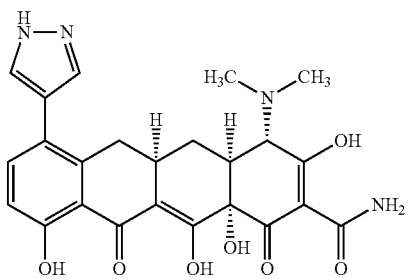 [SMILES: CN(C)[C@@H]1C(O)=C(C(N)=O)C(=O)[C@@]2(O)C(O)=C3C(=O)c4c(O)ccc(-c5cn[nH]c5)c4C[C@H]3C[C@@H]12]

To a stirred solution of 7-Iodo sancycline (100 mg, 0.153 mmol) in DMF (1 mL) was added pyrozole-4-boronic acid pinacole cyclic ester (77 mg, 0.40 mmol), methanol (1.5 mL), tetrakis(triphenylphosphine)palladium (18 mg, 0.015 mmol) and a solution containing 250 mg $CsCO_3$ in 0.7 mL water. The reaction mixture was then subject to microwave irradiation at a temperature of 100 C for 5 minutes. The reaction was then diluted with 100 mL of water and TFA was used to lower the pH to 2. This solution was then filtered through celite, and loaded onto a plug of divinyl benzene resin (DVB). The plug containing the product was washed with water (200 mL) before the final compound was eluted with MeCN and reduced by rotary evaporation. The crude material was purified by reverse phase HPLC to give the final product (64 mg, 0.12 mmol, 75% yield) LCMS m/z=481.2115 (M+H).

Synthesis of 9-[(2,2,2-Trifluoro-ethyl)-hydrazonomethyl]-Minocycline

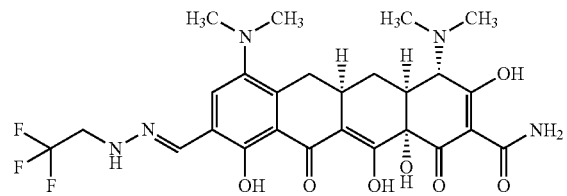 [SMILES: CN(C)c1cc(/C=N/NCC(F)(F)F)c(O)c2c1C[C@H]1C[C@H]3[C@H](N(C)C)C(O)=C(C(N)=O)C(=O)[C@@]3(O)C(O)=C1C2=O]

To a solution of 9-formyl minocycline (485 mg, 1 mmol) in 30 mL of DMF under an argon atmosphere, indium trichloride (22 mg, 0.1 mmol) and trifluoroethylhydrazine (228 µL, 2 mmol) were added. The reaction mixture was then stirred at room temperature for 30 minutes. The reaction was monitored by using HPLC/LCMS, and was completed in 30 minutes. The solvent was then evaporated and the crude material was purified using preparative HPLC to afford the desired compound. LC-MS (M+1 582).

Synthesis of 9-(1'-Isopropyl-4'-piperidinyl) amino Sancycline

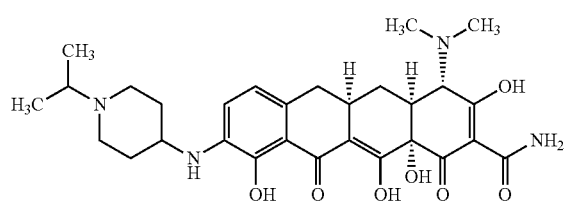 [SMILES: CC(C)N1CCC(Nc2ccc3c(c2O)C(=O)C2=C(O)[C@]4(O)C(=O)C(C(N)=O)=C(O)[C@@H](N(C)C)[C@@H]4C[C@@H]2C3)CC1]

To a solution of 9-amino sancycline HCl salt (0.5 g, 1 mmol) in 40 ml of methanol and was added 1-isopropyl-4-piperidone (0.14 g, 2 mmol). The solution was stirred for 5 minutes at room temperature. Sodium cyanoborohydride (62.5 mg, 1 mmol) was introduced, followed by the addition of 4 ml of AcOH. The mixture was stirred at room temperature for 1 hour until all starting material disappeared. The suspension was filtered and purified by HPLC to afford the title compound (210 mg). LC-MS (M+1 555).

Synthesis of 9-(3-t-butyl-N-imidazolyl)-methyl)-Minocycline

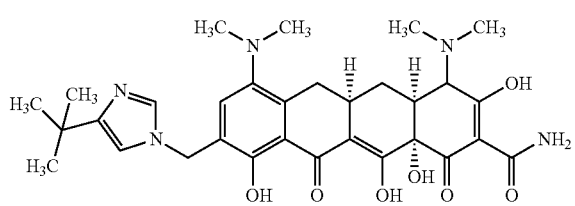 [SMILES: CN(C)c1cc(Cn2cnc(C(C)(C)C)c2)c(O)c2c1C[C@H]1C[C@H]3C(N(C)C)C(O)=C(C(N)=O)C(=O)[C@@]3(O)C(O)=C1C2=O]

To a stirred solution of 9-aminomethyl-minocycline (2.50 g, 4.14 mmol) in DMF (25 mL) and MeOH (15 mL) was added 1-bromopinacolone (1.34 mL, 1.01 g, 5.63 mmol) and $Cs_2CO_3$ (5.0 mL of a 1N aqueous solution, 5.0 mmol). The reaction was heated to 100° C. for 15 minutes in a pressure vesicle using microwave irradiation. The contents were then diluted with water (1.0 L) and $Na_2CO_3$ was used to adjust the pH to 6. This solution was then filtered through celite and loaded onto a plug of divinyl benzene resin. The product was washed with water (500 mL) before it was eluted with MeCN and reduced by rotary evaporation. The crude material was purified by reverse phase HPLC to give the tert-butyl-ketone intermediate (680 mg, 1.90 mmol, 50% yield). To a stirred solution of the tert-butyl-ketone intermediate (68 mg, 0.190 mmol) in formamide (1.0 mL) was added triethyl-amine (0.020 mL, 28 mg, 0.27 mmol) to adjust the pH to 8. The reaction was heated to 100° C. for 5 minutes in a pressure vesicle using microwave irradiation. The contents were then diluted with water (100 mL) and TFA was used to adjust the pH to 2. This solution was then filtered through celite, and loaded onto a plug of divinyl benzene resin. The product was washed with water (200 mL) before it was eluted with MeCN and reduced by rotary evaporation. The crude material was purified by reverse phase HPLC to give the final compound (6.0 mg, 10 μmol, 4% yield) LCMS m/z=594.4863 (M+H).

Synthesis of 9-(2-thiol 5-methyl-N-imidazolyl)-methyl Minocycline

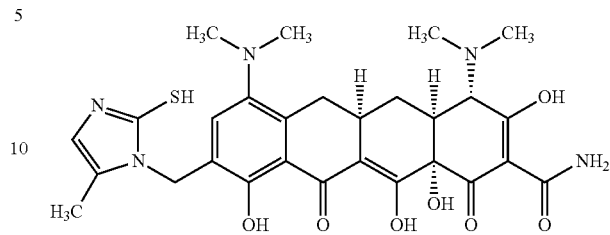

To a stirred solution of 9-aminomethyl-minocycline (2.00 g, 4.12 mmol) in DMF (12 mL), MeOH (6.0 mL) and acetic acid (3.0 mL) was added KSCN (0.400 g, 4.12 mmol) and Acetol 0.400 mL, 0.370 g, 5.00 mmol). The reaction was heated to 100° C. for 15 minutes in a pressure vesicle using microwave irradiation. The contents were then diluted with water (1.0 L) and $Na_2CO_3$ was used to adjust the pH to 6. This solution was then filtered through celite and loaded onto a plug of divinyl benzene resin. The product was washed with water (500 mL) before it was eluted with MeCN and reduced by rotary evaporation. The crude material was purified by reverse phase HPLC to give the final product (620 mg, 1.06 mmol, 26% yield) LCMS m/z=584.3998 (M+H).

Synthesis of 7-(2',2'-dimethyl-propyl)amino methyl Sancycline

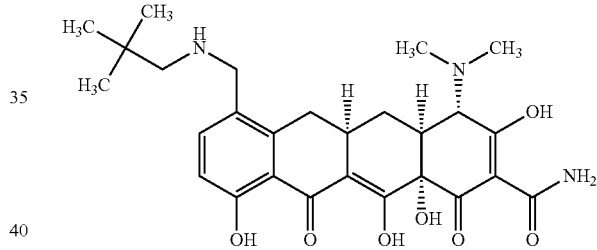

1 g of 7-aminomethyl-sancycline, 3 equivalents of trim-ethylacetaldehyde and one equivalent of indium trichloride were dissolved in 10 ml of DMF. The mixture was stirred at room temperature for 15 minutes. To this mixture was added 3 equivalents of sodium triacetoxyborohydride. The resulting reaction mixture was left stirring for several hours. The reaction was monitored by analytical HPLC. The LCMS showed MS: 514 which corresponds to the desired material. The product was isolated via preparative HPLC and the structure was confirmed by NMR.

Synthesis of 9-(Benzoimidazolyl)-Minocycline

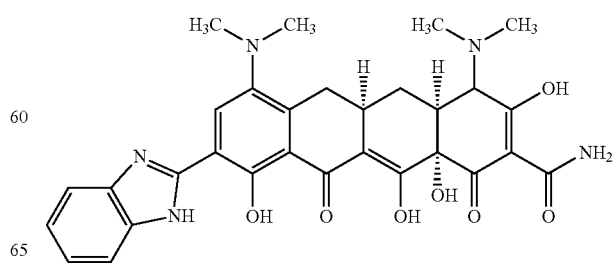

To a stirred solution of the trifluoroacetic acid (TFA) salt of 9-formyl minocycline (488 mg, 1.47 mmol) in DMF (3 mL) and MeOH (2 mL) was added 1,2-phenylenediamine (80 mg, 0.74 mmol). The reaction was heated to 50 C and was complete in 5 minutes. The contents were then diluted with water (500 mL) and TFA was used to adjust the pH to 2. This solution was then filtered through celite, and loaded onto a plug of divinyl benzene resin. The plug containing the product was washed with water (300 mL) before it was eluted with MeCN and reduced by rotary evaporation. The crude material was purified by reverse phase HPLC to give the Benzoimidazol product (100 mg, 0.175 mmol, 10% yield) LCMS m/z=574.3637 (M+H).

Example 2

In Vitro Minimum Inhibitory Concentration (MIC) Assay

The following assay is used to determine the efficacy of the tetracycline compounds against common bacteria. 2 mg of each compound is dissolved in 100 µl of DMSO. The solution is then added to cation-adjusted Mueller Hinton broth (CAMHB), which results in a final compound concentration of 200 µg per ml. The tetracycline compound solutions are diluted to 50 µL volumes, with a test compound concentration of 0.098 µg/ml. Optical density (OD) determinations are made from fresh log-phase broth cultures of the test strains. Dilutions are made to achieve a final cell density of $1\times10^6$ CFU/ml. At OD=1, cell densities for different genera should be approximately:

| | |
|---|---|
| *E. coli* | $1 \times 10^9$ CFU/ml |
| *S. aureus* | $5 \times 10^8$ CFU/ml |
| *Enterococcus* sp. | $2.5 \times 10^9$ CFU/ml |

50 µl of the cell suspensions are added to each well of microtiter plates. The final cell density should be approximately $5\times10^5$ CFU/ml. These plates are incubated at 35° C. in an ambient air incubator for approximately 18 hr. The plates are read with a microplate reader and are visually inspected when necessary. The MIC is defined as the lowest concentration of the tetracycline compound that inhibits growth.

EQUIVALENTS

Those skilled in the art will recognize, or be able to ascertain using no more than routine experimentation, numerous equivalents to the specific procedures described herein. Such equivalents are considered to be within the scope of the present invention and are covered by the following claims. The contents of all references, patents, and patent applications cited throughout this application are hereby incorporated by reference. The appropriate components, processes, and methods of those patents, applications and other documents may be selected for the present invention and embodiments thereof.

The invention claimed is:

1. A tetracycline compound of the following structural formula:

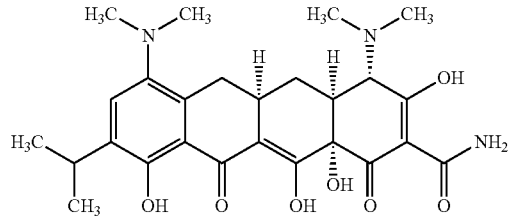 [SMILES: CC(C)c1cc(N(C)C)c2c(c1O)C(=O)C1=C(O)[C@]3(O)C(=O)C(C(N)=O)=C(O)[C@@H](N(C)C)[C@@H]3C[C@@H]1C2]

or a pharmaceutically acceptable salt thereof.

2. A pharmaceutical composition comprising the tetracycline compound of claim 1 and a pharmaceutically acceptable carrier.

* * * * *